US011642400B2

(12) United States Patent
Yu et al.

(10) Patent No.: US 11,642,400 B2
(45) Date of Patent: May 9, 2023

(54) IMMUNOGENIC/THERAPEUTIC GLYCAN COMPOSITIONS AND USES THEREOF

(71) Applicant: OBI PHARMA, INC., Taipei (TW)

(72) Inventors: Cheng-Der Tony Yu, San Diego, CA (US); Peiwen Yu, San Diego, CA (US); Kuo-Pao Lai, Taipei (TW); Wei-Han Lee, Taipei (TW); I-Ju Chen, Taipei (TW); Shu-Yi Lin, Taipei (TW); Yih-Huang Hsieh, Taipei (TW)

(73) Assignee: OBI PHARMA, INC., Taipei (TW)

(*) Notice: Subject to any disclaimer, the term of this patent is extended or adjusted under 35 U.S.C. 154(b) by 0 days.

(21) Appl. No.: 15/662,162

(22) Filed: Jul. 27, 2017

(65) Prior Publication Data

US 2018/0028629 A1 Feb. 1, 2018

Related U.S. Application Data

(60) Provisional application No. 62/367,528, filed on Jul. 27, 2016.

(51) Int. Cl.
*A61K 39/00* (2006.01)

(52) U.S. Cl.
CPC .... *A61K 39/0011* (2013.01); *A61K 39/00118* (2018.08); *A61K 39/001173* (2018.08); *A61K 2039/54* (2013.01); *A61K 2039/545* (2013.01); *A61K 2039/55511* (2013.01); *A61K 2039/55577* (2013.01); *A61K 2039/6037* (2013.01); *A61K 2039/6081* (2013.01); *A61K 2039/627* (2013.01); *A61K 2039/64* (2013.01)

(58) Field of Classification Search
CPC ........ A61K 2039/6081; A61K 2039/64; A61K 2039/627; A61K 39/00118; A61K 39/001173; A61K 2039/55511; A61K 39/001169
IPC .................................................. A61K 39/0011
See application file for complete search history.

(56) References Cited

U.S. PATENT DOCUMENTS

| | | |
|---|---|---|
| 3,773,919 A | 11/1973 | Boswell et al. |
| 4,203,975 A | 5/1980 | Greven |
| RE30,985 E | 6/1982 | Cartaya |
| 4,419,446 A | 12/1983 | Howley et al. |
| 4,522,811 A | 6/1985 | Eppstein et al. |
| 4,560,655 A | 12/1985 | Baker |
| 4,601,903 A | 7/1986 | Frasch |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,849,222 A | 7/1989 | Broaddus |
| 4,927,762 A | 5/1990 | Darfler |
| 4,943,533 A | 7/1990 | Mendelsohn et al. |
| 4,965,199 A | 10/1990 | Capon et al. |
| 4,975,278 A | 12/1990 | Senter et al. |
| 5,004,697 A | 4/1991 | Pardridge |
| 5,057,540 A | 10/1991 | Kensil et al. |
| 5,061,620 A | 10/1991 | Tsukamoto et al. |
| 5,100,669 A | 3/1992 | Hyon et al. |
| 5,112,596 A | 5/1992 | Malfroy-Camine |
| 5,122,469 A | 6/1992 | Genentech |
| 5,212,290 A | 5/1993 | Vogelstein et al. |
| 5,264,365 A | 11/1993 | Georgiou et al. |
| 5,268,164 A | 12/1993 | Kozarich et al. |
| 5,500,362 A | 3/1996 | Robinson et al. |
| 5,506,206 A | 4/1996 | Kozarich et al. |
| 5,508,192 A | 4/1996 | Georgiou et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,569,825 A | 10/1996 | Lonberg et al. |
| 5,571,894 A | 11/1996 | Wels et al. |

(Continued)

FOREIGN PATENT DOCUMENTS

| | | |
|---|---|---|
| CN | 1871025 A | 11/2006 |
| CN | 103108654 A | 5/2013 |

(Continued)

OTHER PUBLICATIONS

Slovin et al (PNAS, 1999, vol. 96, pp. 5710-5715) (Year: 1999).*
Lee et al, (Journal of the American Chemical Society, 2014, vol. 136, pp. 16844-16853) (Year: 2014).*
Ragupathi et al, (Angew Chem Int Engl, 1997, vol. 36, pp. 125-128) (Year: 1997).*
Harris et al (Micron, 1997, vol. 28, pp. 43-56) (Year: 1997).*
Liu et al (Vaccine, 2002, vol. 20, pp. 2808-2815) (Year: 2002).*
International Search Report/Written Opinion dated Oct. 31, 2017 in counterpart PCT Application No. PCT/US2017/044244.

(Continued)

*Primary Examiner* — Karen A. Canella
(74) *Attorney, Agent, or Firm* — Prosyla Group PC

(57) ABSTRACT

The present disclosure encompasses immunogenic/therapeutic compositions including Globo series antigens (SSEA-4, Globo H or SSEA-3) glycoconjugates and therapeutic adjuvants (OBI-821 or OBI-834) as well as methods of making and using the same to treat proliferative diseases such as cancer. The therapeutic conjugates include an antigen linked to a carrier. In particular, the therapeutic conjugates include a SSEA-4, Globo H or SSEA-3 moiety and a KLH moiety subunit linked via a linker. The therapeutic compositions are in part envisaged to act as cancer vaccines (single valent, bi-valent or tri-valent vaccines) for boosting the body's natural ability to protect itself, through the immune system from dangers posed by damaged or abnormal cells such as cancer cells. Exemplary immune response can be characterized by reduction of the severity of disease, including but not limited to, prevention of disease, delay in onset of disease, decreased severity of symptoms, decreased morbidity and delayed mortality.

11 Claims, 23 Drawing Sheets

(23 of 23 Drawing Sheet(s) Filed in Color)

(56) References Cited

U.S. PATENT DOCUMENTS

| | | |
|---|---|---|
| 5,580,717 A | 12/1996 | Dower et al. |
| 5,587,458 A | 12/1996 | King et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,648,237 A | 7/1997 | Carter |
| 5,661,016 A | 8/1997 | Lonberg et al. |
| 5,686,416 A | 11/1997 | Kozarich et al. |
| 5,733,743 A | 3/1998 | Johnson et al. |
| 5,804,396 A | 9/1998 | Plowman |
| 5,814,344 A | 9/1998 | Tice et al. |
| 5,821,337 A | 10/1998 | Carter et al. |
| 5,840,523 A | 11/1998 | Simmons et al. |
| 5,849,906 A * | 12/1998 | Cavalieri ............ C07D 473/00 536/55.3 |
| 5,869,046 A | 2/1999 | Presta et al. |
| 5,891,996 A | 4/1999 | Mateo de Acosta del Rio et al. |
| 6,004,940 A | 12/1999 | Marasco et al. |
| 6,027,888 A | 2/2000 | Georgiou et al. |
| 6,083,715 A | 7/2000 | Georgiou et al. |
| 6,265,150 B1 | 7/2001 | Terstappen et al. |
| 6,329,173 B1 | 12/2001 | Marasco et al. |
| 6,524,584 B2 | 2/2003 | Kensil |
| 6,544,952 B1 | 4/2003 | Danishefsky et al. |
| 6,703,019 B1 | 3/2004 | Malfroy-Camine |
| 7,595,292 B2 | 9/2009 | Brocchini et al. |
| 8,268,969 B2 | 9/2012 | Wong et al. |
| 10,815,307 B2 | 10/2020 | Yu et al. |
| 10,935,544 B2 | 3/2021 | Yu et al. |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0083299 A1 | 5/2003 | Ferguson |
| 2003/0104402 A1 | 6/2003 | Zauderer et al. |
| 2003/0129186 A1 | 7/2003 | Beliveau et al. |
| 2003/0153492 A1 | 8/2003 | Danishefsky et al. |
| 2003/0162695 A1 | 8/2003 | Schatzberg et al. |
| 2004/0018194 A1 | 1/2004 | Francisco et al. |
| 2004/0131692 A1 | 7/2004 | Kreuter et al. |
| 2004/0204354 A1 | 10/2004 | Nelson et al. |
| 2004/0208884 A1 | 10/2004 | Danishefsky et al. |
| 2004/0229310 A1 | 11/2004 | Simmons |
| 2004/0247608 A1 | 12/2004 | Krantz et al. |
| 2005/0048572 A1 | 3/2005 | Reilly et al. |
| 2005/0089473 A1 | 4/2005 | Black et al. |
| 2005/0124533 A1 | 6/2005 | Schatzberg et al. |
| 2006/0035267 A1 | 2/2006 | Livingston et al. |
| 2007/0059769 A1 | 3/2007 | Blixt et al. |
| 2009/0317411 A1 | 12/2009 | Wong et al. |
| 2010/0136042 A1* | 6/2010 | Wong ................ A61K 39/0011 424/193.1 |
| 2010/0166790 A1 | 7/2010 | Agadjanyan et al. |
| 2010/0286035 A1 | 11/2010 | Ohtaki et al. |
| 2011/0117009 A1 | 5/2011 | Kratz et al. |
| 2012/0237532 A1 | 9/2012 | Olbrich et al. |
| 2012/0294859 A1 | 11/2012 | Goletz et al. |
| 2012/0321583 A1 | 12/2012 | Yurkovetskiy et al. |
| 2012/0328646 A1 | 12/2012 | Wong et al. |
| 2013/0095173 A1 | 4/2013 | Danishefsky et al. |
| 2013/0232589 A1 | 9/2013 | Papkoff et al. |
| 2014/0363455 A1 | 12/2014 | Stull et al. |
| 2015/0030669 A1 | 1/2015 | Platscher et al. |
| 2015/0297696 A1 | 10/2015 | Yu et al. |
| 2015/0316556 A1 | 11/2015 | Hardt et al. |
| 2015/0344551 A1 | 12/2015 | Wong et al. |
| 2016/0051672 A1 | 2/2016 | Stewart et al. |
| 2016/0074522 A1 | 3/2016 | Okuda et al. |
| 2016/0102151 A1 | 4/2016 | Wong et al. |
| 2016/0213763 A1* | 7/2016 | Wong ............ A61K 39/001169 |
| 2016/0339089 A1 | 11/2016 | Yu et al. |
| 2017/0067885 A1 | 3/2017 | Yu et al. |
| 2017/0101462 A1 | 4/2017 | Yu et al. |
| 2017/0283488 A1 | 10/2017 | Yu et al. |
| 2017/0283489 A1 | 10/2017 | Bosio et al. |
| 2017/0304419 A1 | 10/2017 | Yu et al. |
| 2017/0335281 A1 | 11/2017 | Loew et al. |
| 2018/0028629 A1 | 2/2018 | Yu et al. |
| 2018/0193481 A1 | 7/2018 | Chang et al. |
| 2018/0291109 A1 | 10/2018 | Lin et al. |
| 2018/0339061 A1 | 11/2018 | Yu et al. |
| 2019/0389963 A1 | 12/2019 | Yu et al. |
| 2020/0062861 A1 | 2/2020 | Yu et al. |
| 2020/0138967 A1 | 5/2020 | Yu et al. |
| 2021/0113711 A1 | 4/2021 | Chang et al. |

FOREIGN PATENT DOCUMENTS

| | | | |
|---|---|---|---|
| EP | 0404097 A2 | 12/1990 | |
| EP | 1391213 A1 | 2/2004 | |
| EP | 2993182 A1 | 3/2016 | |
| JP | 2006-507233 A | 3/2006 | |
| JP | 2011524375 A | 9/2011 | |
| JP | 2011524417 A | 9/2011 | |
| JP | 2016500256 A | 1/2016 | |
| KR | 10-2012-0014238 A | 2/2012 | |
| WO | WO 87/00195 A1 | 1/1987 | |
| WO | WO 90/03184 A1 | 4/1990 | |
| WO | WO 90/03430 A1 | 4/1990 | |
| WO | WO 91/00360 A1 | 1/1991 | |
| WO | WO 91/10741 A1 | 7/1991 | |
| WO | WO 92/00373 A1 | 1/1992 | |
| WO | WO 92/09690 A2 | 6/1992 | |
| WO | WO 93/01161 A1 | 1/1993 | |
| WO | WO 93/06213 A1 | 4/1993 | |
| WO | WO 1993/007861 | 4/1993 | |
| WO | WO 93/08829 A1 | 5/1993 | |
| WO | WO 93/16185 A2 | 8/1993 | |
| WO | WO 94/04690 A1 | 3/1994 | |
| WO | WO 94/011026 A2 | 5/1994 | |
| WO | WO 1995/011010 | 4/1995 | |
| WO | WO 96/07754 A1 | 3/1996 | |
| WO | WO 96/11711 A1 | 4/1996 | |
| WO | WO 96/30347 A1 | 10/1996 | |
| WO | WO 96/33735 A1 | 10/1996 | |
| WO | WO 96/33978 A1 | 10/1996 | |
| WO | WO 96/33980 A1 | 10/1996 | |
| WO | WO 96/34096 A1 | 10/1996 | |
| WO | WO 96/40210 A1 | 12/1996 | |
| WO | WO 97/38983 A1 | 10/1997 | |
| WO | WO 98/24893 A2 | 6/1998 | |
| WO | WO 98/36772 A1 | 8/1998 | |
| WO | WO 98/43960 A1 | 10/1998 | |
| WO | WO 99/06378 A1 | 2/1999 | |
| WO | WO 99/06396 A1 | 2/1999 | |
| WO | WO 99/09016 A1 | 2/1999 | |
| WO | WO 99/042130 A1 | 8/1999 | |
| WO | WO 2000/41720 A1 | 7/2000 | |
| WO | WO 2000/48630 A1 | 8/2000 | |
| WO | WO-2000/49412 A1 | 8/2000 | |
| WO | WO 2003/015796 A1 | 2/2003 | |
| WO | WO 2003/043583 A2 | 5/2003 | |
| WO | WO 2003/077945 A1 | 9/2003 | |
| WO | WO 2004/011476 A1 | 2/2004 | |
| WO | WO 2004/032828 A2 | 4/2004 | |
| WO | WO 2005/007197 A2 | 1/2005 | |
| WO | WO 2006/105152 A2 | 10/2006 | |
| WO | WO 2006/134423 A2 | 12/2006 | |
| WO | WO 2007/026190 A2 | 3/2007 | |
| WO | WO 2007/044515 A1 | 4/2007 | |
| WO | WO-2007047764 A2 * | 4/2007 | ......... A61K 39/0011 |
| WO | WO 2009/035494 A2 | 3/2009 | |
| WO | WO 2009/126737 A2 | 10/2009 | |
| WO | 2010005735 A3 | 3/2010 | |
| WO | WO-2011156774 A2 * | 12/2011 | ......... A61K 39/0011 |
| WO | WO 2014/107652 A2 | 7/2014 | |
| WO | WO 2014/178195 A1 | 11/2014 | |
| WO | WO 2015/143123 A2 | 9/2015 | |
| WO | WO 2015/157629 A1 | 10/2015 | |
| WO | WO 2015/159118 A2 | 10/2015 | |
| WO | 2015157629 A3 | 12/2015 | |
| WO | WO 2016/026742 A1 | 2/2016 | |
| WO | WO 2016/044326 A1 | 3/2016 | |
| WO | 2016118961 A1 | 7/2016 | |

(56) References Cited

FOREIGN PATENT DOCUMENTS

| WO | WO 2016/118961 A1 | 7/2016 |
|---|---|---|
| WO | WO 2016/123593 A1 | 8/2016 |
| WO | 2017004150 A1 | 1/2017 |
| WO | WO 2017/041027 A1 | 3/2017 |
| WO | 2017062792 A1 | 4/2017 |
| WO | WO 2017/062792 A1 | 4/2017 |
| WO | 2016044326 A9 | 5/2017 |
| WO | 2017185089 A2 | 10/2017 |
| WO | WO 2017/172990 A1 | 10/2017 |
| WO | 2018022933 A1 | 2/2018 |
| WO | WO 2018/022933 A1 | 2/2018 |
| WO | WO 2018/023121 A1 | 2/2018 |
| WO | WO 2018/094414 A1 | 5/2018 |

OTHER PUBLICATIONS

Lucas, A.H. et al., Carbohydrate Moieties as Vaccine Candidates: Meeting Summary, Vaccine, vol. 28(4), Jan. 2010, pp. 1121-1131.
Zhou, Zhifang et al., A Fully Synthetic Self-Adjuvanting Globo H-Based Vaccine Elicited Strong T Cell-Mediated Antitumor Immunity, Chem. Sci., 2015, 6, 7112-7121.
Allen, P. Z. et al., Immunochemical Studies on a Sophorosyl-Azoprotein Conjugate, Biochemistry, 1967, 6(10), 3029.
Avery, Oswald et al., Chemo-Immunological Studies on Conjugated Carbohydrate-Proteins, J. Exp. Med., 1929, 50, 533-550.
Fielder, R. J. et al., An Immunogenic Polysaccharide-Protein Conjugate, J. Immunol., 1970, 105(1), 265-267.
Chang, Wen-Wei et al., Expression of Globo H and SSEA3 in Breast Cancer Stem Cells and the Involvement of Fucosyl Transferases 1 and 2 in Globo H Synthesis, PNAS, 105(33): 11667-11672, 2008.
Goebel, Walther et al., Chemo-immunological Studies on Conjugated Carbohydrate-Proteins, J. Exp. Med., 1929, 50, 521-531.
Himmelspach, K. et al., Use of 1-(m-aminophenyl)flavazoles for the Preparation of Immunogens with Oligosaccharide Determinant Groups, Eur. J. Immunol., 1971, 1(2), 106-112.
Kannagi, Reiji et al., Stage-Specific Embryonic Antigens (SSEA-3 and -4) are Epitopes of a Unique Globo-Series Ganglioside Isolated From Human Teratocarinoma Cells, EMBO J, 2(12), 2355-2361, 1983.
Lloyd, Kenneth, in Specific Immunotherapy of Cancer with Vaccines, 1993, 690, 50-58.
Lou, Yi-Wen et al., Stage-Specific Embryonic Antigen-4 as a potential Therapeutic Target in Glioblastoma Multiforme and Other Cancers, PNAS, 111(7): 2482-2487, 2014.
Rüde, Erwin et al., Synthesis of the N-carboxy-α-amino Acid Anhydrides of Several O-acetylated Serine Glycosides, Carbohydr. Research, 1968, 8(2), 219-232.
Toyokuni, Tatsushi et al., Synthetic Vaccines: Synthesis of a Dimeric Tn Antigen-Lipopeptide Conjugate That Elicits Immune Responses Against Tn-Expressing Glycoproteins, J. Am. Chem. Soc., 1994, 116(1), 395-396.
Abrahmsén et al., "Analysis of signals for secretion in the staphylococcal protein A gene," EMBO J., Dec. 30, 1985, 4(13B):3901-3906.
Arié et al., "Chaperone function of FkpA, a heat shock prolyl isomerase, in the periplasm of Escherichia coli," Mol. Microbiol., Jan. 2001, 39(1):199-210.
Arigi, Emma, et al. "Design of a covalently bonded glycosphingolipid microarray." Glycoconjugate Journal 29.1 (2012): 1-12.
Bachmann, Cellular and Molecular Biology, vol. 2, Chapter 72: Derivations and Genotypes of Some Mutant Derivatives of Escherichia coli K-12, Neidhardt et al., eds., 1987, pp. 1190-1219, American Society for Microbiology, Washington, D.C.
Baldwin et al., "Monoclonal antibodies in cancer treatment," Lancet, Mar. 15, 1986, 327(8481):603-605.
Barbas et al., "Assembly of combinatorial antibody libraries on phage surfaces: the gene III site," Proc. Natl. Acad. Sci. U.S.A., Sep. 15, 1991, 88(18):7978-7982.

Barbas, C.F. et al., "Semisynthetic combinatorial antibody libraries: a chemical solution to the diversity problem" Proc. Natl. Acad. Sci. USA, May 15, 1992, 89(10):4457-4461.
Barbas et al., "In vitro evolution of a neutralizing human antibody to human immunodeficiency virus type 1 to enhance affinity and broaden strain cross-reactivity," Proc. Nat. Acad. Sci. U.S.A., Apr. 26, 1994, 91(9):3809-3813.
Barnes et al., "Methods for growth of cultured cells in serum-free medium," Anal. Biochem., Mar. 1, 1980, 102(2):255-270.
Bass et al., "Hormone phage: an enrichment method for variant proteins with altered binding properties," Proteins, 1990, 8(4):309-314.
Berenbaum, M. C., What is Synergy?, Pharmacol. Rev. 41(2):93-141, 1989.
Bergman, Jan, and Lennart Venemalm. "Efficient synthesis of 2-chloro-, 2-bromo-, and 2-iodoindole." The Journal of Organic Chemistry 57.8 (1992): 2495-2497.
Bertozzi, CR et al., Glycans in Cancer and Inflammation-Potential for Therapeutics and Diagnostics, Nat Rev Drug Discovery, 2005, 4, 477-488.
Bhaskar, Vinay, et al. "E-selectin up-regulation allows for targeted drug delivery in prostate cancer." Cancer Research 63.19 (2003): 6387-6394.
Bird, R.E., et al., "Single-chain antigen-binding proteins" Science Oct. 21, 1988; 242(4877):423-426.
Bliss, C.I., The Calculation of Microbial Assays, Bacterial. Rev. 20:243-258, 1956.
Bobo et al., "Convection-enhanced delivery of macromolecules in the brain," Proc. Natl. Acad. Sci. U.S.A., Mar. 15, 1994, 91(6) 2076-2080.
Boerner et al., "Production of antigen-specific human monoclonal antibodies from in vitro-primed human splenocytes," J. Immunol., Jul. 1, 1991, 147(1):86-95.
Borisy, Alexis et al., Systematic Discovery of Multicomponent Therapeutics, Proc. Natl. Acad. Sci. 100(13):7977-7982, 2003.
Bosse, Folkert et al., Linear Synthesis of the Tumor-Associated Carbohydrate Antigens Globo-H, SSEA-3, and Gb3, J Org Chem. 67(19):6659-70, 2002.
Bothmann et al., "The periplasmic Escherichia coli peptidylprolyl cis,trans-isomerase FkpA. I. Increased functional expression of antibody fragments with and without cis-prolines," J. Biol. Chem., Jun. 2, 2000, 275(22):17100-17105.
Bowie, Ju et al., Deciphering the Message in Protein Sequences: Tolerance to Amino Acid Substitutions, Science, 247: 1306-1310 (1990).
Bremer, E. G., et al. "Characterization of a glycosphingolipid antigen defined by the monoclonal antibody MBr1 expressed in normal and neoplastic epithelial cells of human mammary gland." Journal of Biological Chemistry 259.23 (1984): 14773-14777.
Brennan et al., "Preparation of bispecific antibodies by chemical recombination of monoclonal immunoglobulin G1 fragments," Science, Jul. 5, 1985, 229(4708):81-83.
Brodeur et al., Monoclonal Antibody Production Techniques and Applications, Chapter 4: Mouse-Human Myeloma Partners for the Production of Heterohybridomas, Schook, ed., 1987, pp. 51-63, Marcel Dekker, Inc., New York.
Brüggemann et al., "Designer mice: the production of human antibody repertoires in transgenic animals," Year in Immunol., 1993, 7:33-40.
Carter et al., "High level Escherichia coli expression and production of a bivalent humanized antibody fragment," Nature Biotechnology, Feb. 1992, 10(2):163-167.
Carter et al., "Humanization of an anti-p185$^{HER2}$ antibody for human cancer therapy," Proc. Natl. Acad. Sci. U.S.A., May 15, 1992, 89(10):4285-4289.
Casset, Florence, et al. "A peptide mimetic of an anti-CD4 monoclonal antibody by rational design." Biochemical and Biophysical Research Communications 307.1 (2003): 198-205.
Chang et al., "Potent immune-modulating and anticancer effects of NKT cell stimulatory glycolipids," Proc. Natl. Acad. Sci. USA, Jun. 19, 2007, 104(25):10299-10304.
Chen et al., "Chaperone activity of DsbC," J. Bio. Chem., July 9, 1999, 274(28):19601-19605.

(56) References Cited

OTHER PUBLICATIONS

Chen et al., "Selection and analysis of an optimized anti-VEGF antibody: crystal structure of an affinity-matured Fab in complex with antigen," J. Mol. Biol., Nov. 5, 1999, 293(4):865-881.

Chen et al., "Selective killing of transformed cells by cyclin/cyclin-dependent kinase 2 antagonists," Proc. Natl. Acad. Sci. U.S.A., Apr. 13, 1999, 96(8):4325-4329.

Chen, Wei, et al. "Determination of thiols and disulfides via HPLC quantification of 5-thio-2-nitrobenzoic acid." Journal of Pharmaceutical and Biomedical Analysis 48.5 (2008): 1375-1380.

Cheung, Sarah et al., Stage-Specific Embryonic Antigen-3 (SSEA-3) and B3GalT5 are cancer specific and Significant Markers for Breast Cancer Stem Cells, PNAS, Jan. 26, 2016, vol. 113, No. 4, pp. 960-965.

Chothia et al., "Canonical structures for the hypervariable regions of immunoglobulins," J. Mol. Biol., Aug. 20, 1987, 196(4):901-917.

Chou, Ting-Chao and Talalay, Paul, A Simple Generalized Equation for the Analysis of Multiple Inhibitions of Michaelis-Menten Kinetic Systems, J. Biol. Chem. 252:6438-6442, 1977.

Chou, T. C. and Talalay, P., Quantitative Analysis of Dose-Effect Relationships: The Combined Effects of Multiple Drugs or Enzyme Inhibitors. Adv. Enzyme Regul. 22:27-55, 1984.

Chuang, Po-Kai, et al. "Signaling pathway of globo-series glycosphingolipids and β1, 3-galactosyltransferase V (β3GalT5) in breast cancer." Proceedings of the National Academy of Sciences 116.9 (2019): 3518-3523.

Clackson et al., "Making antibody fragments using phage display libraries," Nature, Aug. 15, 1991, 352(6336):624-628.

ClinicalTrials.gov [Internet]. Bethesda (MD): National Library of Medicine (US). Jan. 24, 2012-. Trial of Active Imunotherapy with Globo H-KLH (OPT-822) in Metastatic Breast Cancer Subjects); Jan. 24, 2012 [cited Oct. 11, 2017]; [about 7 screens]. Available from: https:clinicaltrials.gov/ct2/show/NCT01516307.

Clynes, Raphael, et al. "Fc receptors are required in passive and active immunity to melanoma." Proceedings of the National Academy of Sciences 95.2 (1998): 652-656.

Colman, P.M., "Effects of amino acid sequence changes on antibody-antigen interactions," Research in Immunology 145:33-36, 1994.

Cunningham et al., "High-resolution epitope mapping of hGH-receptor interactions by alanine-scanning mutagenesis," Science, Jun. 2, 1989, 244(4908):1081-1085.

Cuzick, J., et al. "Overview of the main outcomes in breast-cancer prevention trials." The Lancet 361.9354 (2003): 296-300.

Danishefsky, Samuel J., et al. "Development of Globo-H cancer vaccine." Accounts of Chemical Research 48.3 (2015): 643-652.

De Pascalis, Roberto, et al. "Grafting of "abbreviated" complementarity-determining regions containing specificity-determining residues essential for ligand contact to engineer a less immunogenic humanized monoclonal antibody." The Journal of Immunology 169.6 (2002): 3076-3084.

Doronina, Svetlana O., et al. "Development of potent monoclonal antibody auristatin conjugates for cancer therapy." Nature Biotechnology 21.7 (2003): 778-784.

Eller, Chelcie et al., Human Cancer Antigen Globo H is a Cell-Surface Ligand for Human Ribonuclease 1, ACS Central Science. vol. 1, p. 181-90, Jul. 13, 2015.

Embleton et al., "In-cell PCR from mRNA: amplifying and linking the rearranged immunoglobulin heavy and light chain V-genes within single cells," Nucl. Acids Res., Aug. 11, 1992, 20(15):3831-3837.

Engels et al., "Gene synthesis [new synthetic methods (77)]," Angew. Chem. Int. Ed. Engl., Jun. 1989, 28(6):716-734.

Evans, T. R. J., and S. B. Kaye. "Vaccine therapy for cancer—fact or fiction?" Q J Med 92.6 (1999): 299-307.

Extended European Search Report, Application No. 15842660.1, dated Mar. 12, 2018, 9 pages.

Extended European Search Report from corresponding European App. No. 16843131.0, dated Feb. 14, 2019, 13 Pages.

Fellouse et al., "Synthetic antibodies from a four-amino-acid code: a dominant role for tyrosine in antigen recognition," Proc. Natl. Acad. Sci. U.S.A., Aug. 24, 2004, 101(34):12467-12472.

Feng, Li. "Probing lipid-protein interactions using lipid microarrays." Prostaglandins & other lipid mediators 77.1-4 (2005): 158-167.

Fishwild et al., "High-avidity human IgGk monoclonal antibodies from a novel strain of minilocus transgenic mice," Nature Biotechnol., Jul. 1996, 14(7):845-851.

Fitzgerald, Jonathan et al., Systems Biology and Combination Therapy in the Quest for Clinical Efficacy, Nature Chem. Biol. 2(9):458-466, 2006.

Francisco, Joseph A., et al. "cAC10-vcMMAE, an anti-CD30-monomethyl auristatin E conjugate with potent and selective anti-tumor activity." Blood 102.4 (2003): 1458-1465.

Galfrè et al., "Preparation of monoclonal antibodies: strategies and procedures," Methods Enzymol., 1981, 73(Pt B):3-46.

Gazzano-Santoro, Hélène, et al. "A non-radioactive complement-dependent cytotoxicity assay for anti-CD20 monoclonal antibody." Journal of Immunological Methods 202.2 (1997): 163-171.

Gijsen, H.J. et al., Recent Advances in the Chemoenzymatic Synthesis of Carbohydrates and Carbohydrate Mimetics, Chem. Rev., 96, 443-473, 1996.

Gilewski, Teresa et al., Immunization of Metastatic Breast Cancer Patients with a Fully Synthetic Globo H Conjugate: A Phase I Trial, Proc Natl Acad Sci USA 98:3270-3275, 2001.

Gill et al., "Direct brain infusion of glial cell line-derived neurotrophic factor in Parkinson disease," Nature Med., May 2003, 9(5):589-595 and Addendum from Apr. 2006, 12(4):479.

Goding, Monoclonal Antibodies: Principles and Practice 2nd ed., Chapter 3: Production of Monoclonal Antibodies, 1986, pp. 59-103, Academic Press, London.

Gonnet, GH et al., Exhaustive Matching of the Entire Protein Sequence Database, Science 256: 1443-1445 (1992).

Graham et al., "Characteristics of a human cell line transformed by DNA from human adenovirus type 5," J. Gen. Virol., Jul. 1977, 36(1):59-72.

Gram et al., "In vitro selection and affinity maturation of antibodies from a naive combinatorial immunoglobulin library," Proc. Natl. Acad. Sci. U.S.A., Apr. 15, 1992, 89(8):3576-3580.

Grant, Oliver C., et al. "Presentation, presentation, presentation! Molecular-level insight into linker effects on glycan array screening data." Glycobiology 24.1 (2014): 17-25.

Greco, William et al., The Search for Synergy: A Critical Review From a Response Surface Perspective, Pharmacol. Rev. 47(2):331-385, 1995.

Griffiths et al., "Human anti-self antibodies with high specificity from phage display libraries," EMBO J., Feb. 1993, 12(2):725-734.

Gruber et al., "Efficient tumor cell lysis mediated by a bispecific single chain antibody expressed in *Escherichia coli*," J. Immunol., Jun. 1, 1994, 152(11):5368-5374.

Guss et al., "Structure of the IgG-binding regions of streptococcal protein G," EMBO J., Jul. 1986, 5(7):1567-1575.

Hakomori et al., "Glycosphingolipid antigens and cancer therapy," Chem. & Biol., Feb. 1997, 4(2):97-104.

Hakomori, Sen-Itiroh, Tumor-associated carbohydrate antigens defining tumor malignancy: Basis for development of and-cancer vaccines, 2001, Advances in Experimental Medicine and Biology. 491:369-402.

Ham, Richard et al., Media and Growth Requirements, Meth. Enz 58, 44-93 (1979).

Hammerling et al., "Production of antibody-producing hybridomas in the rodent systems." in: Monoclonal Antibodies and T-Cell Hybridomas, 563-587, 1981, Elsevier North-Holland.

Hara et al., "Overproduction of penicillin-binding protein 7 suppresses thermosensitive growth defect at low osmolarity due to an spr mutation of *Escherichia coli*," Microbial Drug Resistance, Spring 1996, 2(1):63-72.

Harris, "Production of humanized monoclonal antibodies for in vivo imaging and therapy," Biochem. Soc. Transactions, Nov. 1995, 23(4):1035-1038.

Harris, J. R., and J. Mark I. "Keyhole limpet hemocyanin (KLH): a biomedical review." Micron 30.6 (1999): 597-623.

(56) References Cited

OTHER PUBLICATIONS

Hawkins et al., "Selection of phage antibodies by binding affinity. Mimicking affinity maturation," J. Mol. Biol., 1992, 226(3):889-896.
Heffernan, Michael J., et al. "In vivo efficacy of a chitosan/IL-12 adjuvant system for protein-based vaccines." Biomaterials 32.3 (2011): 926-932.
Hernández-Ledesma, Blanca, Chia-Chien Hsieh, and O. Ben. "Lunasin, a novel seed peptide for cancer prevention." Peptides 30.2 (2009): 426-430.
Hinman et al., "Preparation and characterization of monoclonal antibody conjugates of the calicheamicins: a novel and potent family of antitumor antibiotics," Cancer Res., Jul. 15, 1993, 53(14):3336-3342.
Hirabayashi, J. et al., Oligosaccharide Microarrays for Glycomics, Trends in Biotechnology 21 (4): 141-143, 2003.
Hirano, Fumiya, et al. "Blockade of B7-H1 and PD-1 by monoclonal antibodies potentiates cancer therapeutic immunity." Cancer Research 65.3 (2005): 1089-1096.
Hogrefe, H.H. et al., "A bacteriophage lambda vector for the cloning and expression of immunoglobulin Fab fragments on the surface of filamentous phage" Gene, 1993, 128(1): 119-126.
Holliger et al., "'Diabodies': small bivalent and bispecific antibody fragments," Proc. Natl. Acad. Sci. U.S.A., Jul. 15, 1993, 90(14):6444-6448.
Holm, Patrik, Rozbeh Jafari, and Birgitta E. Sundström. "Functional mapping and single chain construction of the anti-cytokeratin 8 monoclonal antibody TS1." Molecular Immunology 44.6 (2007): 1075-1084.
Hoogenboom et al., "By-passing immunisation: Human antibodies from synthetic repertoires of germline VH gene segments rearranged in vitro," J. Mol. Biol., Sep. 20, 1992, 227(2):381-388.
Hoogenboom et al., "Multi-subunit proteins on the surface of filamentous phage: methodologies for displaying antibody (Fab) heavy and light chains," Nucl. Acids Res., Aug. 11, 1991 19(15):4133-4137.
Huang, Cheng-Yuan et al., Carbohydrate Microarray for Profiling the Antibodies Interacting with Globo H Tumor Antigen, Proc Natl Acad Sci, 103:15-20, 2006.
Huang, Yen-Lin, and Chung-Yi Wu. "Carbohydrate-based vaccines: challenges and opportunities." Expert Review of Vaccines 9.11 (2010): 1257-1274.
Huang, Yen-Lin, et al. "Carbohydrate-based vaccines with a glycolipid adjuvant for breast cancer." Proceedings of the National Academy of Sciences 110.7 (2013): 2517-2522.
Hurle et al., "Protein engineering techniques for antibody humanization," Curr. Opin. Biotechnol., Aug. 1994, 5(4):428-433.
Huston, James et al, "Protein Engineering of Antibody Binding Sites: Recovery of Specific Activity in an Anti-Digoxin Single-Chain Fv Analogue Produced in *Escherichia coli*" Proc. Natl. Acad. Sci. USA, 1988, 85:5879-5883.
International Search Report dated Jan. 8, 2016 in counterpart application PCT/IB2014/002744, 3 pages.
International Search Report and Written Opinion of the International Searching Authority, from corresponding International Patent Application No. PCT/US2015/050270, dated Dec. 15, 2015, 14 Pages.
International Search Report and Written Opinion of the International Searching Authority, from corresponding International Patent Application No. PCT/US16/50252, dated Nov. 17, 2016, 12 Pages.
International Search Report and Written Opinion dated Jul. 7, 2017, from corresponding International Patent Application No. PCT/US2017/024853, by Yu, Cheng-Der Tony et al., "Antibodies, Pharmaceutical Compositions and Methods", filed Mar. 29, 2017, 21 pages.
International Search Report dated Nov. 28, 2017 in counterpart application PCT/US2017/044713, 6 pages.
International Search Report/Written Opinion dated Mar. 12, 2018 in counterpart PCT Application No. PCT/US17/062886, 22 pages.
International Search Report/Written Opinion dated Oct. 18, 2019 in counterpart application PCT/US2019/035168, 13 pages.
Jackson et al., "In vitro antibody maturation: Improvement of a high affinity, neutralizing antibody against IL-1β," J. Immunol., Apr. 1, 1995, 154(7):3310-3319.
Jakobovits et al., "Analysis of homozygous mutant chimeric mice: deletion of the immunoglobulin heavy-chain joining region blocks B-cell development and antibody production," Proc. Natl. Acad. Sci. U.S.A., Mar. 15, 1993, 90(6):2551-2555.
Jakobovits et al., "Germ-line transmission and expression of a human-derived yeast artificial chromosome," Nature, Mar. 18, 1993, 362(6417):255-258.
Jeon, Insik et al., A Practical Total Synthesis of Globo-H for Use in Anticancer Vaccines, J. Org. Chem., 2009, 74(21), pp. 8452-8455.
Jones et al., "Rapid PCR-cloning of full-length mouse immunoglobulin variable regions," Nature Biotechnol., Jan. 1991, 9(1):88-89.
Jones et al., "Replacing the complementarity-determining regions in a human antibody with those from a mouse," Nature, May 29-Jun. 4, 1986, 321(6069):522-525.
Jones, "Analysis of polypeptides and proteins," Adv. Drug Delivery Rev., Jan.-Apr. 1993, 10(1):29-90.
Kam et al., "Carbon nanotubes as multifunctional biological transporters and near-infrared agents for selective cancer cell destruction," Proc. Natl. Acad. Sci. U.S.A., Aug. 16, 2005, 102(33):11600-11605.
Kannagi et al., "New globoseries glycosphingolipids in human teratocarcinoma reactive with the monoclonal antibody directed to a developmentally regulated antigen, stage-specific embryonic antigen 3," J. Biol. Chem., Jul. 25, 1983, 258(14):8934-8942.
Klussman, Kerry, et al. "Secondary mAb-vcMMAE conjugates are highly sensitive reporters of antibody internalization via the lysosome pathway." Bioconjugate chemistry 15.4 (2004): 765-773.
Koeller, Kathryn et al., Enzymes for Chemical Synthesis, Nature, 409, 232-240, 2001.
Kohler et al., "Continuous cultures of fused cells secreting antibody of predefined specificity," Nature, Aug. 7, 1975, 256(5517):495-497.
Komenaka, Ian, Heidi Hoerig, and Howard L. Kaufman. "Immunotherapy for melanoma." Clinics in Dermatology 22.3 (2004): 251-265.
Konecny, G. et al., Drug Interactions and Cytotoxic Effects of Paclitaxel in Combination with Carboplatin, Epirubicin, Gemcitabine or Vinorelbine in Breast Cancer Cell Lines and Tumor Samples, Breast Cancer Res. and Treatment 67:223-233, 2001.
Kontermann, "Intrabodies as therapeutic agents," Methods, Oct. 2004, 34(2):163-170.
Kostelny et al., "Formation of a bispecific antibody by the use of leucine zippers," J. Immunol., Mar. 1, 1992, 148(5):1547-1553.
Kozbor, "A human hybrid myeloma for production of human monoclonal antibodies," J. Immunol., Dec. 1984, 133(6):3001-3005.
Krainer, Florian et al., An Updated View on Horseradish Peroxidases: Recombinant Production and Biotechnological Applications, Applied Microbiology and Biotechnology, vol. 99, p. 1611-1625, Jan. 11, 2015.
Kufer, Peter, et al. "A revival of bispecific antibodies." Trends in biotechnology 22.5 (2004): 238-244.
Lee et al., "Bivalent antibody phage display mimics natural immunoglobulin," J. Immunol. Methods, Jan. 2004, 284(1-2):119-132.
Lee et al., "High-affinity human antibodies from phage-displayed synthetic Fab libraries with a single framework scaffold," J. Mol. Biol., Jul. 23, 2004, 340(5):1073-1093.
Lehninger, Biochemistry: The Molecular Basis of Cell Structure and Function, 2nd ed., 1975, pp. 73-75, Worth Publishers, New York.
Leung et al., "A method for random mutagenesis of a defined DNA segment using a modified polymerase chain reaction," Technique—A Journal of Methods in Cell and Molecular Biology, Aug. 1989, 1(1):11-15.

(56) References Cited

OTHER PUBLICATIONS

Liang, Pi-Hui, et al. "Quantitative Microarray Analysis of Intact Glycolipid—CD1d Interaction and Correlation with Cell-Based Cytokine Production." Journal of the American Chemical Society 130.37 (2008): 12348-12354.
Lindmark et al., "Binding of immunoglobulins to protein A and immunoglobulin levels in mammalian sera," J. Immunol. Meth., Aug. 12, 1983, 62(1):1-13.
Liu et al., "Eradication of large colon tumor xenografts by targeted delivery of maytansinoids," Proc. Natl., Acad. Sci. U.S.A., Aug. 6, 1996, 93(16):8618-8623.
Livingston, Philip, "Augmenting the immunogenicity of carbohydrate tumor antigens" Seminars in Cancer Biology, Cancer Biol, 6(6):357-366, 1995.
Lode et al., "Targeted therapy with a novel enediyne antibiotic calicheamicin θI1 effectively suppresses growth and dissemination of liver metastases in a syngeneic model of murine neuroblastoma," Cancer Res., Jul. 15, 1998, 58(14):2925-2928.
Lonberg et al., "Antigen-specific human antibodies from mice comprising four distinct genetic modifications," Nature, Apr. 28, 1994, 368(6474):856-859.
Lonberg et al., "Human antibodies from transgenic mice," Int. Rev. Immunol., 1995, 13(1):65-93.
Mandler et al., "Immunoconjugates of geldanamycin and anti-HER2 monoclonal antibodies: antiproliferative activity on human breast carcinoma cell lines," J. Nat. Cancer Inst., Oct. 4, 2000, 92(19):1573-1581.
Mandler et al., "Modifications in synthesis strategy improve the yield and efficacy of geldanamycin-herceptin immunoconjugates," Bioconjugate Chem., Jul.-Aug. 2002, 13(4):786-791.
Mandler et al., "Synthesis and evaluation of antiproliferative activity of a geldanamycin-Herceptin™ immunoconjugate," Bioorganic & Med. Chem. Letters, May 15, 2000, 10(10):1025-1028.
Mao, Shenlan, et al. "Phage-display library selection of high-affinity human single-chain antibodies to tumor-associated carbohydrate antigens sialyl Lewisx and Lewisx." Proceedings of the National Academy of Sciences 96.12 (1999): 6953-6958.
Mao, Weiguang, et al. "EphB2 as a therapeutic antibody drug target for the treatment of colorectal cancer." Cancer Research 64.3 (2004): 781-788.
Marasco et al., "Design, intracellular expression, and activity of a human anti-human immunodeficiency virus type 1 gp120 single-chain antibody," Proc. Natl. Acad. Sci. U.S.A., Aug. 15, 1993, 90(16):7889-7893.
Marasco, "Intrabodies: turning the humoral immune system outside in for intracellular immunization," Gene Therapy, Jan. 1997, 4(1):11-15.
Marks et al., "By-passing immunization. Human antibodies from V-gene libraries displayed on phage," J. Mol. Biol., Dec. 5, 1991, 222(3):581-597.
Marks et al., "By-passing immunization: Building high affinity human antibodies by chain shuffling," Nature Biotechnology, Jul. 1992, 10(7):779-783.
Martineau, R.S. et al., Immunochemical Studies on a Panosyl-Azoprotein conjugate, Immunochemistry, vol. 8, 705-718, 1971.
Mather et al., "Culture of testicular cells in hormone-supplemented serum-free medium," Annals N.Y. Acad. Sci., 1982, 383:44-68.
Mather, "Establishment and characterization of two distinct mouse testicular epithelial cell lines," Biol. Reprod., Aug. 1980, 23(1):243-252.
Matsuda, F. et al., "Structure and physical map of 64 variable segments in the 3' 0.8-megabase region of the human immunoglobulin heavy-chain locus." Nature Genet., 1993, 3: 88-94.
McCafferty et al., "Phage antibodies: Filamentous phage displaying antibody variable domains," Nature, Dec. 6, 1990, 348:552-554.
Menard S et al., Generation of Monoclonal Antibodies Reacting with Normal and Cancer Cells of Human Breast, Cancer Res 43: 1295-1300, 1983.
Miller, Kathy, et al. "Design, construction, and in vitro analyses of multivalent antibodies." The Journal of Immunology 170.9 (2003): 4854-4861.
Milstein, C & Cuello, AC, Hybrid Hydridomas and their use in immunohistochemistry, Nature 305, 537-540, Oct. 1983.
Morimoto et al., "Single-step purification of F(ab')2 fragments of mouse monoclonal antibodies (immunoglobulins G1) by hydrophobic interaction high performance liquid chromatography using TSKgel Phenyl-5PW," J. Biochem. Biophys. Meth., Mar. 1992, 24(1-2):107-117.
Morrison et al., "Chimeric human antibody molecules: mouse antigen-binding domains with human constant region domains," Proc. Natl. Acad. Sci. U.S.A., Nov. 1984, 81(21):6851-6855.
Morrison, "Immunology. Success in specification," Nature, Apr. 28, 1994, 368(6474):812-813.
Munson et al., "LIGAND: a versatile computerized approach for characterization of ligand-binding systems," Anal. Biochem., Sep. 1, 1980, 107(1):220-239.
Neuberger et al., "Recombinant antibodies possessing novel effector functions," Nature, Dec. 13-19, 1984, 312(5995):604-608.
Neuberger, "Generating high-avidity human Mabs in mice," Nature Biotechnol., Jul. 1996, 14(7):826.
Nicolaou, K.C. et al., "Calicheamicin $\Theta^1_1$: A rationally designed molecule with extremely potent and selective DNA cleaving properties and apoptosis inducing activity." Angew. Chem. Intl. Ed. Engl., Feb. 1, 1994, 33(2):183-186.
Niculescu-Duvaz et al., "Antibody-directed enzyme prodrug therapy (ADEPT): A review," Adv. Drg. Del. Rev., Jul. 7, 1997, 26(2-3):151-172.
Nikula, Kristen et al., Animal Models of Chronic Bronchitis and Their Relevance to Studies of Particle-Induced Disease, Inhal. Toxicol. 4(12): 123-153, 2000.
Office Action issued in corresponding Taiwan patent application No. 103131876, dated Dec. 26, 2016, 7 pages.
Orlandi et al., "Cloning immunoglobulin variable domains for expression by the polymerase chain reaction," Proc. Natl. Acad. Sci. U.S.A., May 1989, 86(10):3833-3837.
Ørum et al., "Efficient method for constructing comprehensive murine Fab antibody libraries displayed on phage." Nucleic Acids Res., Sep. 25, 1993, 21(19):4491-4498.
Oxenius, Annette, et al. "CpG-containing oligonucleotides are efficient adjuvants for induction of protective antiviral immune responses with T-cell peptide vaccines." Journal of Virology 73.5 (1999): 4120-4126.
Papanastassiou et al., "The potential for efficacy of the modified (ICP 34.5-) herpes simplex virus HSV1716 following intratumoural injection into human malignant glioma: a proof of principle study," Gene Therapy, Mar. 2002, 9(6):398-406.
Paul, William E. "Structure and Function of Immunoglobulins, Fundamental Immunology." Chapter 9 (1993), 3rd Edition: 292-295.
Pearson, William, Using the FASTA Program to Search Protein and DNA Sequence Databases, Methods Mol. Biol. 243:307-331, 1994.
Pegram, Mark et al., Inhibitory Effects of Combinations of HER-2/neu Antibody and Chemotherapeutic Agents Used for Treatment of Human Breast Cancers, Oncogene 18:2241-2251, 1999.
Pegram, Mark et al., Rational Combinations of Trastuzumab With Chemotherapeutic Drugs Used in the Treatment of Breast Cancer, J. of the Nat. Cancer Inst. 96(10):739-749, 2004.
Plückthun, "Mono- and bivalent antibody fragments produced in *Escherichia coli*: Engineering, folding and antigen binding," Immunol. Rev., Dec. 1992, 130:151-188.
Plückthun, Handbook of Experimental Pharmacology, vol. 113: The Pharmacology of Monoclonal Antibodies, Chapter 11: Antibodies from *Escherichia coli*, Rosenberg et al., eds., 1994, pp. 269-315, Springer-Verlag, Berlin.
Presta et al., "Humanization of an antibody directed against IgE," J. Immunol., Sep. 1, 1993, 151(5):2623-2632.
Presta et al., "Humanization of an anti-vascular endothelial growth factor monoclonal antibody for the therapy of solid tumors and other disorders," Cancer Res., Oct. 15, 1997, 57(20):4593-4599.
Presta, Leonard G. "Antibody engineering." Current Opinion in Biotechnology 3.4 (1992): 394-398.

(56) References Cited

OTHER PUBLICATIONS

Presta, "Antibody engineering," Curr. Opin. Str. Biol., Aug. 1992, 2(4):593-596.
Proba et al., "Functional antibody single-chain fragments from the cytoplasm of *Escherichia coli*: influence of thioredoxin reductase (TrxB)," Gene, Jul. 4, 1995, 159(2):203-207.
Queen, Cary et al., A Humanized Antibody that Binds to the Interleukin 2 Receptor, Proc Natl Acad Sci., 86: 10029-10033 (1989).
Ragupathi, Govindaswami, et al. "Constructing an adenocarcinoma vaccine: Immunization of mice with synthetic KH-1 nonasaccharide stimulates anti-KH-1 and anti-Le$^y$ antibodies." International Journal of Cancer 99.2 (2002): 207-212.
Ramm et al., "The periplasmic *Escherichia coli* peptidylprolyl cis,trans-isomerase FkpA. II. Isomerase-independent chaperone activity in vitro," J. Biol. Chem., Jun. 2, 2000, 275(22):17106-17113.
Ravetch et al., "Fc receptors," Annu. Rev. Immunol., 1991, 9:457-492.
Reyes et al., "Expression of human β-interferon cDNA under the control of a thymidine kinase promoter from herpes simplex virus," Nature, Jun. 17, 1982, 297(5867):598-601.
Riechmann et al., "Reshaping human antibodies for therapy," Nature, Mar. 24, 1988, 332(6162):323-327.
Rowland et al., "Drug localisation and growth inhibition studies of vindesine-monoclonal anti-CEA conjugates in a human tumour xenograft," Cancer Immunol. Immunother., 1986, 21(3):183-187.
Rudikoff, Stuart, et al. "Single amino acid substitution altering antigen-binding specificity." Proceedings of the National Academy of Sciences 79.6 (1982): 1979-1983.
Sastry et al., "Cloning of the immunological repertoire in *Escherichia coli* for generation of monoclonal catalytic antibodies: construction of a heavy chain variable region-specific cDNA library," Proc. Natl. Acad. Sci. U.S.A., Aug. 1989, 86(15):5728-5732.
Schier et al., "Identification of functional and structural amino-acid residues by parsimonious mutagenesis," Gene, Mar. 9, 1996, 169(2):147-155.
Schiffman, Mark, and Philip E. Castle. "The promise of global cervical-cancer prevention." New England Journal of Medicine 353.20 (2005): 2101-2104.
Schwarz, Mikael, et al. "A new kind of carbohydrate array, its use for profiling antiglycan antibodies, and the discovery of a novel human cellulose-binding antibody." Glycobiology 13.11 (2003): 749-754.
Search Report issued in corresponding Taiwan patent application No. 103131876, dated Dec. 20, 2016, 1 page.
Sedlik, Christine et al., Effective Antitumor Therapy Based on a Novel Antibody-Drug Conjugate Targeting the Tn Carbohydrate Antigen, Oncoimmunology, Jul. 2016, vol. 5, No. 7, e1171434-1-13.
Shalaby et al., "Development of humanized bispecific antibodies reactive with cytotoxic lymphocytes and tumor cells overexpressing the *HER2* protooncogene," J. Exp. Med., Jan. 1, 1992, 175(1):217-225.
Sidhu et al., "Phage-displayed antibody libraries of synthetic heavy chain complementarity determining regions," J. Mol. Biol., Apr. 23, 2004, 338(2):299-310.
Siebenlist et al., "*E. coli* RNA polymerase interacts homologously with two different promoters," Cell, Jun. 1980, 20(2):269-281.
Sigma-Aldrich, Product Information for Hemocyanin From Megathura Crenulata, Catalog No. H7017, 1 Page, 2016.
Simmons et al., "Expression of full-length immunoglobulins in *Escherichia coli*: Rapid and efficient production of aglycosylated antibodies," J. Immunol. Methods, May 1, 2002, 263(1-2):133-147.
Sims et al., "A humanized CD18 antibody can block function without cell destruction," J. Immunol., Aug. 15, 1993, 151(4):2296-2308.
Sjölander, A., et al. "ISCOMs: an adjuvant with multiple functions." J. Leukocyte Biol. 64.6 (1998): 713-723.
Skerra, "Bacterial expression of immunoglobulin fragments," Curr. Opinion in Immunol., Apr. 1993, 5(2):256-262.
Sonderstrup, Grete, Development of Humanized Mice as a Model of Inflammatory Arthritis, Springer Sem. Immunopathol. 25: 35-45, 2003.
Speed, Margaret A., Daniel IC Wang, and Jonathan King. "Multimeric intermediates in the pathway to the aggregated inclusion body state for P22 tailspike polypeptide chains." Protein Science 4.5 (1995): 900-908.
Sun, Hongfan, Kevin GJ Pollock, and James M. Brewer. "Analysis of the role of vaccine adjuvants in modulating dendritic cell activation and antigen presentation in vitro." Vaccine 21.9-10 (2003): 849-855.
Suresh et al., "Bispecific monoclonal antibodies from hybrid hybridomas," Methods in Enzymology, 1986, 121:210-228.
Syrigos et al., "Antibody directed enzyme prodrug therapy (ADEPT): a review of the experimental and clinical considerations," Anticancer Research, Jan.-Feb. 1999, 19(1A):605-614.
Takeda et al., "Construction of chimaeric processed immunoglobulin genes containing mouse variable and human constant region sequences," Nature, Apr. 4-10, 1985, 314(6010):452-454.
Thorpe, (1985) "Antibody Carriers of Cytotoxic Agents in Cancer Therapy: A Review," in Monoclonal Antibodies '84: Biological and Clinical Applications, A. Pinchera et al. (Ed.s), pp. 475-506.
Tomlinson, I.M. et al., "The repertoire of human germline $V_H$ sequences reveals about fifty groups of $V_H$ segments with different hypervariable loops" J. Mol. Biol., Oct. 5, 1992, 227(3): 776-798.
Traunecker et al., "Bispecific single chain molecules (Janusins) target cytotoxic lymphocytes on HIV infected cells," EMBO J., Dec. 1991, 10(12):3655-3659.
Tutt et al., "Trispecific F(ab')$_3$ derivatives that use cooperative signaling via the TCR/CD3 complex and CD2 to activate and redirect resting cytotoxic T cells," J. Immunol., Jul. 1, 1991, 147(1):60-69.
Urlaub et al., "Isolation of Chinese hamster cell mutants deficient in dihydrofolate reductase activity." Proc. Natl. Acad. Sci. U.S.A., Jul. 1980, 77(7):4216-4220.
Vajdos, Felix F., et al. "Comprehensive functional maps of the antigen-binding site of an anti-ErbB2 antibody obtained with shotgun scanning mutagenesis." Journal of Molecular Biology 320.2 (2002): 415-428.
Vaswani et al., "Humanized antibodies as potential therapeutic drugs," Ann. Allergy, Asthma Immunol., Aug. 1998, 81(2):105-116, 119.
Verhoeyen et al., "Reshaping human antibodies: grafting an antilysozyme activity," Science, Mar. 25, 1988, 239(4847):1534-1536.
Wakimoto, Hiroaki, et al. "Intensified antitumor immunity by a cancer vaccine that produces granulocyte-macrophage colony-stimulating factor plus interleukin 4." Cancer Research 56.8 (1996): 1828-1833.
Wallner, Fredrik K., et al. "Solid-phase synthesis of serine-based glycosphingolipid analogues for preparation of glycoconjugate arrays." Organic & Biomolecular Chemistry 3.2 (2005): 309-315.
Wang et al., "Glycan microarray of Globo H and related structures for quantitative analysis of breast cancer," Proc. Natl. Acad. Sci. U.S.A., Aug. 19, 2008, 105(33):11661-11666.
Ward et al., "Binding activities of a repertoire of single immunoglobulin variable domains secreted from *Escherichia coli*," Nature, Oct. 12, 1989, 341(6242):544-546.
Waterhouse et al., "Combinatorial infection and in vivo recombination: a strategy for making large phage antibody repertoires," Nuc. Acids Res., May 11, 1993, 21(9):2265-2266.
Wilen et al., "Strategies in optical resolutions," Tetrahedron, 1977, 33(21):2725-2736.
Williams, S.C. and Winter, G. "Cloning and sequencing of human immunoglobulin $V_\lambda$ gene segments" Eur. J. Immunol., 1993, 23: 1456-1461.
Wilman, "Prodrugs in Cancer Chemotherapy" Biochemical Society Transactions, 14, pp. 375-382, 615th Meeting Belfast, 1986.
Winter et al., "Making antibodies by phage display technology," Annu. Rev. Immunol., 1994, 12:433-455.
Wymer, Nathan et al., Enzyme-Catalyzed Synthesis of Carbohydrates, Curr. Opin. Chem. Biol., 4, 110-119, 2000.
Yaniv, Moshe, Enhancing Elements for Activation of Eukaryotic Promoters, Nature 297: 17-18, 1982.

(56) References Cited

OTHER PUBLICATIONS

Yansura et al., "Nucleotide sequence selection for increased expression of heterologous genes in *Escherichia coli*," Methods: A Companion to Methods in Enzymol., Aug. 1992, 4(2):151-158.
Yelton et al., "Affinity maturation of the BR96 anti-carcinoma antibody by codon-based mutagenesis." J. Immunol., Aug. 15, 1995, 155(4):1994-2004.
Zhang et al., "Selection of tumor antigens as targets for immune attack using immunohistochemistry: I. Focus on gangliosides," Int. J. Cancer, Sep. 26, 1997,73(1):42-49.
Zhu, Jianglong et al., From Synthesis to Biologics: Preclinical Data on a Chemistry Derived Anticancer Vaccine.
Eller, Chelcie et al., "Affinity of monoclonal antibodies for Globo-series glycans," Carbohydrate Research, (2014), 397, 1-6.
Lou, Yi-Wei et al., "Stage-specific embryonic antigen-4 as a potential therapeutic target in glioblastoma multiforme and other cancers," PNAS, (2014), 111(7): 2482-2487.
Sasikumar et al., "Small-Molecule Immune Checkpoint INhibitors Targeting PD-1/PD-L1 and Other Emerging Checkpoint Pathways," BioDrugs, 2018, 32:481-497.
BLAST alignment of GenBank AN126084.1 and SEQ ID No. 1 (downloaded Nov. 20, 2020). (Year: 2020).
Final Office Action issued in U.S. Appl. No. 16/454,750 dated May 27, 2021.
First Examination Report dated Jul. 5, 2021 in India Patent Application No. 201717013151.
Gebauer, J Structrual Biology, vol. 128, p. 280-286, 1999.
Non-Final Office Action issued in U.S. Appl. No. 14/855,260 dated Jul. 27, 2021.
Substantive Examination Report, Office Paper No. 7, issued in Philippines Application No. 1-2017-500478 dated Oct. 21, 2020.
Substantive Examination Report, Office Paper No. 9, issued in Philippines Application No. 1-2017-500478 dated Jun. 10, 2021.
International Search Report dated Mar. 24, 2022, in International Patent Publication No. WO 2022/072513.
Lin, Yuan et al., "Improved affinity of a chicken single-chain antibody to avian infectious bronchitis virus by site-directed mutagenesis of complementarity-determining region H3", African Journal of Biotechnology, vol. 10(79), pp. 18294-18302, Dec. 12, 2011.
Mariuzza, R.A. et al., "The Structural Basis of Antigen-Antibody Recognition", Ann. Rev. Biophys. Chem, 1987, vol. 16, pp. 139-159.
McCarthy, Barry J., et al. "Altering the find specificity of an anti-Legionella single chain antibody by a single amino acid insertion", Journal of Immunological Methods, 2001, vol. 251, pp. 137-149.
NCT01516307—Trial of Active Immunotherapy with Globo H-KLH (OPT-822) in Metastatic Breast Cancer Subjects. Full Text Review. ClinicalTrials.gov. Jan. 2012 (https://clinicaltrials.gov/ct2/show/NCT01516307).
Ragupathi, G., et al., "A fully synthetic globo H carbohydrate vaccine induces a focused humoral response in prostate cancer patients: a proof of principle," Angewandte Chemie International Edition 38.4 (1999): 569-566. Feb. 24, 1999.
Wang, Z.-G. et al., "Polyclonal antibodies from patients immunized with a globo H-keyhole limpet hemocyanin vaccine: Isolation, quantification, and characterization of immune responses by using totally synthetic immobilized tumor antigens," PNAS, Mar. 14, 2000, vol. 97, No. 6, pp. 2719-2724.
Chang, W.W. et al., "Expression of Globo H and SSEA3 in breast cancer stem cells and the involvement of fucosyl transferases 1 and 2 in Globo H synthesis," PNAS, Aug. 19, 2008, vol. 105 No. 33, pp. 11667-11672.
GENBANK: CAG28308.1, May 13, 2004.
GENBANK: CAG28309.2, Nov. 26, 2013.
Pravetoni, M et al. "Structurally distinct nicotine immunogens elicit antibodies with non-overlapping specificities," Biochem Pharmacol, Feb. 15, 2012, vol. 83. No. 4, 543-550. 19 pages.
Sledzinska, Anna et al. "Negative immune checkpoints on T lymphocytes and their relevance to cancer immunotherapy," Molecular Oncology, 2015, vol. 9, pp. 1936-1965 (30 pages).

\* cited by examiner

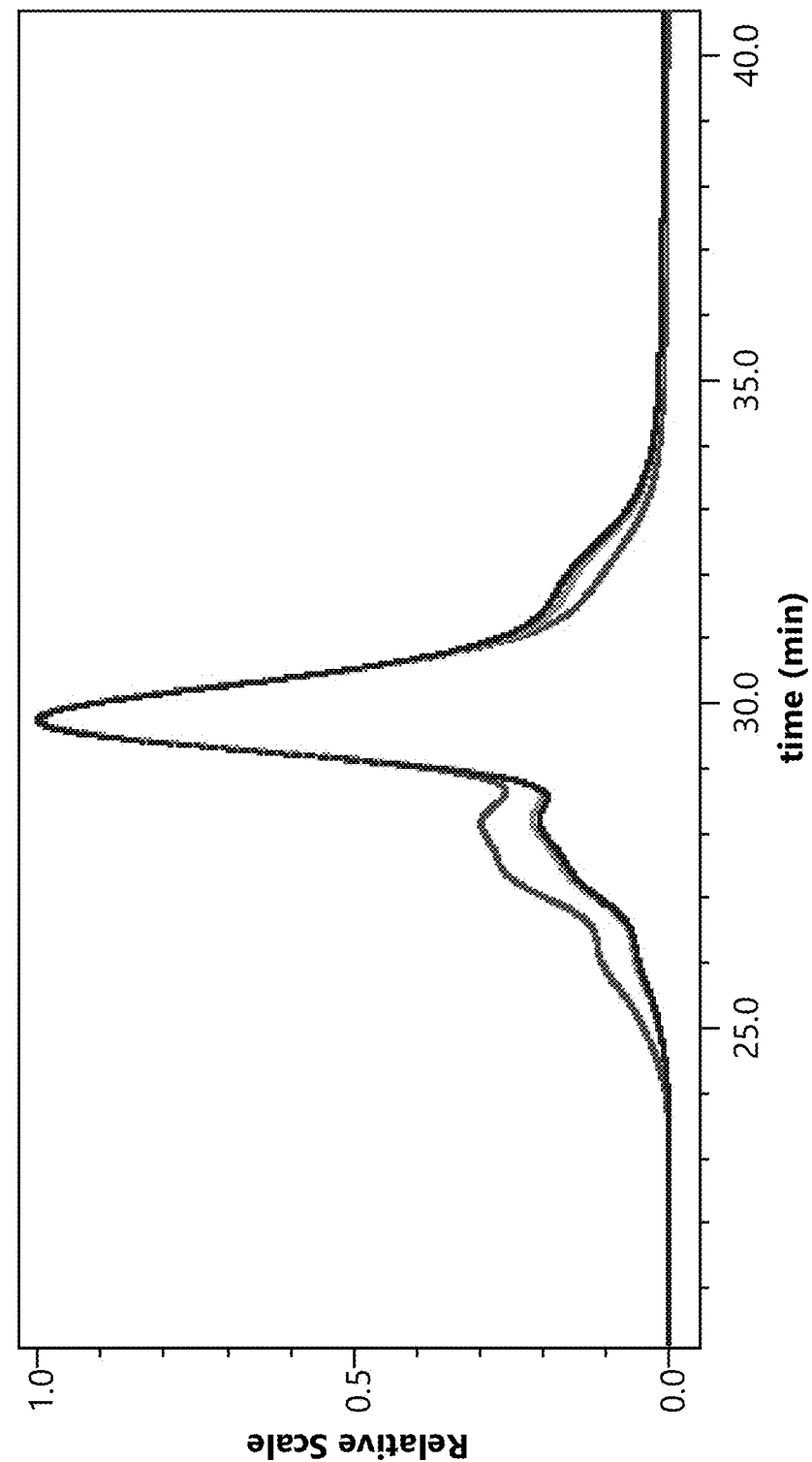

Distribution Analysis

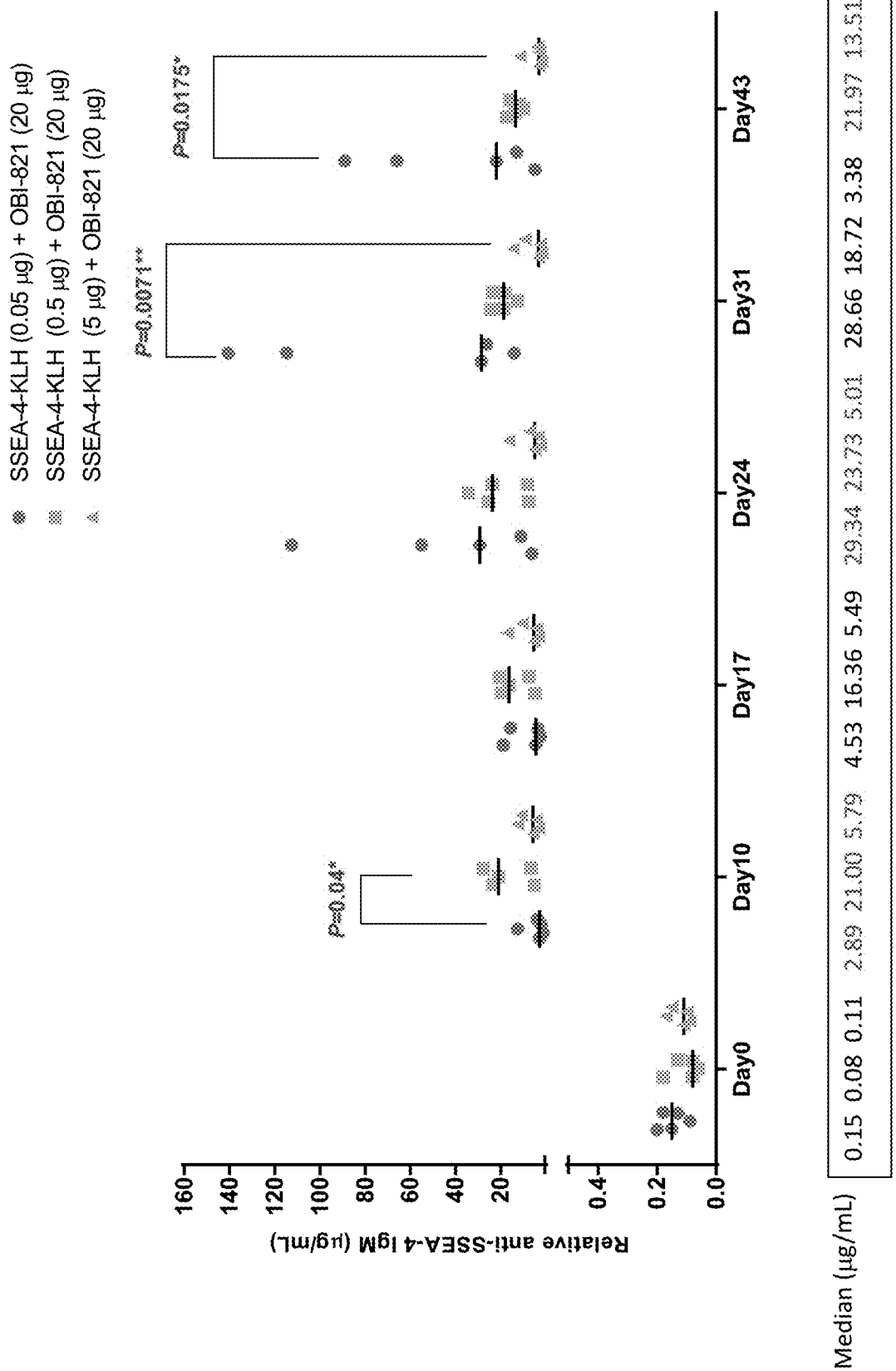

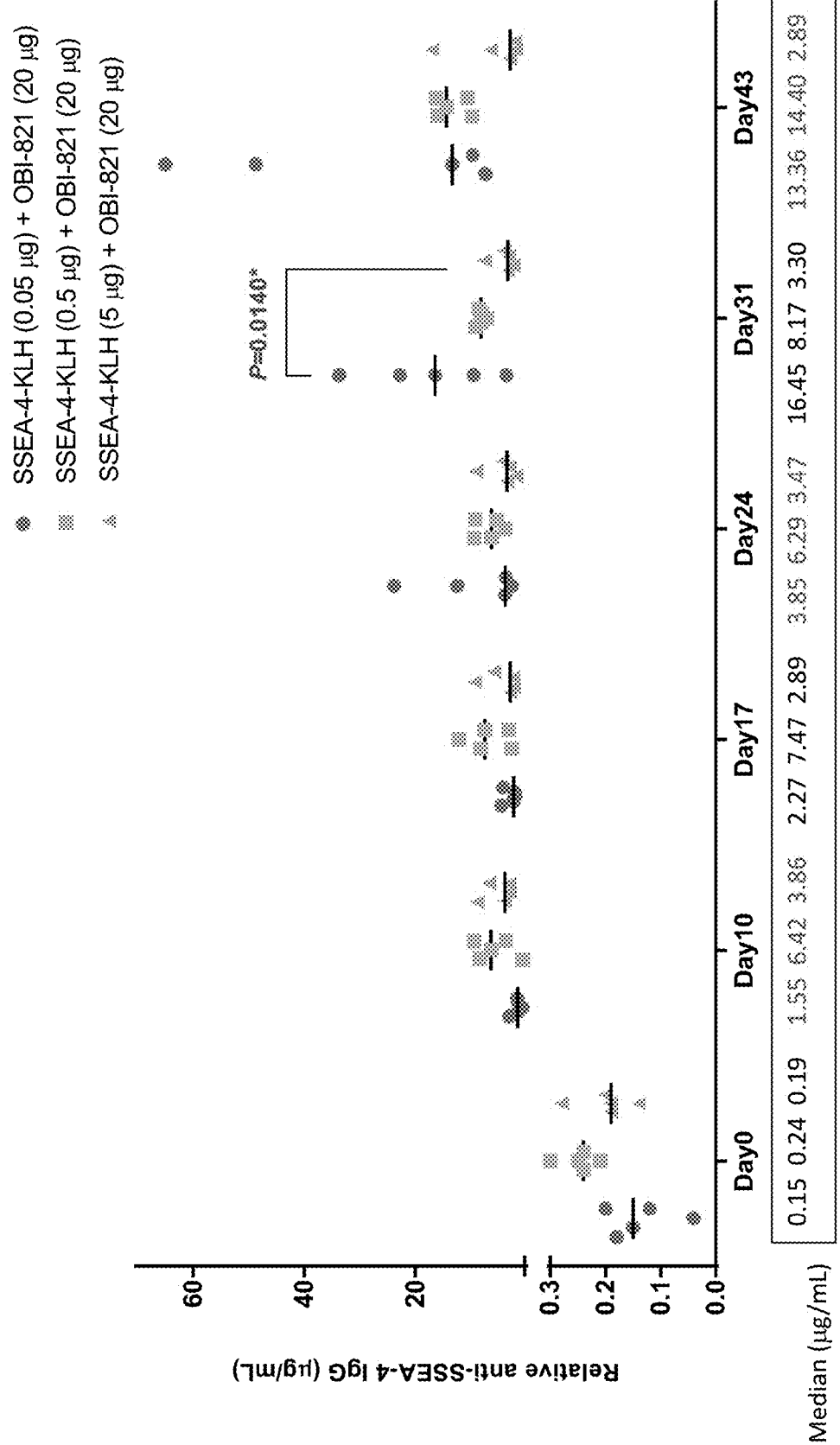

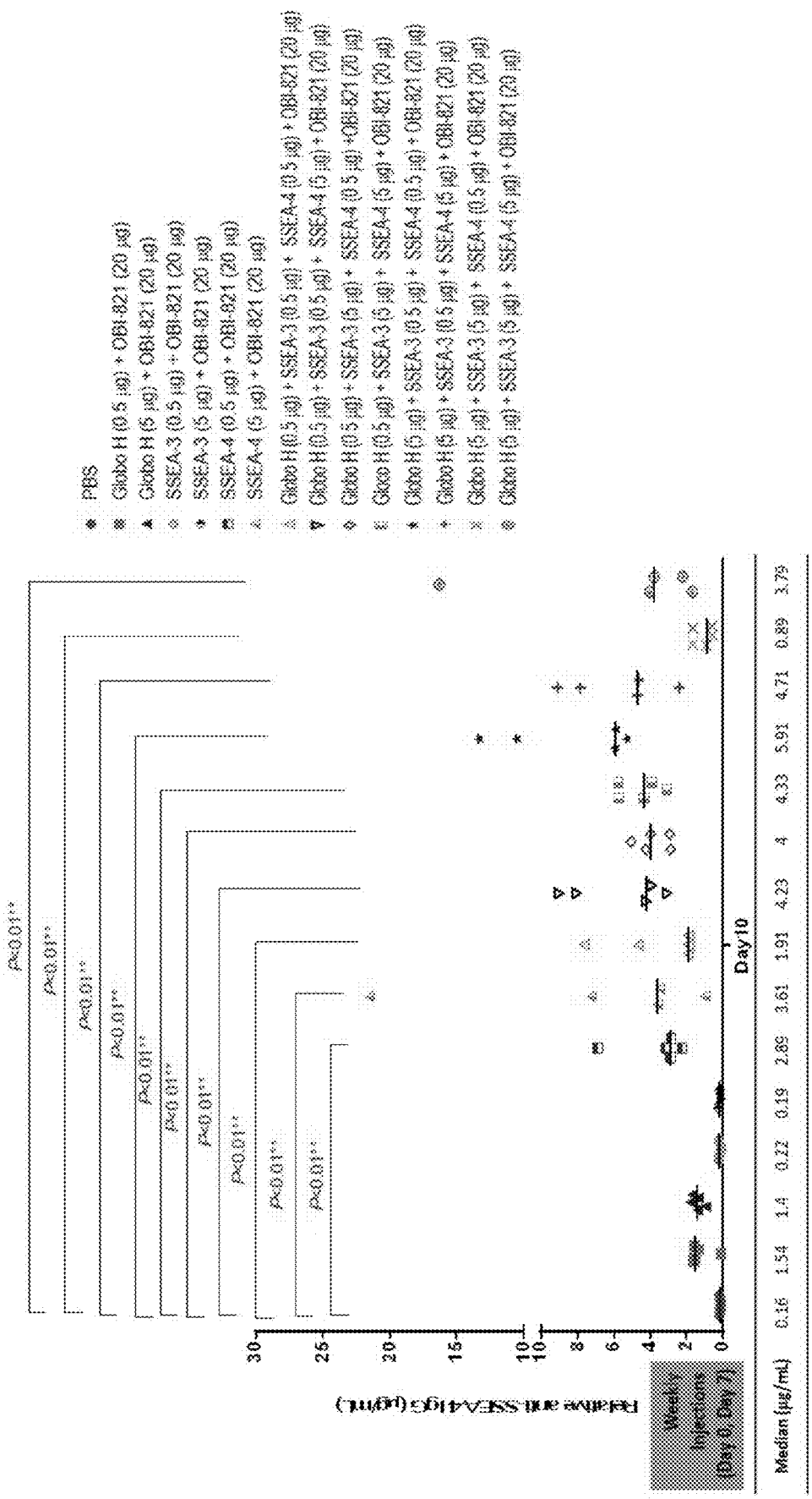

IMMUNOGENIC/THERAPEUTIC GLYCAN COMPOSITIONS AND USES THEREOF

CROSS-REFERENCE TO RELATED APPLICATIONS

This application claims the priority of U.S. Provisional Patent Application No. 62/367,528, filed Jul. 27, 2016. The entirety of the aforementioned application is incorporated herein by reference.

FIELD OF THE INVENTION

The present disclosure is directed to compositions and methods for cancer immunotherapy and immunogenic/therapeutic glycoconjugates able to elicit anti-cancer immune responses in particular.

BACKGROUND

Numerous surface carbohydrates are expressed in malignant tumor cells. For example, Globo H (Fucα1→2 Galβ1→3 GalNAcβ1→3 Galα1→4 Galβ1→4 Glc) has been shown to overexpress on a variety of epithelial cancers and is associated with tumor aggressiveness and poor prognosis in breast cancer and small cell lung carcinoma. Previous studies have shown that Globo H and Stage-specific embryonic antigen 3 (SSEA-3, also called Gb5) (Galβ1→3GalNAcβ1→3Galα1→4Galβ1→4Glcβ1) were observed on breast cancer cells and breast cancer stem cells (W W Chang et al. "Expression of Globo H and SSEA-3 in breast cancer stem cells and the involvement of fucosyl transferases 1 and 2 in Globo H synthesis." PNAS, 105(33): 11667-11672, 2008). SSEA-4 (stage-specific embryonic antigen-4), a hexasaccharide (Neu5Acα2→3Galβ1→3GalNAcβ1→3Galα1→4Galβ1→4Glcβ1), has been commonly used as a cell surface marker for pluripotent human embryonic stem cells and has been used to isolate mesenchymal stem cells and enrich neural progenitor cells (Kannagi R et al. EMBO J, 2:2355-2361, 1983). Previous study has shown that stage-specific embryonic antigen-4 (SSEA-4) could serve as a potential therapeutic target in glioblastoma multiforme and other cancers (W W Chang et al. PNAS, 111(7): 2482-2487, 2014).

SUMMARY OF THE INVENTION

As disclosed here, it was recognized that Globo series antigens (Globo H, SSEA-3 and SSEA-4) are unique targeting for cancer cells and can take therapeutic agents to targeting cancer cells effectively.

Accordingly, the present disclosure generally encompasses therapeutic and/or prophylactic compositions including Globo series antigens (SSEA-4, Globo H and SSEA-3), as well as, immunotherapeutics, vaccines, dosage forms, kits, and methods of manufacture, and treatment thereof.

In one embodiment, the invention encompasses an isolated therapeutic conjugate comprising a Globo series antigen (SSEA-4, Globo H or SSEA-3) moiety covalently linked to a carrier moiety, e.g., a keyhole limpet hemocyanin (KLH) or diphtheria toxin cross-reacting material 197 (DT-CRM 197) moiety subunit via p-nitrophenyl linker, 4-(4-N-maleimidomethyl) cyclohexane-1-carboxyl hydrazide (MMCCH) linker or 4-(N-Maleimidomethyl)-cyclohexane-1-carboxylate (MCCa) linker.

In another illustrative embodiment, the invention encompasses an isolated immunogenic/therapeutic conjugate having the following general structure:

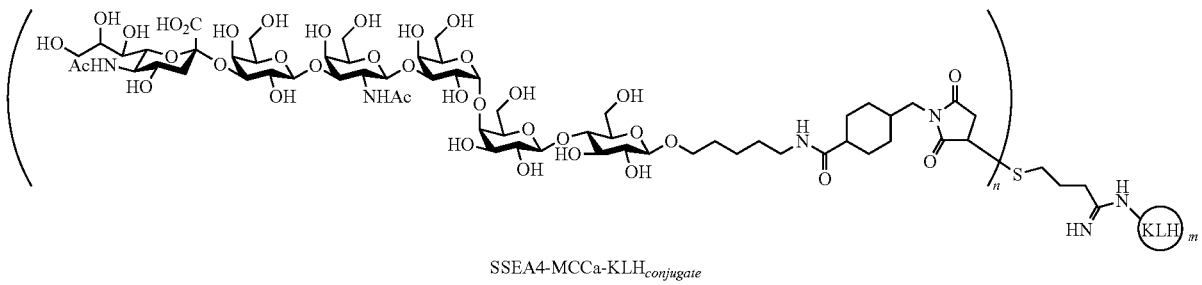

SSEA4-MCCa-KLH$_{conjugate}$ wherein n is independently an integer from about 1 to about 3000 and m is independently an integer from about 1 to about 20. In certain embodiments, when m is greater than 1, KLH moieties can aggregate to form multimeric structures. In certain embodiments, the aggregation is a covalent bond. In certain other embodiments, the aggregation is not a covalent bond (e.g., the aggregation is formed by H-bonding or hydrophobic interactions). In certain embodiments, a monomeric KLH moiety (i.e., where m=1) can include from about 1 to about 150 SSEA-4 moieties. In certain embodiments, a dimeric KLH moiety (i.e., where m=2) can include from about 1 to about 300 SSEA-4 moieties. In certain embodiments, a trimeric KLH moiety (i.e., where m=3) can include from about 1 to about 450 SSEA-4 moieties. In certain embodiments, a tetrameric KLH moiety (i.e., where m=4) can include from about 1 to about 600 SSEA-4 moieties. In certain embodiments, a pentameric KLH moiety (i.e., where m=5) can include from about 1 to about 750 SSEA-4 moieties. In certain embodiments, a hexameric KLH moiety (i.e., where m=6) can include from about 1 to about 900 SSEA-4 moieties. In certain embodiments, a didecameric KLH moiety (i.e., where m=20) can include from about 1 to about 3000 SSEA-4 moieties.

In any of the aspects disclosed herein, the immunogenic/therapeutic conjugate may comprise one or more DT-CRM 197 moieties, or any other suitable immunogenic moiety, or combination thereof.

In one embodiment, the SSEA-4 moiety comprises (Neu5Acα2→3Galβ1→3GalNAcβ1→3Galα1→4Galβ1→4Glcβ1). In a further embodiment, the KLH moiety subunit is a KLH-1 or KLH-2 moiety or a combination thereof. As used herein, the term "KLH" refers to KLH-1, KLH-2, and/or combinations thereof.

In another illustrative embodiment, the invention encompasses an isolated immunogenic/therapeutic conjugate having the following general structure:

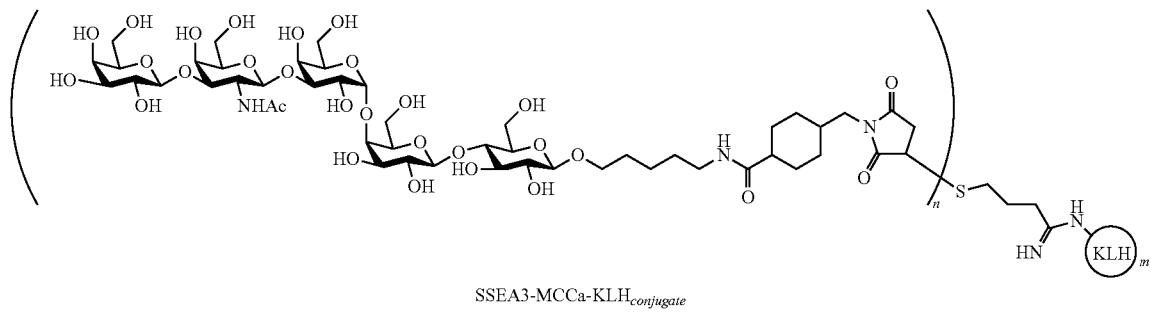

SSEA3-MCCa-KLH$_{conjugate}$ wherein n is independently an integer from about 1 to about 3000 and m is independently an integer from about 1 to about 20. In certain embodiments, when m is greater than 1, KLH moieties can aggregate to form multimeric structures. In certain embodiments, the aggregation is a covalent bond. In certain other embodiments, the aggregation is not a covalent bond (e.g., the aggregation is formed by H-bonding or hydrophobic interactions). In certain embodiments, a monomeric KLH moiety (i.e., where m=1) can include from about 1 to about 150 SSEA-3 moieties. In certain embodiments, a dimeric KLH moiety (i.e., where m=2) can include from about 1 to about 300 SSEA-3 moieties. In certain embodiments, a trimeric KLH moiety (i.e., where m=3) can include from about 1 to about 450 SSEA-3 moieties. In certain embodiments, a tetrameric KLH moiety (i.e., where m=4) can include from about 1 to about 600 SSEA-3 moieties. In certain embodiments, a pentameric KLH moiety (i.e., where m=5) can include from about 1 to about 750 SSEA-3 moieties. In certain embodiments, a hexameric KLH moiety (i.e., where m=6) can include from about 1 to about 900 SSEA-3 moieties. In certain embodiments, a didecameric KLH moiety (i.e., where m=20) can include from about 1 to about 3000 SSEA-3 moieties.

In one embodiment, the SSEA-3 moiety comprises (Galβ1→3GalNAcβ1→3Galα1→4Galβ1→4Glcβ1). In a further embodiment, the KLH moiety subunit is a KLH-1 or KLH-2 moiety or a combination thereof. As used herein, the term "KLH" refers to KLH-1, KLH-2, and/or combinations thereof.

In another illustrative embodiment, the invention encompasses an isolated immunogenic/therapeutic conjugate having the following general structure:

In certain embodiments, the aggregation is a covalent bond. In certain other embodiments, the aggregation is not a covalent bond (e.g., the aggregation is formed by H-bonding or hydrophobic interactions). In certain embodiments, a monomeric KLH moiety (i.e., where m=1) can include from about 1 to about 150 Globo H moieties. In certain embodiments, a dimeric KLH moiety (i.e., where m=2) can include from about 1 to about 300 Globo H moieties. In certain embodiments, a trimeric KLH moiety (i.e., where m=3) can include from about 1 to about 450 Globo H moieties. In certain embodiments, a tetrameric KLH moiety (i.e., where m=4) can include from about 1 to about 600 Globo H moieties. In certain embodiments, a pentameric KLH moiety (i.e., where m=5) can include from about 1 to about 750 Globo H moieties. In certain embodiments, a hexameric KLH moiety (i.e., where m=6) can include from about 1 to about 900 Globo H moieties. In certain embodiments, a didecameric KLH moiety (i.e., where m=20) can include from about 1 to about 3000 Globo H moieties.

In one embodiment, the Globo H moiety comprises (Fucα1→2 Galβ1→3 GalNAcβ1→3 Galα1→4 Galβ1→4 Glc). In a further embodiment, the KLH moiety subunit is a KLH-1 or KLH-2 moiety or a combination thereof. As used herein, the term "KLH" refers to KLH-1, KLH-2, and/or combinations thereof.

Another embodiment of the invention encompasses a pharmaceutical composition comprising KLH moiety subunits, wherein each KLH moiety subunit comprises one or more Globo series antigens moieties covalently linked to a keyhole limpet hemocyanin (KLH) moiety subunit. In certain embodiments, the pharmaceutical composition comprises dimers of at least two KLH moiety subunits, wherein

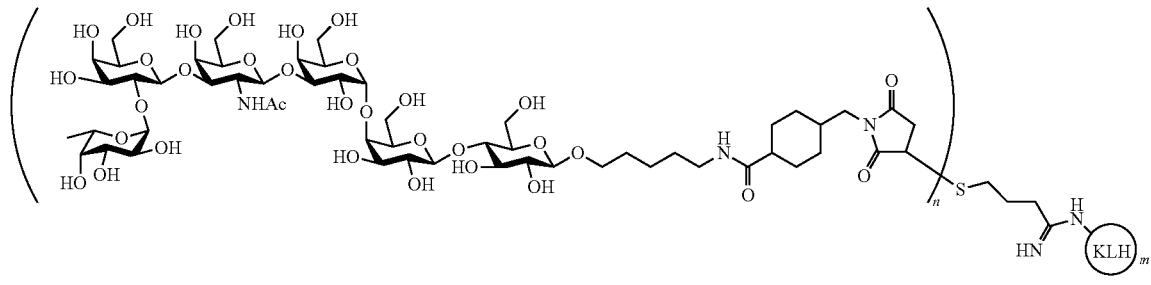

Globo H-MCCa-KLH$_{conjugate}$ wherein n is independently an integer from about 1 to about 3000 and m is independently an integer from about 1 to about 20. In certain embodiments, when m is greater than 1, KLH moieties can aggregate to form multimeric structures.

each KLH moiety subunits comprises one or more Globo series antigens moieties covalently linked to a KLH moiety subunit. In certain embodiments, the pharmaceutical composition comprises trimers of at least three KLH moiety subunits, wherein each KLH moiety subunits comprises one or more Globo series antigens moieties covalently linked to a KLH moiety subunit. In certain embodiments, the pharmaceutical composition comprises at least four KLH moiety subunits, wherein each KLH moiety subunit comprises one or more Globo series antigens moieties covalently linked to a KLH moiety subunit. In certain embodiments, the pharmaceutical composition comprises a mixture of KLH moiety subunits (e.g., monomers, dimers, trimers, tetramers, pentamers, hexamers etc.), wherein each KLH moiety subunits comprises multiple Globo series antigens moieties covalently linked to a KLH moiety subunit.

In certain embodiments, certain exemplary composition embodiments and methods of use thereof can include or exclude (e.g. proviso out) any one or more of the other representative compound and/or composition embodiments described herein.

In another embodiment, the pharmaceutical composition comprises an adjuvant. As used herein, the terms "immunologic adjuvant" refers to a substance used in conjunction with an immunogen which enhances or modifies the immune response to the immunogen. Specifically, the terms "adjuvant" and "immunoadjuvant" are used interchangeably in the present invention and refer to a compound or mixture that may be non-immunogenic when administered to a host alone, but that augments the host's immune response to another antigen when administered conjointly with that antigen. Adjuvant-mediated enhancement and/or extension of the duration of the immune response can be assessed by any method known in the art including without limitation one or more of the following: (i) an increase in the number of antibodies produced in response to immunization with the adjuvant/antigen combination versus those produced in response to immunization with the antigen alone; (ii) an increase in the number of T cells recognizing the antigen or the adjuvant; and (iii) an increase in the level of one or more Type I cytokines.

The adjuvant of can be administered as part of a pharmaceutical or vaccine composition comprising an antigen or as a separate formulation, which is administered conjointly with a second composition containing an antigen. In any of these compositions glycosphingolipids (GSLs) can be combined with other adjuvants and/or excipients/carriers. These other adjuvants include, but are not limited to, oil-emulsion and emulsifier-based adjuvants such as complete Freund's adjuvant, incomplete Freund's adjuvant, MF59, or SAF; mineral gels such as aluminum hydroxide (alum), aluminum phosphate or calcium phosphate; microbially-derived adjuvants such as cholera toxin (CT), pertussis toxin, *Escherichia coli* heat-labile toxin (LT), mutant toxins (e.g., LTK63 or LTR72), Bacille Calmette-Guerin (BCG), *Corynebacterium parvum*, DNA CpG motifs, muramyl dipeptide, or monophosphoryl lipid A; particulate adjuvants such as immunostimulatory complexes (ISCOMs), liposomes, biodegradable microspheres, or saponins (e.g., QS-21); cytokines such as IFN-γ, IL-2, IL-12 or GM-CSF; synthetic adjuvants such as nonionic block copolymers, muramyl peptide analogues (e.g., N-acetyl-muramyl-L-threonyl-D-isoglutamine [thr-MDP], N-acetyl-nor-muramyl-L-alanyl-D-isoglutamine, N-acetylmuramyl-L-alanyl-D-isoglutaminyl-L-alanine-2-[1'-2'-dipalmitoyl-sn-glycero-3-hydroxyphosphoryloxy]-ethylamine), polyphosphazenes, or synthetic polynucleotides, and surface active substances such as lysolecithin, pluronic polyols, polyanions, peptides, hydrocarbon emulsions, or keyhole limpet hemocyanins (KLH), Toll-Like Receptor molecules, LPS, lipoproteins, lipopeptides, flagellin, double-stranded RNA, viral DNA, unmethylated CpG islands, levamisole, bacillus Calmette-Guerin, Isoprinosine, Zadaxin, PD-1 antagonists, PD-1 antibodies, CTLA antagonists, CTLA antibodies, interleukin, cytokines, GM-CSF, glycolipid, aluminum salt based, aluminum phosphate, alum, aluminum hydroxide, liposomes, TLR2 agonists, lipopeptide, nanoparticles, monophosphoryl lipid A, OBI-821 adjuvant, saponin, OBI-834 adjuvant, C34 adjuvant, oil in water nano-emulsions, and bacteria-like particle. Preferably, these additional adjuvants are also pharmaceutically acceptable for use in humans.

In another embodiment, the pharmaceutical composition comprises a cytokine selected from the group consisting of IL-2, IL-12, IL-18, IL-2, IFN-γ, TNF, IL-4, IL-10, IL-13, IL-21, GM-CSF and TGF-β. In a further embodiment, the pharmaceutical composition comprises a chemokine.

In a further embodiment, the immunogenic/therapeutic agent is administered as a pharmaceutical composition.

In still another embodiment, the pharmaceutical composition comprises monoclonal antibodies, chemotherapeutics, hormonal therapeutic agents, retinoid receptor modulators, cytotoxic/cytostatic agents, antineoplastic agents, antiproliferative agents, anti-mTOR agents, anti-Her2 agents, anti-EGFR agents, prenyl-protein transferase inhibitors, HMG-CoA reductase inhibitors, nitrogen mustards, nitroso ureas, angiogenesis inhibitors, bevacizumab, inhibitors of cell proliferation and survival signaling pathway, apoptosis inducing agents, agents that interfere with cell cycle checkpoints, agents that interfere with receptor tyrosine kinases (RTKs), integrin blockers, NSAIDs, PPAR agonists, inhibitors of inherent multidrug resistance (MDR), anti-emetic agents, agents useful in the treatment of anemia, agents useful in the treatment of neutropenia, immunologic-enhancing drugs, biphosphonates, aromatase inhibitors, agents inducing terminal differentiation of neoplastic cells, γ-secretase inhibitors, cancer vaccines (e.g., active immunotherapy), monoclonal antibody therapeutics (e.g., passive immunotherapy), and any combination thereof.

In another embodiment, the therapeutic compositions of the invention can further comprise PD-1/PD-L1 inhibitors (cytotoxic T cell lymphocyte (CTLs) immunotherapy), CTLA-4 immunotherapy, CDK4/6 inhibitors (target therapy), PI3K inhibitors (target therapy), mTOR inhibitors (target therapy), AKT inhibitors (target therapy), Pan-Her inhibitors (target therapy). These inhibitors can be modified to generate the respective monoclonal antibody as well. Such antibodies can be included in therapeutic compositions of the invention.

In another embodiment, the pharmaceutical composition comprises a pharmaceutically acceptable carrier. In a further embodiment, the pharmaceutical composition is a cancer vaccine. In still another embodiment, the pharmaceutical composition is formulated for subcutaneous administration. In still another embodiment, the pharmaceutical composition is formulated for intramuscular administration. In still another embodiment, the pharmaceutical composition is formulated for intra-arterial administration. In still another embodiment, the pharmaceutical composition is formulated for intravenous administration.

BRIEF DESCRIPTION OF THE FIGURES

The patent or application file contains at least one drawing executed in color. Copies of this patent or patent application publication with color drawing(s) will be provided by the Office upon request and payment of the necessary fee.

A more complete understanding of the invention may be obtained by reference to the accompanying drawings, when considered in conjunction with the subsequent detailed description. The embodiments illustrated in the drawings are intended only to exemplify the invention and should not be construed as limiting the invention to the illustrated embodiments.

FIG. 1A shows the result of size exclusion chromatography (SEC) of KLH using multi-angle laser scattering spectrometry (MALS) as detector.

FIG. 3A and FIG. 3B show the result of Anti-SSEA-4 IgM level and median concentration from five individual mouse induced by different doses of SSEA-4-KLH and SSEA-4-DT single valent vaccine with OBI-821 adjuvant. FIG. 3C and FIG. 3D show the result of Anti-SSEA-4 IgG levels induced by different doses of SSEA-4-KLH and SSEA-4-DT single valent vaccine with OBI-821 adjuvant.

FIG. 5A shows the result Anti-Globo H IgM levels, FIG. 5B shows the result Anti-SSEA-3 IgM levels and FIG. 5C shows the result Anti-SSEA-4 IgM levels. FIG. 5D shows the result Anti-Globo H IgG levels. FIG. 5E shows the result Anti-SSEA-3 IgG levels and FIG. 5F shows the result Anti-SSEA-4 IgG levels.

FIGS. 6A through 6D show the immunogenicity result induced by tri-valent vaccine (SSEA-4-KLH+Globo H-KLH+SSEA-3-KLH glycoconjugate) with OBI-821 adjuvant. FIG. 6A shows the result Anti-Globo H IgM levels and FIG. 6B shows the result Anti-SSEA-4 IgM levels. FIG. 6C shows the result Anti-Globo H IgG levels and FIG. 6D shows the result Anti-SSEA-4 IgG levels.

DETAILED DESCRIPTION OF THE INVENTION

Figure 1B:
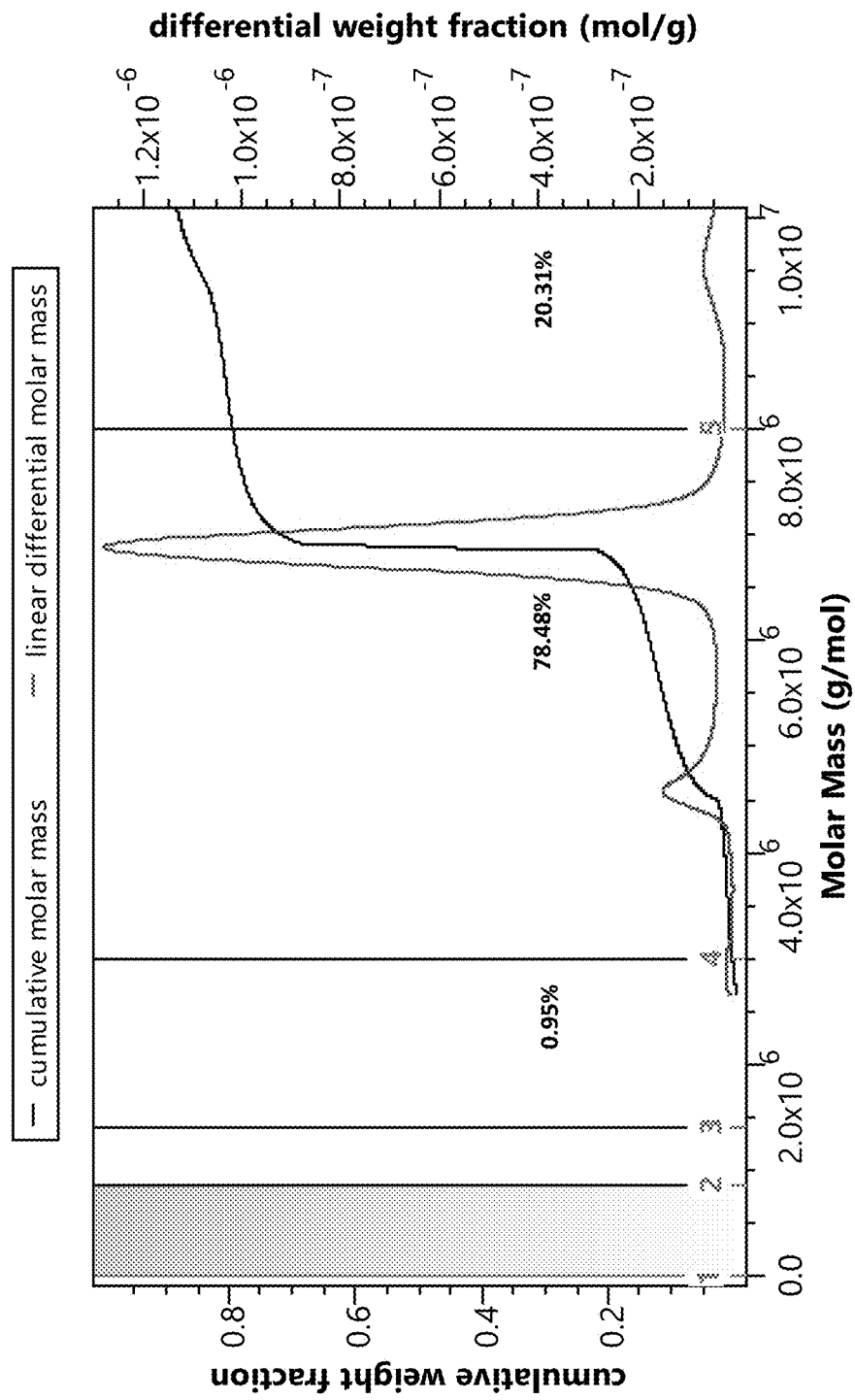
FIG. 1B shows the mass distribution analysis of KLH using SEC-MALS.

The practice of the present invention will employ, unless otherwise indicated, conventional techniques of molecular biology, microbiology, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Antibodies: A Laboratory Manual, by Harlow and Lanes (Cold Spring Harbor Laboratory Press, 1988); and Handbook Of Experimental Immunology, Volumes I-IV (D. M. Weir and C. C. Blackwell, eds., 1986).

The use of synthetic carbohydrate conjugates to elicit antibodies was first demonstrated by Goebel and Avery in 1929. (Goebel, W. F., and Avery, O. T., J. Exp. Med., 1929, 50, 521; Avery, O. T., and Goebel, W. F., J. Exp. Med., 1929, 50, 533.) Carbohydrates were linked to carrier proteins via the benzenediazonium glycosides. Immunization of rabbits with the synthetic antigens generated polyclonal antibodies. Other workers (Allen, P. Z., and Goldstein, I. J., Biochemistry, 1967, 6, 3029; Rude, E., and Delius, M. M., Carbohydr. Res., 1968, 8, 219; Himmelspach, K., et al., Eur. J. Immunol., 1971, 1, 106; Fielder, R. J., et al., J. Immunol., 1970, 105, 265) developed similar techniques for conjugation of carbohydrates to protein carriers.

Glycoconjugates may be used in active immunotherapy generated from vaccinations to specifically target known target agents on tumor cells. The response to carbohydrate antigens normally does not enlist the use of T-cells, which would aid in the body's rejection of the tumor. While the probability of complete tumor rejection as a result of vaccination with a conjugate is thought to be unlikely, such treatments will boost immune surveillance and recurrence of new tumor colonies can be reduced. (Dennis, J., Oxford Glycosystems Glyconews Second, 1992; Lloyd, K. O., in Specific Immunotherapy of Cancer with Vaccines, 1993, New York Academy of Sciences, 50-58). Toyokuni and Singhal have described a synthetic glycoconjugate (Toyokuni, T., et al., J. Am. Chem. Soc., 1994, 116, 395) that stimulated a measurable IgG titer, a result which is significant since an IgG response is generally associated with enlistment of helper T cells.

Accordingly, the present disclosure is directed to immunogenic/therapeutic compounds, compositions, and/or pharmaceutical formulation compositions targeted to/mediated by SSEA-4, as well as, immunotherapeutics, vaccines, dosage forms, kits, and methods of manufacture, and treatment thereof.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes for example, the inherent variation of error for a measuring device, the method being employed to determine the value, or the variation that exists among the study subjects. Typically, the term is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability depending on the situation.

As used herein, the term "alkyl" refers to a straight or branched monovalent hydrocarbon containing, unless otherwise stated, 1-20 carbon atoms, e.g., C1-C8 or C1-C4, which can be substituted or unsubstituted. Examples of alkyl include, but are not limited to, methyl, ethyl, n-propyl, i-propyl, n-butyl, i-butyl, and t-butyl.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrequired elements or method steps. It is contemplated that any embodiment discussed in this specification can be implemented with respect to any method or composition of the invention, and vice versa. Furthermore, compositions of the invention can be used to achieve methods of the invention.

"Treating" or "treating" is referred to herein as administration of a therapeutic composition to a subject with the purpose to cure, alleviate, relieve, remedy, prevent, or ameliorate a disorder, symptoms of the disorder, a disease state secondary to the disorder, or predisposition toward the disorder.

An "effective amount" is an amount of a therapeutic composition that is capable of producing a medically desirable result as delineated herein in a treated subject. The medically desirable result may be objective (i.e., measurable by some test or marker) or subjective (i.e., subject gives an indication of or feels an effect).

"Disease amenable to treatment with a therapeutic composition" as referred to herein means any procedures, conditions, disorders, ailments and/or illnesses which can be treated by the administration of the therapeutic compositions disclosed herein.

A "proliferative disorder" is one in which too many of some type of cell are produced resulting in deterioration of health. A proliferative disorder can be benign or malignant. Proliferative disorders can include for example, cancer.

As used herein, "cancer" that can be treated by the therapeutic compositions disclosed herein, includes cells with an abnormal growth state. Cancer cells can be characterized by loss of normal control mechanisms and thus are able to expand continuously, invade adjacent tissues, migrate to distant parts of the body, and promote the growth of new blood vessels from which the cells derive nutrients. As used herein, a cancer can be malignant or benign. Cancer can develop from any tissue within the body. As cells grow and multiply, they form a mass of tissue, called a tumor. The term tumor can include an abnormal growth or mass. Tumors can be cancerous (malignant) or noncancerous (benign). Cancerous tumors can invade neighboring tissues and spread throughout the body (metastasize). Benign tumors, however, generally do not invade neighboring tissues and do not spread throughout the body. Cancer can be divided into those of the blood and blood-forming tissues (leukemia and lymphoma) and "solid" tumors. "Solid" tumors can include carcinomas or sarcomas.

Cancers that may be treated by the therapeutic compositions of the invention include those classified by site include cancer of the oral cavity and pharynx (lip, tongue, salivary gland, floor of mouth, gum and other mouth, nasopharynx, tonsil, oropharynx, hypopharynx, other oral/pharynx); cancers of the digestive system (esophagus; stomach; small intestine; colon and rectum; anus, anal canal, and anorectum; liver; intrahepatic bile duct; gallbladder; other biliary; pancreas; retroperitoneum; peritoneum, omentum, and mesentery; other digestive); cancers of the respiratory system (nasal cavity, middle ear, and sinuses; larynx; lung and bronchus; pleura; trachea, mediastinum, and other respiratory); cancers of the mesothelioma; bones and joints; and soft tissue, including heart; skin cancers, including melanomas and other non-epithelial skin cancers; Kaposi's sarcoma and breast cancer; cancer of the female genital system (cervix uteri; corpus uteri; uterus, ovary; vagina; vulva; and other female genital); cancers of the male genital system (prostate gland; testis; penis; and other male genital); cancers of the urinary system (urinary bladder; kidney and renal pelvis; ureter; and other urinary); cancers of the eye and orbit; cancers of the brain and nervous system (brain; and other nervous system); cancers of the endocrine system (thyroid gland and other endocrine, including thymus); lymphomas (Hodgkin's disease and non-Hodgkin's lymphoma), multiple myeloma, and leukemia (lymphocytic leukemia; myeloid leukemia; monocytic leukemia; and other leukemia).

Other cancers, classified by histological type, that may be suitable targets for the therapeutic compositions according to the present invention include, but are not limited to, neoplasm, malignant; Carcinoma, NOS; Carcinoma, undifferentiated, NOS; Giant and spindle cell carcinoma; Small cell carcinoma, NOS; Papillary carcinoma, NOS; Squamous cell carcinoma, NOS; Lymphoepithelial carcinoma; Basal cell carcinoma, NOS; Pilomatrix carcinoma; Transitional cell carcinoma, NOS; Papillary transitional cell carcinoma; Adenocarcinoma, NOS; Gastrinoma, malignant; Cholangiocarcinoma; Hepatocellular carcinoma, NOS; Combined hepatocellular carcinoma and cholangiocarcinoma; Trabecular adenocarcinoma; Adenoid cystic carcinoma; Adenocarcinoma in adenomatous polyp; Adenocarcinoma, familial polyposis coli; Solid carcinoma, NOS; Carcinoid tumor, malignant; Bronchioloalveolar adenocarcinoma; Papillary adenocarcinoma, NOS; Chromophobe carcinoma; Acidophil carcinoma; Oxyphilic adenocarcinoma; Basophil carcinoma; Clear cell adenocarcinoma, NOS; Granular cell carcinoma; Follicular adenocarcinoma, NOS; Papillary and follicular adenocarcinoma; Nonencapsulating sclerosing carcinoma; Adrenal cortical carcinoma; Endometroid carcinoma; Skin appendage carcinoma; Apocrine adenocarcinoma; Sebaceous adenocarcinoma; Ceruminous adenocarcinoma; Mucoepidermoid carcinoma; Cystadenocarcinoma, NOS; Papillary cystadenocarcinoma, NOS; Papillary serous cystadenocarcinoma; Mucinous cystadenocarcinoma, NOS; Mucinous adenocarcinoma; Signet ring cell carcinoma; Infiltrating duct carcinoma; Medullary carcinoma, NOS; Lobular carcinoma; Inflammatory carcinoma; Paget's disease, mammary; Acinar cell carcinoma; Adenosquamous carcinoma; Adenocarcinoma w/ squamous metaplasia; Thymoma, malignant; Ovarian stromal tumor, malignant; Thecoma, malignant; Granulosa cell tumor, malignant; Androblastoma, malignant; Sertoli cell carcinoma; Leydig cell tumor, malignant; Lipid cell tumor, malignant; Paraganglioma, malignant; Extra-mammary paraganglioma, malignant; Pheochromocytoma; Glomangiosarcoma; Malignant melanoma, NOS; Amelanotic melanoma; Superficial spreading melanoma; Malig melanoma in giant pigmented nevus; Epithelioid cell melanoma; Blue nevus, malignant; Sarcoma, NOS; Fibrosarcoma, NOS; Fibrous histiocytoma, malignant; Myxosarcoma; Liposarcoma, NOS; Leiomyosarcoma, NOS; Rhabdomyosarcoma, NOS; Embryonal rhabdomyosarcoma; Alveolar rhabdomyosarcoma; Stromal sarcoma, NOS; Mixed tumor, malignant, NOS; Mullerian mixed tumor; Nephroblastoma; Hepatoblastoma; Carcinosarcoma, NOS; Mesenchymoma, malignant; Brenner tumor, malignant; Phyllodes tumor, malignant; Synovial sarcoma, NOS; Mesothelioma, malignant; Dysgerminoma; Embryonal carcinoma, NOS; Teratoma, malignant, NOS; Struma ovarii, malignant; Choriocarcinoma; Mesonephroma, malignant; Hemangiosarcoma; Hemangioendothelioma, malignant; Kaposi's sarcoma; Hemangiopericytoma, malignant; Lymphangiosarcoma; Osteosarcoma, NOS; Juxtacortical osteosarcoma; Chondrosarcoma, NOS; Chondroblastoma, malignant; Mesenchymal chondrosarcoma; Giant cell tumor of bone; Ewing's sarcoma; Odontogenic tumor, malignant; Ameloblastic odontosarcoma; Ameloblastoma, malignant; Ameloblastic fibrosarcoma; Pinealoma, malignant; Chordoma; Glioma, malignant; Ependymoma, NOS; Astrocytoma, NOS; Protoplasmic astrocytoma; Fibrillary astrocytoma; Astroblastoma; Glioblastoma, NOS; Oligodendroglioma, NOS; Oligodendroblastoma; Primitive neuroectodermal; Cerebellar sarcoma, NOS; Ganglioneuroblastoma; Neuroblastoma, NOS; Retinoblastoma, NOS; Olfactory neurogenic tumor; Meningioma, malignant; Neurofibrosarcoma; Neurilemmoma, malignant; Granular cell tumor, malignant; Malignant lymphoma, NOS; Hodgkin's disease, NOS; Hodgkin's; paragranuloma, NOS; Malignant lymphoma, small lymphocytic; Malignant lymphoma, large cell, diffuse; Malignant lymphoma, follicular, NOS; Mycosis fungoides; Other specified non-Hodgkin's lymphomas; Malignant histiocytosis; Multiple myeloma; Mast cell sarcoma; Immunoproliferative small intestinal disease; Leukemia, NOS; Lymphoid leukemia, NOS; Plasma cell leukemia; Erythroleukemia; Lymphosarcoma cell leukemia; Myeloid leukemia, NOS; Basophilic leukemia; Eosinophilic leukemia; Monocytic leukemia, NOS; Mast cell leukemia; Megakaryoblastic leukemia; Myeloid sarcoma; and Hairy cell leukemia.

"Epithelial cancers" as defined herein refers to cancer(s) that develops from epithelium or related tissues in the skin, hollow viscera, and other organs. Epithelial cancers include but are not limited to breast cancer, lung cancer, liver cancer, buccal cancer, stomach cancer, colon cancer, nasopharyngeal cancer, dermal cancer, renal cancer, brain tumor, prostate cancer, ovarian cancer, cervical cancer, endometrial cancer, intestinal cancer, pancreatic cancer, and bladder cancer.

"Patient" or "Subject" as used herein refers to a mammalian subject diagnosed with or suspected of having or developing a proliferative disease such as cancer. Exemplary patients may be humans, apes, dogs, pigs, cattle, cats, horses, goats, sheep, rodents and other mammalians that can benefit develop proliferative diseases such as cancer.

As used herein, "substantially purified" or "substantially isolated" refers to a molecule (e.g. a compound) in a state that it is separated from substantially all other molecules normally associated with it in its native state. Preferably, a substantially purified molecule is the predominant species present in a preparation. Particularly, a substantially purified molecule may be greater than 60% free, preferably 75% free, or 85%, 86%, 87%, 88%, 89%, 90%, 91%, 92%, 93%, 94%, 95%, 96%, 97%, 97.5%, 98%, 98.5%, 99%, or 99.5% free, or any range between any two recited percentages free from the other molecules (exclusive of solvent) present in the natural mixture. In some embodiments, a substantially purified molecule is more preferably 90% free, and most preferably 95% free from the other molecules (exclusive of solvent) present in the natural mixture. The term "substantially purified" or "substantially isolated" is not intended to include molecules or substances present in their native state. In certain embodiments, the term "substantially purified" or "substantially isolated" includes purifying one KLH moiety from another KLH moiety (e.g., substantially purifying or substantially isolating a KLH dimer moiety from a KLH trimer moiety). For example, a substantially purified KLH dimer moiety (or other immunogenic multimer moiety) may be than 60% free, preferably 75% free, 85%, 86%, 87%, 88%, 89%, 90%, 91%, 92%, 93%, 94%, 95%, 96%, 97%, 97.5%, 98%, 98.5%, 99%, or 99.5% free, or any range between any two recited percentages free from other KLH multimers present in the mixture. In some embodiments, a KLH dimer (or other immunogenic multimer moiety) is more preferably 90% free, and most preferably 95% free from other KLH multimers present in the mixture. In another embodiment, the term "substantially purified" or "substantially isolated" does not include purifying one multimer moiety from another multimer moiety, e.g, does not include purifying one KLH moiety from another KLH moiety (e.g. KLH dimers and KLH trimmers are included in a substantially purified or substantially isolated composition) but impurities are substantially removed.

"Administering" is referred to herein as providing a therapeutic composition of the invention to a patient. By way of example and not limitation, composition administration, e.g., injection, may be performed by intravenous (i.v.) injection, subcutaneous (s.c.) injection, intradermal (i.d.) injection, intraperitoneal (i.p.) injection, or intramuscular (i.m.) injection. One or more such routes may be employed. Parenteral administration can be, for example, by bolus injection or by gradual perfusion over time. Alternatively, or concurrently, administration may be by the oral route or nasal route. Additionally, administration may also be by surgical deposition of a bolus or positioning of a medical device.

"A patient in need thereof" is referred to herein as a patient diagnosed with or suspected of having a proliferative disorder. In one embodiment, the patient has or is likely to develop cancer.

As used herein, the term "antigen" is defined as any substance capable of eliciting an immune response, with or without the help of a protein carrier and/or an adjuvant. Preferably the antigen of the inventive compositions includes a carbohydrate and more preferably glycan-antigen and most preferably a SSEA-4, Globo H or SSEA-3 moiety.

As used herein, the term "immunogenicity" refers to the ability of an immunogen, antigen, or vaccine to stimulate an immune response.

As used herein, the term "immunotherapy" refers to an array of treatment strategies based upon the concept of modulating the immune system to achieve a prophylactic and/or therapeutic goal.

As used herein, the term "epitope" is defined as the parts of an antigen molecule which contact the antigen binding site of an antibody or a T cell receptor.

The "therapeutic compositions" of the invention include "immunogenic conjugates and/or therapeutic conjugates and/or "therapeutic antibodies." The therapeutic conjugates include at least one antigen linked to a carrier. Preferably, the linkage of the therapeutic conjugate is covalent. In one embodiment of the therapeutic conjugate, the antigen is a glycan such as Globo series antigen (SSEA-4, Globo H or SSEA-3) moiety, and the carrier is a KLH moiety and/or a KLH moiety subunit. As such, the term therapeutic conjugate encompasses one or more KLH moiety subunits linked to one or more Globo series antigen moieties. In one embodiment, the term therapeutic conjugate encompasses a one or more KLH moieties linked to about or at least 1, 10, $10^2$ or $10^3$ or more Globo series antigen moieties. Another embodiment encompasses isolated dimers, trimers, tetramers, pentamers or hexamers of such Globo series antigen linked KLH moiety subunits, or combinations thereof.

"Therapeutic antibodies" are defined to be as antibodies (as further defined below) that specifically bind the inventive therapeutic conjugates and preferably the Globo series antigen moiety portion of the therapeutic conjugates.

As used herein, the term "vaccine" refers to a therapeutic composition that contains a therapeutic conjugate that is used to confer immunity against a disease associated with the antigen. Cancer vaccines are designed to boost the body's natural ability to protect itself, through the immune system, from dangers posed by damaged or abnormal cells such as cancer cells. A protective immune response is one that reduces the severity of disease, including but not limited to, prevention of disease, delay in onset of disease, decreased severity of symptoms, decreased morbidity, and delayed mortality. Preferably, a vaccine is capable of activating both humoral immune response (e.g. stimulation of the production of antibodies by B lymphocytes) and cellular immune response (e.g. an immune response that is mediated by T-lymphocytes and/or other cells, such as NK cells and macrophages). Standard assays have been developed to determine the immune response such as enzyme-linked immunosorbent assay (ELISA), flow cytometry, cell proliferation assay, CTL assays, and ADCC/CDC assays.

As used herein, the term "glycan" refers to a polysaccharide, or oligosaccharide. Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans usually consist solely of O-glycosidic linkages between monosaccharides. For example, cellulose is a glycan (or more specifically a glucan) composed of β-1,4-linked D-glucose, and chitin is a glycan composed of β-1,4-linked N-acetyl-D-glucosamine. Glycans can be homo or heteropolymers of monosaccharide residues, and can be linear or branched. Glycans can be found attached to proteins as in glycoproteins and proteoglycans. They are generally found on the exterior surface of cells. O- and N-linked glycans are very common in eukaryotes but may also be found, although less commonly, in prokaryotes. N-Linked glycans are found attached to the R-group nitrogen (N) of asparagine in the sequon. The sequon is an Asn-X-Ser or Asn-X-Thr sequence, where X is any amino acid except praline. The preferred glycan is a Globo series antigen (SSEA-4, Globo H or SSEA-3) moiety.

Cancers expressing Globo series antigens (SSEA-4, Globo H or SSEA-3) include, but are not limited to, sarcoma, skin cancer, leukemia, lymphoma, brain cancer, lung cancer, breast cancer, oral cancer, esophagus cancer, stomach cancer, liver cancer, bile duct cancer, pancreas cancer, colon cancer, kidney cancer, cervix cancer, ovary cancer and prostate cancer.

"SSEA-4 moiety" is defined herein to be a glycan (i.e., a molecule containing a sugar moiety) that is SSEA-4 or a fragment or analog thereof. SSEA-4 is a glycan containing the hexasaccharide epitope (Neu5Acα2→3Galβ1→3GalNAcβ1→3Galα1→4Galβ1→4Glcβ1), and optionally, a non-sugar moiety. Its fragment is a glycan containing a fragment of the hexasaccharide epitope and, if applicable, the non-sugar moiety.

"Globo H moiety" is defined herein to be a glycan (i.e., a molecule containing a sugar moiety) that is Globo H or a fragment or analog thereof. Globo H is a glycan containing the hexasaccharide epitope (Fucα1→2 Galβ1→3 GalNAcβ1→3 Galα1→4 Galβ1→4 Glc), and optionally, a non-sugar moiety. Its fragment is a glycan containing a fragment of the hexasaccharide epitope and, if applicable, the non-sugar moiety.

"SSEA-3 moiety" is defined herein to be a glycan (i.e., a molecule containing a sugar moiety) that is SSEA-3 or a fragment or analog thereof. SSEA-3 is a glycan containing the pentasaccharide epitope (Galβ1→3GalNAcβ1→3Galα1→4Galβ1→4Glcβ1), and optionally, a non-sugar moiety. Its fragment is a glycan containing a fragment of the pentasaccharide epitope and, if applicable, the non-sugar moiety.

"Keyhole Limpet Hemocyanin" (KLH) is a large, multi-subunit, oxygen-carrying, metalloprotein found in the hemolymph of the giant keyhole limpet, *Megathura crenulata*. KLH is heterogeneous glycosylated protein consisting of subunits with a molecular weight of about 350,000 to about 390,000 in aggregates with molecular weights of about 400 kDa (e.g., a KLH monomer) to about 8000 kDa (e.g., a KLH didecamer). Each domain of a KLH subunit contains two copper atoms that together bind a single oxygen molecule. When oxygen is bound to hemocyanin, the molecule takes on a distinctive transparent, opalescent blue color. In certain embodiments, the KLH protein is potently immunogenic yet safe in humans. In certain embodiments, KLH may be purified from the hemolymph of *Megathura crenulata* by a series of steps that typically includes ammonium sulfate precipitation and dialysis, and may involve chromatographic purification to obtain the highest purity. In certain embodiments, KLH purification may also include endotoxin removal, but this step may be unnecessary because the endotoxin can serve as an adjuvant when injected for antibody production. Preferably, a high quality KLH preparation with the clear opalescent blue color is the best indicator of KLH solubility. In certain embodiments, the KLH monomeric units assemble into a large multimer (decamer or didecamer) with a total molecular weight of about 4,000 kDa to 8,000 kDa.

In certain embodiments, the higher KLH multimers have molecular weights of approximately 8-10 million with sedimentation coefficients of about 92-107S. The amount of higher KLH multimers present is based on sedimentation-equilibrium and/or sedimentation-velocity ultracentrifugation analyses. In other embodiments, the KLH of the invention demonstrates an enhanced immunogenic activity, particularly enhanced anti-tumor activity. The enhanced immunogenic activity is seen for example, but not limited, (a) with injection of KLH (without adjuvant), (b) with KLH used as an adjuvant, (c) with KLH used as a carrier immunogen for haptens or weakly immunogenic antigens, and (d) with KLH used as an anti-tumor agent. The KLH composition of the invention exhibits enhanced anti-tumor activity for many tumors, including, but not limited to, bladder, breast, ovarian tumors, etc. In certain embodiments, two KLH moieties can form a dimer via a covalent linkage between KLH monomers. Without being limited by theory, it is believed that the covalent linkage between KLH moieties is through a disulfide bond. In certain embodiments, two or more KLH moieties can form a dimer, trimer, tetramer, pentamer, hexamer, etc. via a covalent linkage between KLH monomers, dimers, trimers, etc. Without being limited by theory, it is believed that the covalent linkage between KLH moieties is through a disulfide bond.

In certain embodiments, during conjugation of a Globo series antigen (SSEA-4, Globo H or SSEA-3) moiety protein to a KLH moiety, a KLH moiety protein in certain embodiments shows a reduction in molecular weight compared to the intact molecule preferably due to Globo series antigen moiety subunit dissociation. In other embodiments, the conjugation methods disclosed herein result in a KLH subunit dissociation not previously reported. While not wishing to be bound to any particular theory, it is envisaged that the high glycosylation level of the inventive Globo series antigen moiety-KLH moiety subunit conjugates results in the formation hydrogen bonding between the Globo series antigen moieties. As such, in certain embodiments, the Van Der Waals forces and hydrophobic interactions between the KLH moiety subunits are displaced by Globo series antigen hydrogen bonding and this leads to KLH moiety subunit separation. Following conjugation, the KLH moiety subunits of a Globo series antigen moiety-KLH moiety conjugate preferably aggregate to form novel monomers, dimers, trimers, tetramers, pentamers, hexamers or any combination thereof. The resulting exemplary therapeutic Globo series antigen moiety-KLH moiety conjugates, with an unexpectedly large epitope ratio, have surprising and unexpected superior immunogenic attributes. In certain embodiments, the Globo series antigen moieties are conjugated to lysines on KLH1 and KLH2. In other embodiments, the Globo series antigen moieties are not conjugated to lysines on KLH1 and KLH2.

As used herein, "epitope ratio" relating to the therapeutic conjugates disclosed herein refers to for example, the relationship of antigen epitopes to carrier molecules in a therapeutic conjugate. Preferably, it refers to the relationship of Globo series antigen (SSEA-4, Globo H or SSEA-3) moieties to KLH moieties. Most preferably the epitope ratio of a therapeutic conjugate is calculated using the following formula=(actual Globo series antigen moiety weight/Globo series antigen moiety molecular weight)/(actual KLH moiety weight/KLH moiety molecular weight) combination. Epitope ratios are readily determinable by those of skill in the art. Preferably, the weights of Globo series antigen are determined for example by high performance anion exchange chromatography with pulsed amperometric detection (HPAEC-PAD).

In certain illustrative embodiments, the invention also encompasses isolated therapeutic antibodies, which specifically bind the therapeutic conjugates disclosed herein with affinity, as well as their use in the treatment and/or diagnosis of proliferative disease.

As used herein, the terms "antibody" and "antibodies" (immunoglobulins) encompass monoclonal antibodies (including full-length monoclonal antibodies), polyclonal antibodies, multispecific antibodies (e.g., bispecific antibodies) formed from at least two intact antibodies, human antibodies, humanized antibodies, camelised antibodies, chimeric antibodies, single-chain Fvs (scFv), single-chain antibodies, single domain antibodies, domain antibodies, Fab fragments, F(ab')2 fragments, antibody fragments that exhibit the desired biological activity, disulfide-linked Fvs (sdFv), and anti-idiotypic (anti-Id) antibodies (including, e.g., anti-Id antibodies to antibodies of the invention), intrabodies, and epitope-binding fragments of any of the above. In particular, antibodies include immunoglobulin molecules and immunologically active fragments of immunoglobulin molecules, i.e., molecules that contain an antigen-binding site Immunoglobulin molecules can be of any type (e.g., IgG, IgE, IgM, IgD, IgA and IgY), class (e.g., IgG1, IgG2, IgG3, IgG4, IgA1 and IgA2) or subclass.

"Affinity" of an antibody for an epitope, e.g., the Globo series antigen (SSEA-4, Globo H or SSEA-3) moiety of a therapeutic conjugate, to be used in the treatment(s) described herein is a term well understood in the art and means the extent, or strength, of binding of antibody to epitope. Affinity may be measured and/or expressed in a number of ways known in the art, including, but not limited to, equilibrium dissociation constant (KD or Kd), apparent equilibrium dissociation constant (KD' or Kd'), and $IC_{50}$ (amount needed to effect 50% inhibition in a competition assay). It is understood that, for purposes of this invention, an affinity is an average affinity for a given population of antibodies which bind to an epitope. Values of KD' reported herein in terms of mg IgG per mL or mg/mL indicates mg Ig per mL of serum, although plasma can be used. When antibody affinity is used as a basis for administration of the treatment methods described herein, or selection for the treatment methods described herein, antibody affinity can be measured before and/or during treatment, and the values obtained can be used by a clinician in assessing whether a human patient is an appropriate candidate for treatment.

As used herein, the term "specifically binding," refers to the interaction between binding pairs (e.g., an antibody and an antigen). In various instances, specifically binding can be embodied by an affinity constant of at least or about $10^{-6}$ moles/liter, about $10^{-7}$ moles/liter, about $10^{-8}$ moles/liter, or less, about $10^{-9}$ moles/liter, or about $10^{-10}$ moles/liter, or less, or any range between any two recited binding affinity constants.

Exemplary antibodies against the Globo series antigen (SSEA-4, Globo H or SSEA-3) may be prepared by collecting body fluid from the immunized subject examined for the increase of desired antibodies such as the serum, and by separating serum from the blood by any conventional method.

Antibodies are generally raised by multiple injections of the relevant antigen and an adjuvant. It may be useful to conjugate the relevant antigen to a protein that is immunogenic in the species to be immunized, e.g., keyhole limpet hemocyanin.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of an adjuvant, and then administered to the subject.

In certain embodiments, subjects can be boosted until the titer plateaus by several administrations of antigen mixed with an appropriately amount of adjuvant. An appropriate carrier may also be used for immunization. After immunization as above, serum is examined by a method for an increase in the amount of desired antibodies.

The vaccine can comprise a carbohydrate antigen or its immunogenic fragment and an adjuvant. In yet another embodiment, the vaccine comprises a carbohydrate antigen or its immunogenic fragment; a carrier protein and an OBI-821 adjuvant. In another embodiment, the vaccine comprises a carbohydrate antigen selected from SSEA-4, KLH, and an OBI-821 adjuvant. Non limiting examples of carrier protein include, for example, KLH or DT-CRM 197.

Therapeutic compositions can include other anti-cancer/anti-proliferative drugs as well as adjuvants and other immunomodulatory molecules such as cytokines or chemokines. In certain embodiments, the combination can be a co-administration of separate agent/compositions or co-formulation. These agents can be delivered in a kit together in separate containers or a single container.

Adjuvants are pharmacological or immunological agents that modify the effects of other agents. They can be an inorganic or organic chemical, macromolecule or whole cancer cells or portions thereof which enhance the immune response to given antigen. Adjuvants include complete and incomplete Freund's adjuvant, Toll-Like Receptor molecules and mimetics thereof, LPS, lipoproteins, lipopeptides, flagellin, double-stranded RNA, unmethylated CpG islands, levamisole, bacillus Calmette-Guerin, octreotide, isoprinosine and Zadaxin, various forms of DNA and RNA classically released by bacteria and viruses, PD-1 antagonists and CTLA antagonists. In one embodiment, the adjuvant is a saponin adjuvant.

In certain embodiment, the saponin adjuvant is OBI-821, which is substantially pure. In other embodiments, the OBI-821 is a biologically active fragments thereof. The adjuvant may also encompass impure forms of OBI-821. The purified OBI-821 exhibit enhanced adjuvant effect when administered with a vaccine described herein or admixed with other substantially pure saponin or non-saponin adjuvants.

OBI-821 adjuvant is naturally occurring glycosides, extracted in high purify from the bark of the *Quillaja saponaria* Molina tree, by high pressure liquid chromatography (HPLC), low pressure liquid silica chromatography, and hydrophilic interactive chromatography (HILIC) as described in, for example, U.S. Pat. Nos. 5,057,540 and 6,524,584, the content of which is incorporate by reference in its entirety.

In certain embodiments, OBI-821 adjuvant comprises at least one isolated compound of formula I as follows:

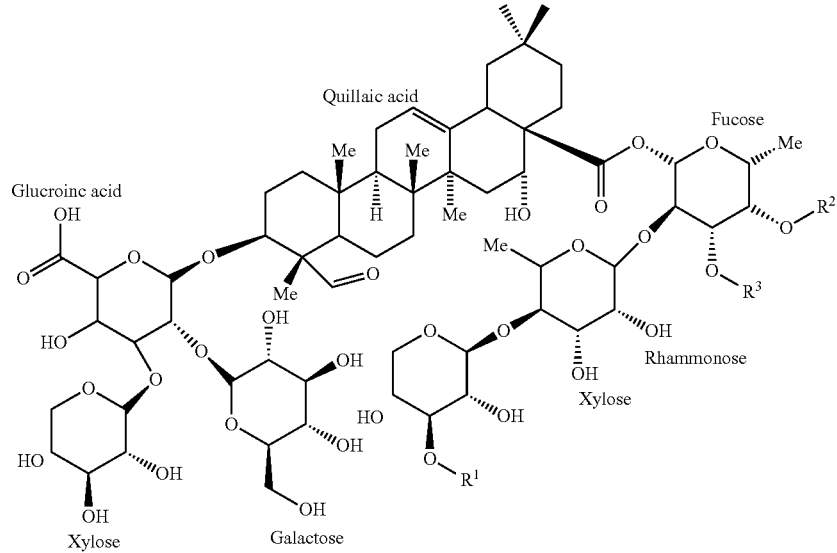

Formula (I)

wherein $R^1$ is β-D-Apiose or β-D-Xylose or H; and $R^2$ and $R^3$ are independently H, fatty acyl moiety.

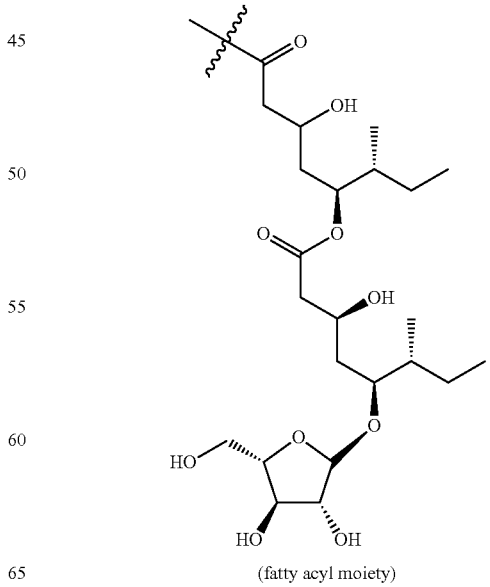

(fatty acyl moiety)

OBI-821 adjuvant can also comprise an isolated compound of formula I, wherein:
(i) $R^1$ is β-D-Apiose, $R^2$ is the fatty acyl moiety depicted above, and $R^3$ is H (1989 compound V1A);
(ii) $R^1$ is β-D-Apiose, $R^2$ is H, and $R^3$ is the fatty acyl moiety depicted above (1989 compound V1B);
(iii) $R^1$ is β-D-Xylose, $R^2$ is the fatty acyl moiety depicted above, and $R^3$ is H (1989 compound V2A); or
(iv) $R^1$ is β-D-Xylose, $R^2$ is H, and $R^3$ is the fatty acyl moiety depicted above (1989 compound V2B).

Collectively, 1989 compound V1A, 1989 compound V1B, 1989 compound V2A and 1989 compound V2B are called "1989 compounds mixture."

Table 1 summarizes the functional groups of 1989 compounds and the mole % of each 1989 compound in the 1989 compounds mixture.

TABLE 1

| Mole % | $R^1$ | $R^2$ | $R^3$ |
|---|---|---|---|
| 1989 Compound V1A 60-75% | β-D-Apiose | (fatty acyl moiety depicted) | H |
| 1989 Compound V1B 0-10% | β-D-Apiose | H | (fatty acyl moiety depicted) |

TABLE 1-continued

| Mole % | R¹ | R² | R³ |
|---|---|---|---|
| 1989 Compound V2A 25-40% | β-D-Xylose 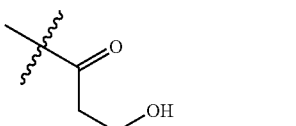 | 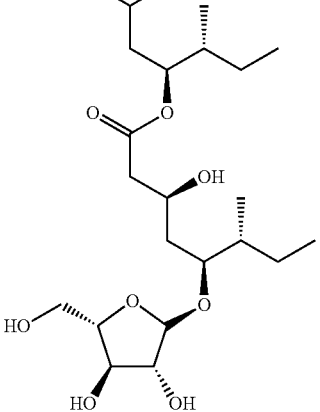 | H |
| 1989 Compound V2B 0-10% | β-D-Xylose  | H |  |

OBI-821 adjuvant can comprise an isolated compound of formula I where:

(i) R¹ is H, R² is the fatty acyl moiety depicted above, and R³ is H (1857 compound A);

(ii) le is H, R² is H, and R³ is the fatty acyl moiety depicted above (1857 compound B);

Collectively, 1857 compound A and 1857 compound B are called "1857 compounds mixture."

Table 2 summarizes the functional groups of 1857 compounds and the mole % of each 1857 compound in the 1857 compounds mixture. HPLC.

TABLE 2

| Mole % | R¹ | R² | R³ |
|---|---|---|---|
| 1857 Compound A 90-100% | H | [structure: ketone-linked chain with OH groups, ester, and furanose sugar moiety] | H |
| 1857 Compound B 0-10% | H | H | [structure: ketone-linked chain with OH groups, ester, and furanose sugar moiety] |

OBI-821 adjuvant comprises one or more of the following compounds:
- (i) 1857 compound A;
- (ii) 1857 compound B;
- (iii) 1989 compound V1A;
- (vi) 1989 compound V1B;
- (v) 1989 compound V2A; or
- (vi) 1989 compound V2B.

The percentages of the 1857 compounds mixture and the 1989 compound mixture in OBI-821 adjuvant can range as follows:
- (i) about 1 mole % to about 25 mole % of OBI-821 comprising an 1857 compounds mixture; and
- (ii) about 75 mole % to about 99 mole % of OBI-821 comprising a 1989 compounds mixture.

All of the mole % can be varied by 0.1% increments and including any % range within any of the recited ranges (e.g. about 75 mole % to about 99 mole % includes about 87% to about 90%, and about 90.5% to about 97%, while about 1 mole % to about 25 mole % includes about 3.5% to about 11%, about 10% to about 14%). Further exemplary mole % can range from about 1, 2, 3, 4, 5, 6, 7, 8, 9, 10, 11, 12, 13, 14, 15, 16, 17, 18, 19, 20, 21, 22, 23, 24, to about 25%; or from about 75, 76, 77, 78, 79, 80, 81, 82, 83, 84, 85, 86, 87, 88, 89, 90, 91, 92, 93, 94, 95, 96, 97, 98 to about 99% or ranges between any two recited mole % herein.

The 1989 compounds mixture may comprise about 60-75 mole % of 1989 compound V1A; about 0-10 mole % of 1989 compound V1B; about 25-40 mole % of 1989 compound V2A; and about 0-10 mole % of 1989 compound V2B. All of the mole % can be varied by 0.1 increment (e.g. 65%, 2.5%, 35.6%). Further exemplary mole % can range from about 1, 2, 3, 4, 5, 6, 7, 8, 9, 10, 11, 12, 13, 14, 15, 16, 17, 18, 19, 20, 21, 22, 23, 24, to about 25%; 60, 61, 62, 63, 64, 65, 66, 67, 68, 69, 70, 71, 72, 73, 74 to about 75%; 25, 26, 27, 28, 29, 30, 31, 32, 33, 34, 35, 36, 37, 38, 39, to about 40% or ranges between any two recited mole % herein.

The 1857 compounds mixture may comprise about 90-100 mole % of 1857 compound A; about 0-10 mole % of 1857 compound B. All of the mole % can be varied by 0.1 increment (e.g., 65%, 2.5%, 35.6%). Further exemplary mole % can range from about 1, 2, 3, 4, 5, 6, 7, 8, 9, to about 10% or 90, 91, 92, 93, 94, 95, 96, 97, 98, to about 99%, or ranges between any two recited mole % herein.

In another embodiment, the substantially pure OBI-821 is purified from a crude *Quillaja saponaria* extract, wherein said OBI-821 is characterized by a single predominant peak which comprises 90% or more of the total area of all peaks of a chromatogram, excluding the solvent peak, when analyzed on reverse phase-HPLC on a Symmetry C18 column having 5 um particle size, 100 Å pore, 4.6 mm ID×25 cm L with a elution program comprising mobile phase of A:B 95%:5% to 75%:25% in 11 minutes, which mobile phase A is distilled water with 0.1% trifluoroacetic acid, and mobile phase B is acetonitrile with 0.1% trifluoroacetic acid at a flow rate of 1 mL/min. Further exemplary % ratios can range from (about 95%, 94, 93, 92, 91, 90, 89, 88, 87, 86, 85, 84, 83, 82, 81, 80, 79, 78, 77, 76, to about 75%) versus from about 25%, 24, 23, 22, 21, 20, 29, 28, 17, 16, 15, 14, 13, 12, 11, 10, 9, 8, 7, 6, to about 5%); ranges between any two recited mole % herein.

The vaccine can comprise a carbohydrate antigen or its immunogenic fragment and an OBI-821 adjuvant. In yet another embodiment, the vaccine comprises a carbohydrate antigen or its immunogenic fragment; a carrier protein and an OBI-821 adjuvant. In another embodiment, the vaccine comprises a carbohydrate antigen selected from SSEA-4, KLH, and an OBI-821 adjuvant. Non limiting examples of carrier protein include KLH.

The terms "a-galactosyl-ceramide" and "a-GalCer" refer to a glycolipid that stimulates natural killer T cells to produce both T helper 1 (TH1) and TH2 cytokine, as described in U.S. Pat. No. 8,268,969, the content of which is incorporate by reference in its entirety. In certain embodiment, OBI-834 (also known as C34) adjuvant is characterized by the following exemplary structure:

kines (RANTES, MCP-1, MW-1α, and MIP-1β), C—X—C chemokines (IL-8), C chemokines (Lymphotactin), and CXXXC chemokines (Fractalkine).

The therapeutic compositions of the invention can further include PD-1/PD-L1 inhibitors (cytotoxic T cell lymphocyte (CTLs) immunotherapy), CTLA-4 immunotherapy, CDK4/6 inhibitors (target therapy), PI3K inhibitors (target therapy), mTOR inhibitors (target therapy), AKT inhibitors (target therapy), Pan-Her inhibitors (target therapy). These inhibitors can be modified to generate the respective monoclonal antibody as well. Such antibodies can be included in therapeutic compositions of the invention.

The therapeutic compositions can include other anti-cancer/anti-proliferative or chemotherapeutic agents. In some embodiments, examples of such agents are found in Cancer Principles and Practice of Oncology by V. T. Devita and S. Hellman (editors), 6th edition (Feb. 15, 2001), Lippincott Williams & Wilkins Publishers. Such anti-cancer agents include, but are not limited to, the following: hormonal therapeutic agents (e.g., selective estrogen receptor modulators, androgen receptor modulators), monoclonal antibody therapy, chemotherapy, retinoid receptor modulators, cytotoxic/cytostatic agents, antineoplastic agents, anti-proliferative agents, prenyl-protein transferase inhibitors, HMG-CoA reductase inhibitors, nitrogen mustards, nitroso ureas, angiogenesis inhibitors (e.g., bevacizumab), inhibitors of cell proliferation and survival signaling pathway, apoptosis inducing agents, agents that interfere with cell cycle checkpoints, agents that interfere with receptor tyrosine kinases (RTKs), mammalian target of rapamycin (mTOR) inhibitors, human epidermal growth factor receptor 2 (HER2) inhibitors, epidermal growth factor receptor (EGFR) inhibitors, integrin blockers, NSAIDs, PPAR agonists, inhibitors of inherent multidrug resistance (MDR), anti-emetic agents, agents useful in the treatment of anemia, agents useful in the treatment of neutropenia, immunologic-

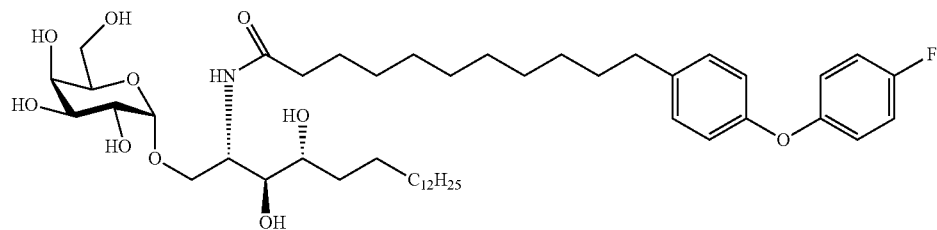

As used herein, the term "cytokine" refers to any of numerous small, secreted proteins that regulate the intensity and duration of the immune response by affecting immune cells differentiation process usually involving changes in gene expression by which a precursor cell becomes a distinct specialized cell type. Cytokines have been variously named as lymphokines, interleukins, and chemokines, based on their presumed function, cell of secretion, or target of action. For example, some common interleukins include, but are not limited to, IL-2, IL-12, IL-18, IL-2, IFN-γ, TNF, IL-4, IL-10, IL-13, IL-21, GM-CSF, and TGF-β.

As used herein, the term "chemokine" refers to any of various small chemotactic cytokines released at the site of infection that provide a means for mobilization and activation of lymphocytes. Chemokines attract leukocytes to infection sites. Chemokines have conserved cysteine residues that allow them to be assigned to four groups. The groups, with representative chemokines, are C—C chemoenhancing drugs, biphosphonates, aromatase inhibitors, agents inducing terminal differentiation of neoplastic cells, γ-secretase inhibitors, cancer vaccines, and any combination thereof.

The therapeutic compositions (also referred to herein as pharmaceutical compositions) generally include a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, intramuscular, intra-arterial, oral (e.g., inhalation), transdermal (topical), transmucosal, and rectal administration. Solutions or suspensions used for parenteral, intradermal, or subcutaneous application can include the following components: a sterile diluent such as water for injection, saline solution, phosphate buffered saline, tris-buffered saline, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates and agents for the adjustment of tonicity such as sodium chloride or dextrose. The pH value can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for an injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL® (BASF, Parsippany, N.J.), or phosphate buffered saline (PBS). In all cases, the composition should be sterile and should be fluid to the extent that easy syringability exists. It should be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying, which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Furthermore, for oral administration, the formulations of the invention can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. The compositions of the invention can be also introduced in microspheres or microcapsules, e.g., fabricated from poly-glycolic acid/lactic acid (PGLA) (see, U.S. Pat. Nos. 5,814,344; 5,100,669 and 4,849,222; PCT Publication Nos. WO 95/11010 and WO 93/07861). Liquid preparations for oral administration can take the form of, for example, solutions, syrups, emulsions or suspensions, or they can be presented as a dry product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound.

For administration by inhalation, or nasal administration the compounds are delivered in the form of an aerosol spray from pressured container or dispenser which contains a suitable propellant, e.g., a gas such as carbon dioxide, or a nebulizer.

Systemic administration can also be transmucosal or transdermal. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration may be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

According to implementations, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to cell-specific antigens) can also be used as pharmaceutically acceptable carriers. These can be prepared according to methods known to those skilled in the art, for example, as described in U.S. Pat. No. 4,522,811, which is incorporated by reference herein.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

The immunogenic formulations of the invention can be delivered parenterally, i.e., by intravenous (i.v.), subcutaneous (s.c.), intraperitoneal (i.p.), intramuscular (i.m.), subdermal (s.d.), or intradermal (i.d.) administration, by direct injection, via, for example, bolus injection, continuous infusion, or gene gun (e.g., to administer a vector vaccine to a subject, such as naked DNA or RNA). Formulations for injection can be presented in unit dosage form, e.g., in ampoules or in multi-dose containers, with an added preservative. The compositions can take such forms as excipients, suspensions, solutions or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water, before use.

The present invention also contemplates various mucosal vaccination strategies.

Dosage: Toxicity and therapeutic efficacy of such therapeutic compositions may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutic compositions which exhibit high therapeutic indices are preferred. While compounds that exhibit toxic side effects can be used, care should be taken to design a delivery system that targets such compounds to the site of affected location to minimize potential damage to uninfected cells and, thereby, reduce side effects.

Data obtained from cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In the disclosed compositions, both the antigen and/or the adjuvant or any other relevant components are present in immunogenically effective amounts. For each specific antigen, the optimal immunogenically effective amount should be determined experimentally (taking into consideration specific characteristics of a given patient and/or type of treatment). Generally, this amount is in the range of 0.01 μg-250 mg of an antigen. For certain exemplary adjuvant of the present invention, the immunogenically effective amount can be in the range of 10-250 μg of the adjuvant.

In some embodiments, a therapeutically effective amount of a therapeutic composition (i.e., an effective dosage) may range from about 0.001 μg/kg to about 250 g/kg, 0.01 μg/kg to 10 g/kg, or 0.1 μg/kg to 1.0 g/kg or about or at least: 0.001, 0.002, 0.003, 0.004, 0.005, 0.006, 0.007, 0.008, 0.009; 0.01, 0.02, 0.03, 0.04, 0.05, 0.06, 0.07, 0.08, 0.09; 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, or 250 grams or micrograms per kilogram of patient body weight, or any range between any of the numbers listed herein, or other ranges that would be apparent and understood by artisans without undue experimentation. The skilled artisan will appreciate that certain factors can influence the dosage and timing required to effectively treat a subject, including but not limited to the severity of the disease or disorder, previous treatments, the general health or age of the subject, and other diseases present.

In other embodiments, a therapeutically effective amount of Globo series moiety in the therapeutic composition (i.e., an effective dosage) may range from about 0.001 μg/kg to about 250 g/kg, 0.01 μg/kg to 10 g/kg, or 0.1 μg/kg to 1.0 g/kg or about or at least: 0.001, 0.002, 0.003, 0.004, 0.005, 0.006, 0.007, 0.008, 0.009; 0.01, 0.02, 0.03, 0.04, 0.05, 0.06, 0.07, 0.08, 0.09; 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, or 250 grams or micrograms per kilogram of patient body weight, or any range between any of the numbers listed herein, or other ranges that would be apparent and understood by artisans without undue experimentation. The skilled artisan will appreciate that certain factors can influence the dosage and timing required to effectively treat a subject, including but not limited to the severity of the disease or disorder, previous treatments, the general health or age of the subject, and other diseases present. In one embodiment, the immunogenically effective amount of a pharmaceutically acceptable carrier comprising the vaccine ranges from about 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.25, 1.5, 1.75, 2.0, 2.25, 2.5, 2.75, 3.0, 3.25, 3.5, 3.75, 4.0, 4.25, 4.5, 4.75 to about 5.0 or any range between any of the numbers listed herein.

In some embodiments, the therapeutic compositions of the invention are administered to a subject in need thereof (e.g., one having a cancer such as breast cancer) in a method that on average extends progression free survival or overall survival over a control placebo, e.g., a phosphate buffered saline placebo, by about or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 days, weeks, months, or years.

EXAMPLES

The exemplary SSEA-4 hexasaccharide portion of the therapeutic compositions of the invention was chemically synthesized as the allyl glycoside and then prepared for conjugation with KLH or diphtheria toxin cross-reacting material 197 (DT-CRM 197).

Example 1: Preparation of Exemplary Glycoconjugate of the Invention (SSEA-4-KLH and SSEA-4-DT)

In one illustrative embodiment, the chemical synthesis of exemplary SSEA-4-KLH involves the following general steps:

SSEA-4-NH$_2$ preparation: Exemplary sample was prepared by adding 10 mg SSEA-4 antigen with 5.0 equiv. p-nitrophenyl ester in 1.5 μL triethylamine (NEt3). After incubating at 30° C. for 1.5 hours, SSEA-4 was quenched in 300 μL 1% Acetic Acid. Finally the SSEA-4 antigen was filtrated through 0.22 μm filter and lyophilized in 0.1% Acetic Acid.

SSEA-4-KLH conjugation: The lyophilized SSEA-4-NH$_2$ was dissolved in DMF and mixed with KLH (dissolved in phosphate buffered saline solution, PBS) at pH 8.0. After incubating at room temperature for 16 hours, the SSEA-4-KLH mixture was purified by MAP-TFF system and exchanged the storage buffer from DMF to PBS.

In one illustrative embodiment, the chemical synthesis of SSEA-4-DT involves the following general steps:

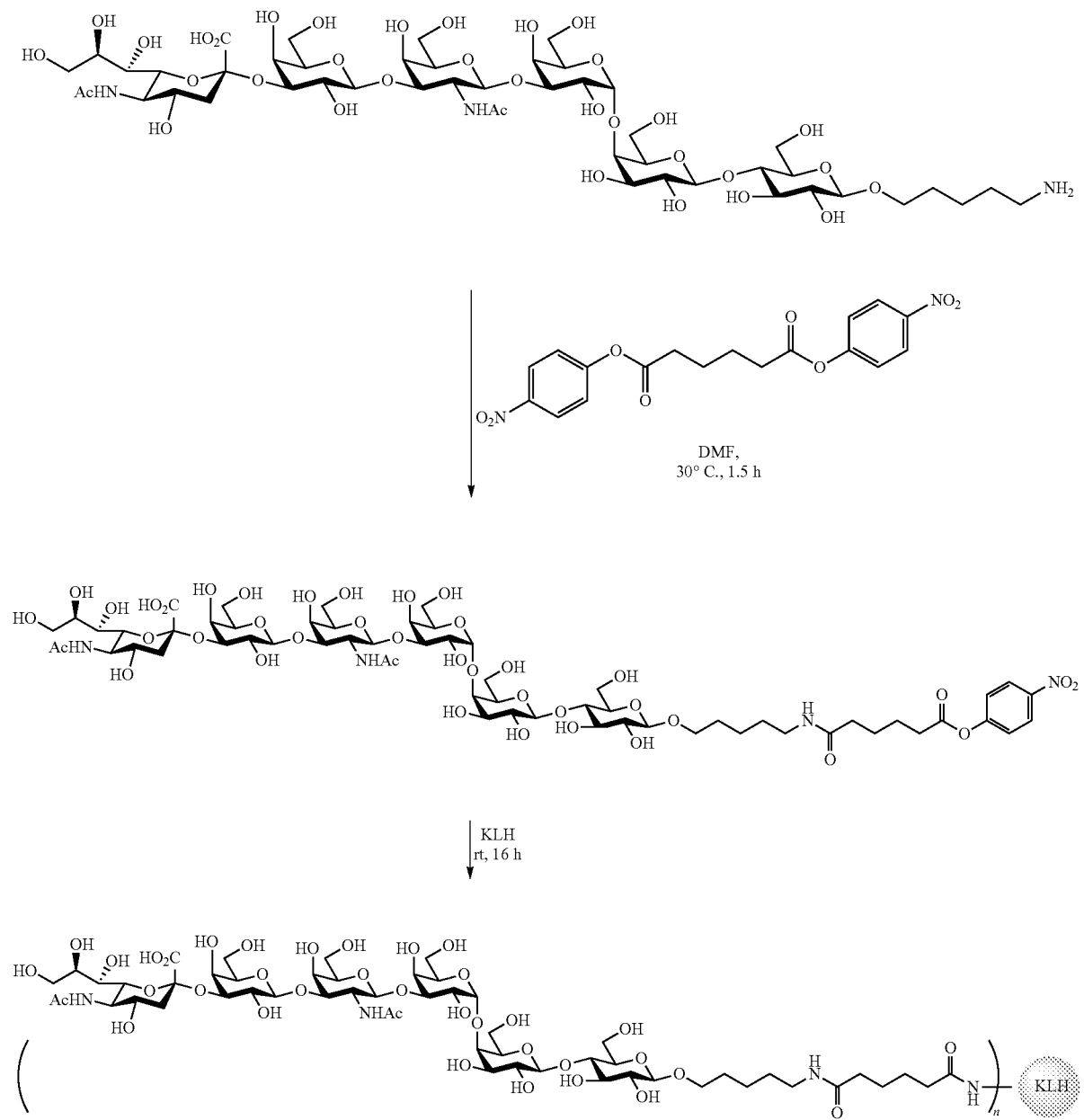

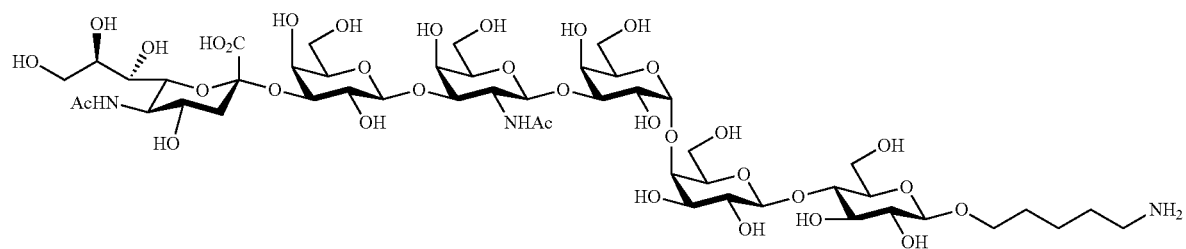
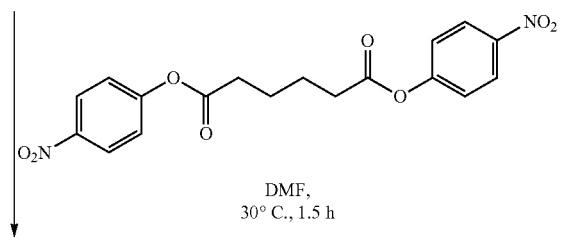
DMF,
30° C., 1.5 h
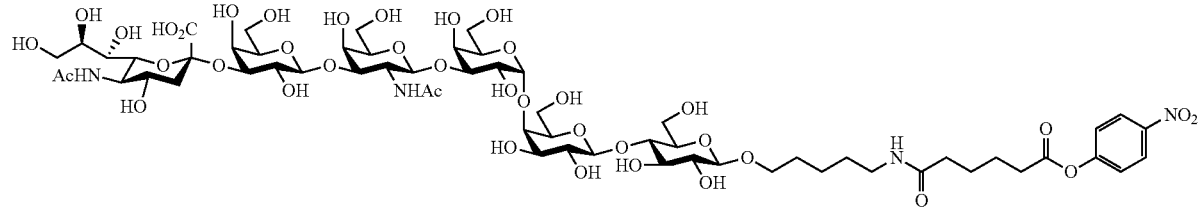
CRM-197
rt, 20 h
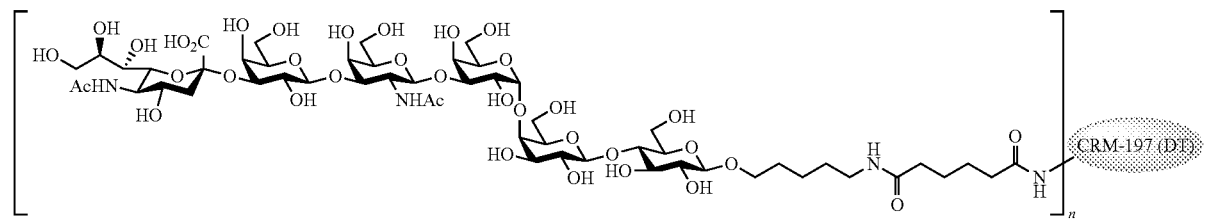

SSEA-4-NH$_2$ preparation: Exemplary sample was prepared by adding 10 mg SSEA-4 antigen with 5.0 equiv. p-nitrophenyl ester in 2 μL triethylamine (NEt3). After incubating at 30° C. for 1.5 hours, SSEA-4 was quenched in 300 μL 1% Acetic Acid. Finally the SSEA-4 antigen was filtrated through 0.22 μm filter and lyophilized in 0.1% Acetic Acid.

SSEA-4-DT conjugation: The lyophilized SSEA-4-NH$_2$ linker was dissolved in DMF and mixed with diphtheria toxin cross-reacting material 197 (DT-CRM 197) (dissolved in phosphate buffered saline solution, PBS) at pH 9.5. After incubating at room temperature for 20 hours, the SSEA-4-DT mixture was purified by MAP-TFF system and exchanged the storage buffer from DMF to PBS. The summary of SSEA-4-DT and SSEA-4-KLH compositions were shown in Table 3.

TABLE 3

The summary of SSEA-4-DT and SSEA-4-KLH glycoconjugate

|  | SSEA-4-DT (Lot No. LN-0189037) | SSEA-4-KLH (Lot No. RD-BK-160707-01) |
|---|---|---|
| Number of Lysine | 39 | 3000 |
| Protein concentration | 2.8 mg/mL | 3.09 mg/mL |
| Carbohydrate concentration | 0.376 mg/mL | 0.277 mg/mL |
| Epitope Ratio | 6.75 | 665 |

TABLE 3-continued

The summary of SSEA-4-DT and SSEA-4-KLH glycoconjugate

|  | SSEA-4-DT (Lot No. LN-0189037) | SSEA-4-KLH (Lot No. RD-BK-160707-01) |
|---|---|---|
| Molecular Weight | Monomer: 65.36 kDa | ≤3 mer: 68.5%<br>10 mer: 30.58%<br>≥20 mer: 0.92% |

Example 2: Preparation of Glycoconjugate of the Invention (SSEA-4-MCCa-KLH, Globo H-MCCa-KLH and SSEA-3-MCCa-KLH)

1. General Procedure to Prepare Exemplary Sugar-MCCa Compounds

The amine substrates (Globo H-pantyl amine, SSEA-3-pantyl amine, or SSEA-4-pantyl amine), MCCa-OSu and DIPEA were mixed in DMF at ambient temperature. The reaction crude was stirred for 2 hours. After reaction completed assessed by TLC, monitoring, the reaction was then cooled, neutralized, and quenched by water. The resulted mixture was then added on a pad of RPC18 gel for purification. After chromatography purification through RPC18 gel, the collected fractions were concentrated by rota-evaporator and high-vacuum system to afford the expected sugar-MCCa compound as white solid. The yield is around 65~80%.

Preparation of SSEA-4-MCCa

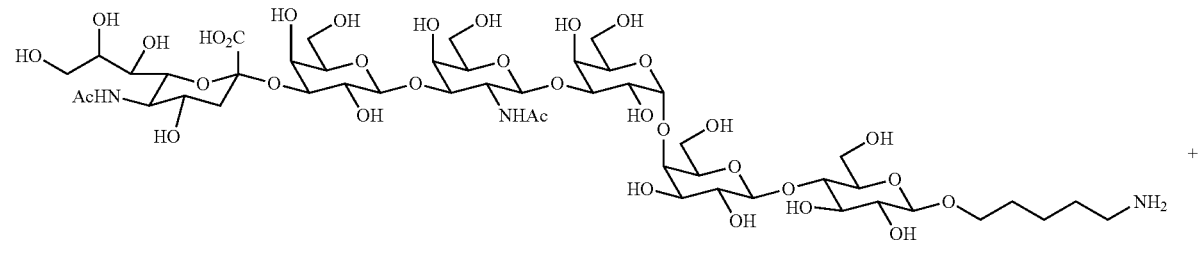

SSEA4-Pentyl amine

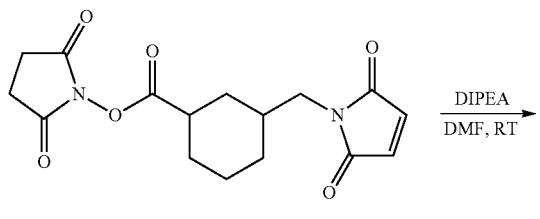

MCCa-OSu

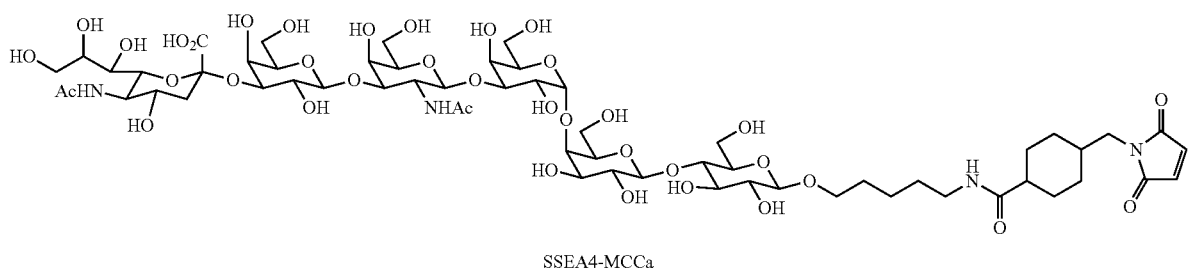

SSEA4-MCCa

-continued
Preparation of Globo H-MCCa
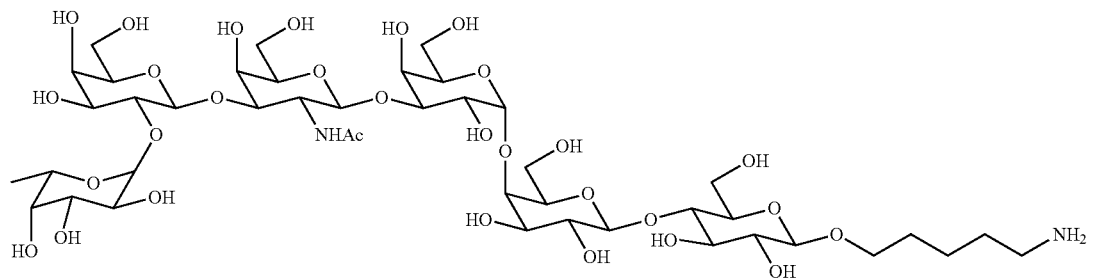
Globo H-Pentyl amine
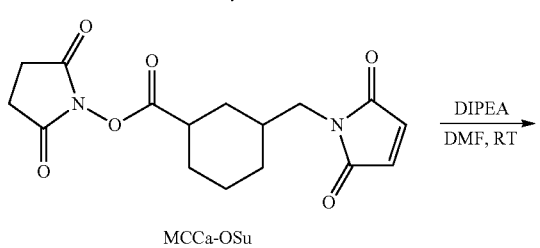
MCCa-OSu
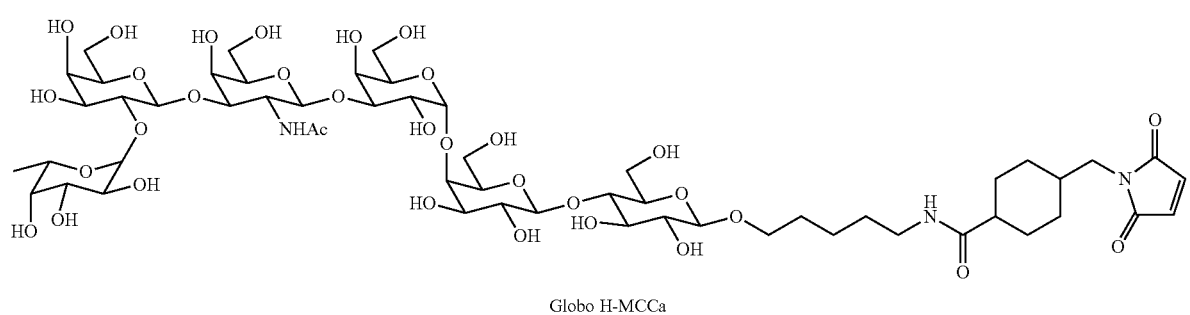
Globo H-MCCa
Preparation of SSEA-3-MCCa
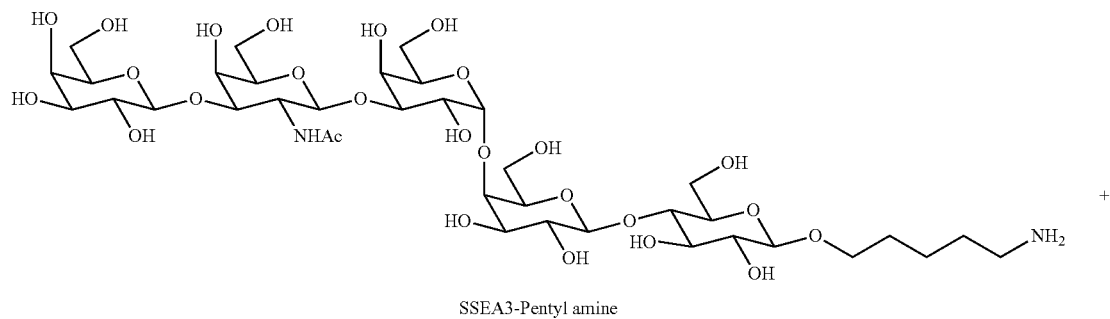
SSEA3-Pentyl amine
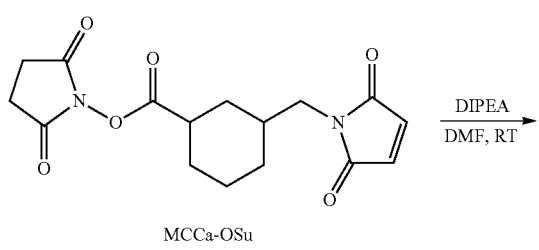
MCCa-OSu

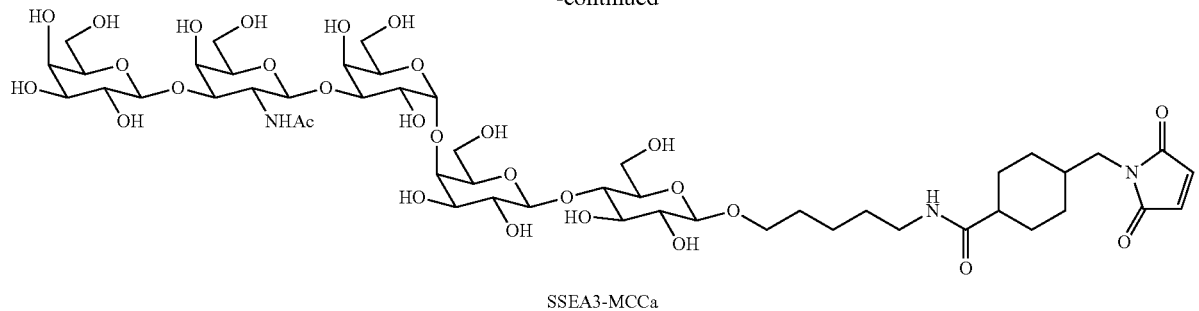

SSEA3-MCCa

2. General Procedure to Prepare Exemplary Sugar-MCCa-KLH Conjugated Products

KLH is chemically modified into a modified-KLH intermediate, and then conjugate to the sugar-MCCa to afford the crude sugar-MCCa-KLH conjugated product in a low oxygen level environment.

Step 1. Thiolation of KLH

The buffer-exchanged KLH was purged with inert gas. After purging, 2-iminothiolane hydrochloride (2-IT) is added into the KLH under inert gas protection. The reaction was stirred at 18° C. for 35 min. After stirring for 35 min, the reaction crude was quickly loaded onto the prepared G-15 column for column chromatography purification. The collected fractions were sampled and tested by BCA plot and Ellman plot to confirm the product. The pooled protein intermediate modified-KLH was soon sampled for Ellman assay and BCA assay to determine the SH value and protein content. PBS buffer was added into the collected modified KLH to adjust the concentration of protein to about 0.6~1.0 mg/mL.

Step 2. Conjugation of Intermediate

The prepared intermediate compound (sugar-MCCa) was dissolved in PBS buffer. This intermediate was sequentially transferred into the modified-KLH bottle. Add PBS buffer solution to rinse the sugar bottle, and then transfer this solution into the conjugation reaction. After mixing, the reaction crude was sampled at first half hour, and the following 1 hour, 1.5 hour, 2 hour, and 3 hour to monitor the #SH value. When the #SH value was lower than 200, the sugar-MCCa-KLH conjugate was stored in a freezer for next operation stage.

Step 3. Purification to Afford the Expected Sugar-MCCa-KLH Conjugated Products

The sugar-MCCa-KLH crude was purified by filtration of TFF system filtration or centrifuge using pH 7.2 PBS for 10 times volume. The filtrate solution was collected, and sampled for HPLC analysis. The purified sugar-MCCa-KLH was temporally stored in freezers for further release tests.

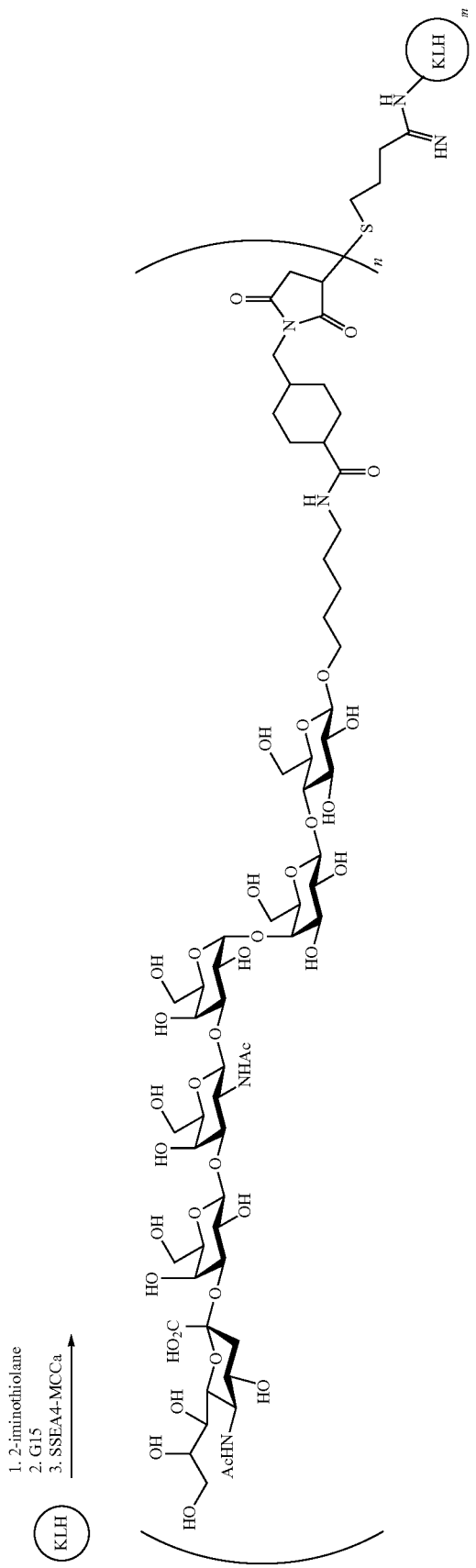

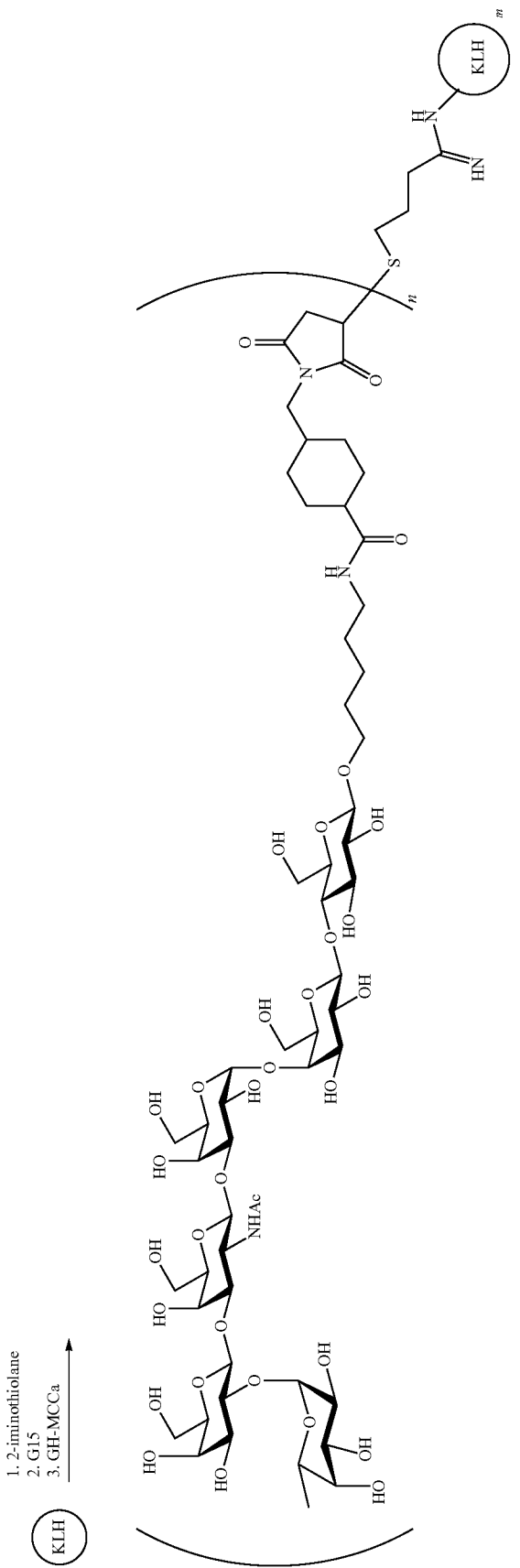

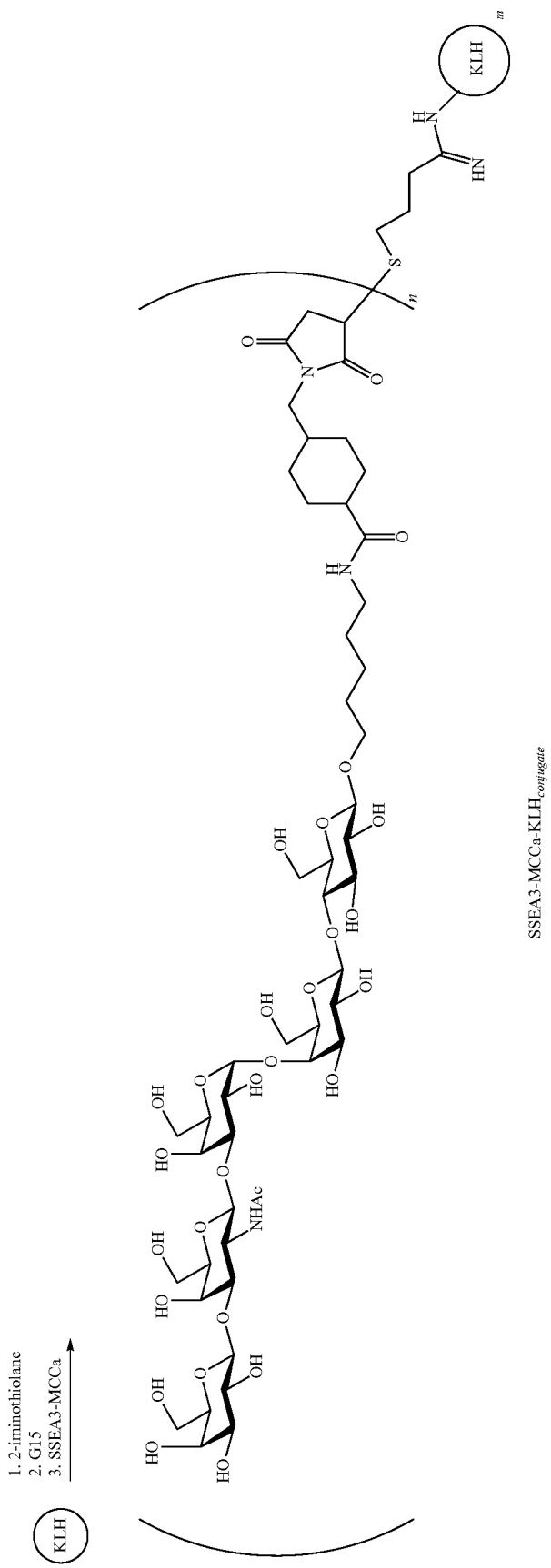

Example 3: Analysis of Epitope Ratio of Exemplary Globo-Series Antigens (SSEA-4, Globo H and SSEA-3) to KLH in the Glycoconjugate The molecular weight of a KLH didecamer (the naturally aggregated form) is approximately 7.5 MDa~8.6 MDa. The native KLH was confirmed with the molecular weight of approximately 8.6 MDa.

Figure 2A:
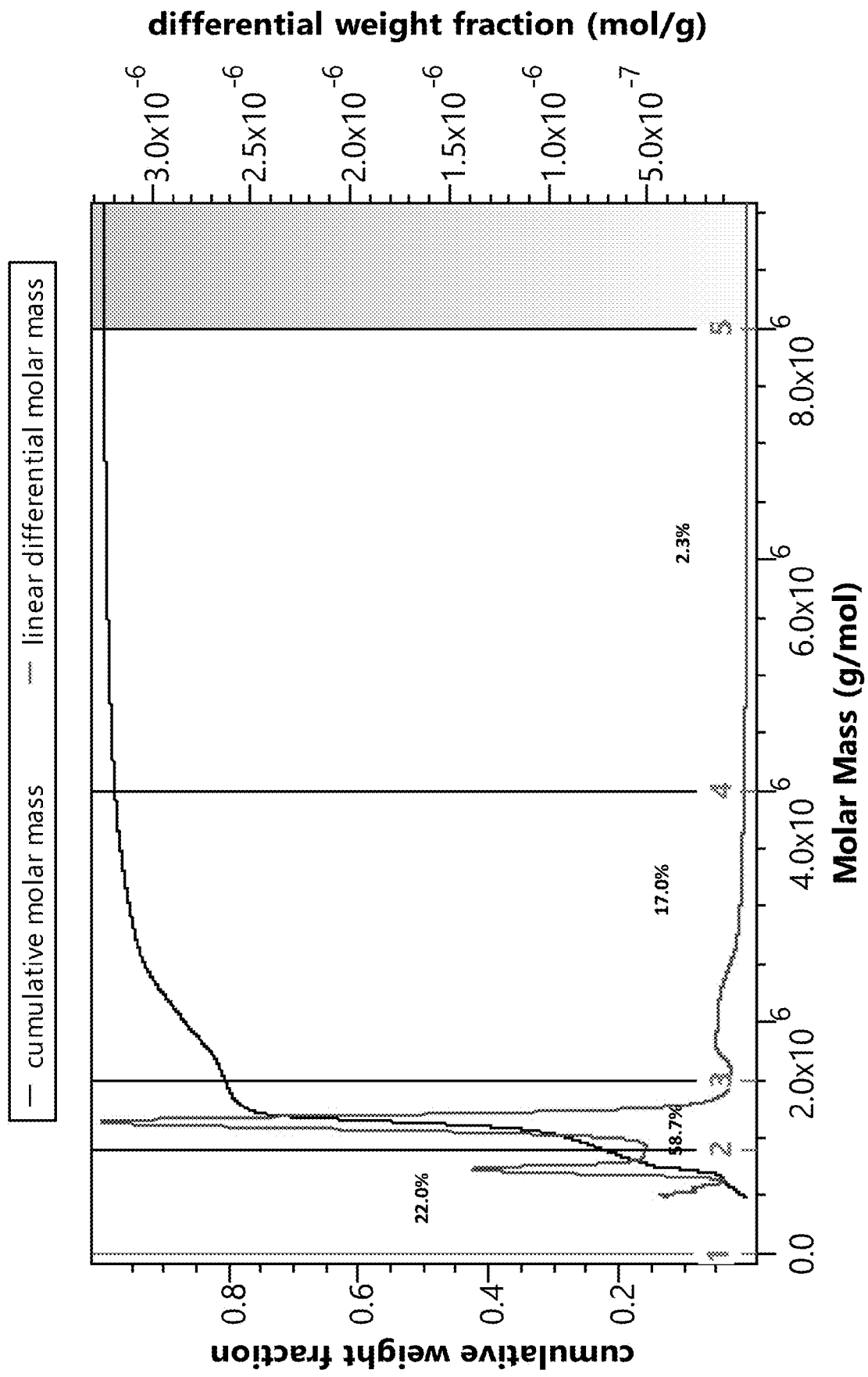
FIG. 2A shows the mass distribution analysis of SSEA-4-KLH glycoconjugate using SEC-MALS.
Figure 2B:
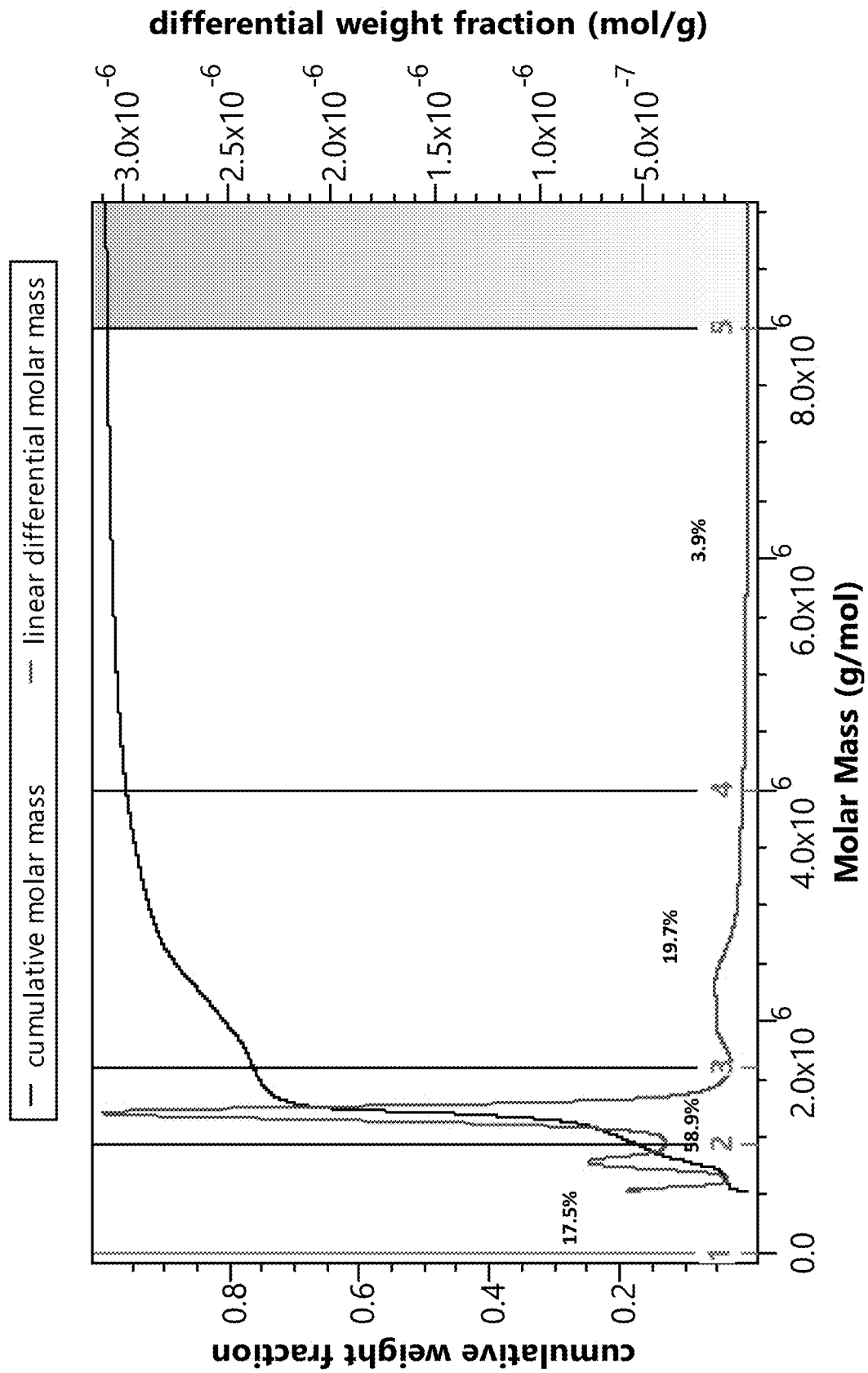
FIG. 2B shows the mass distribution analysis of Globo H-KLH glycoconjugate using SEC-MALS.
Figure 2C:
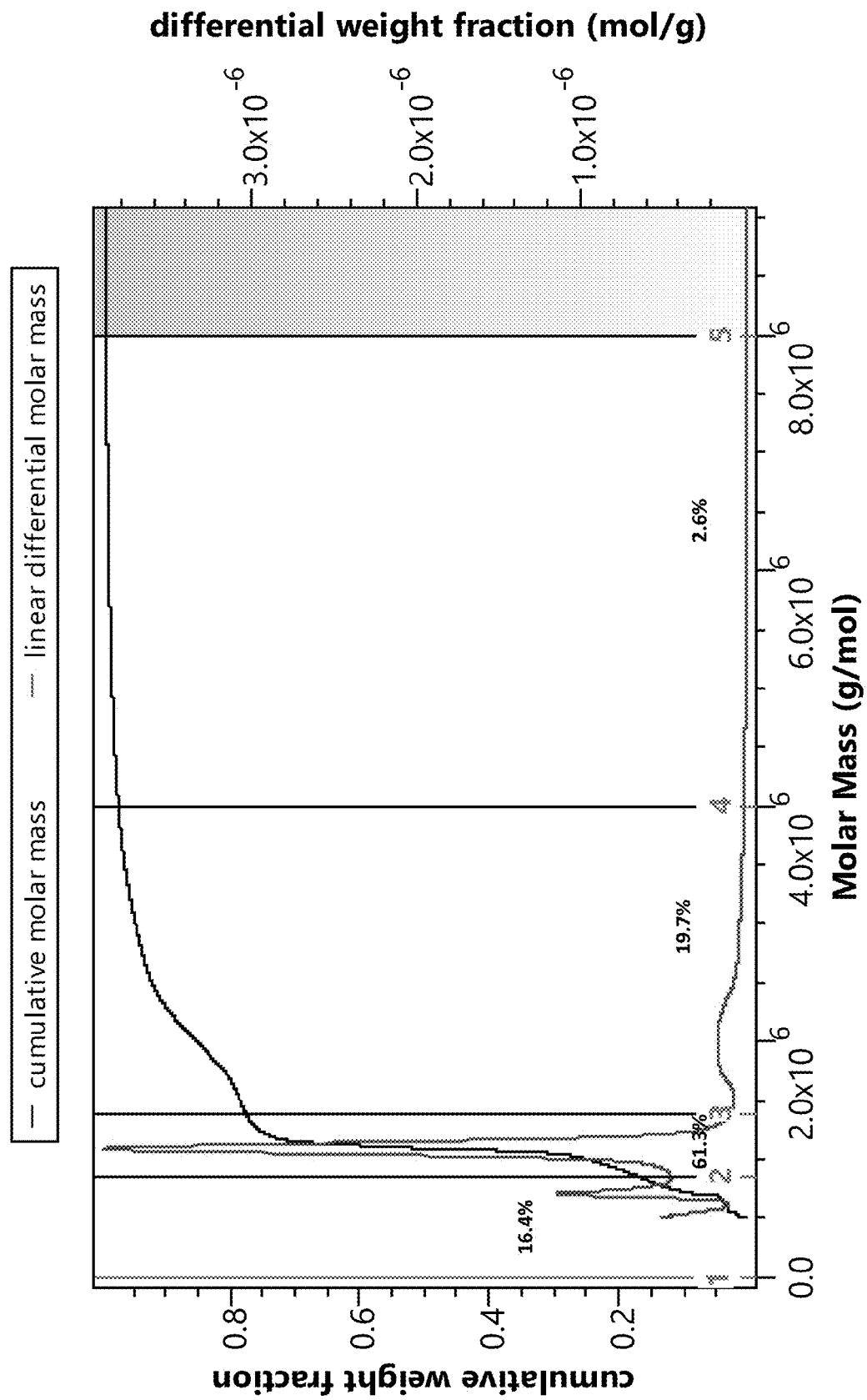
FIG. 2C shows the mass distribution analysis of SSEA-3-KLH glycoconjugate using SEC-MALS.

The mass distribution of KLH and Globo series antigen-KLH glycoconjugates (SSEA-4-MCCa-KLH, Globo H-MCCa-KLH and SSEA-3-MCCa-KLH) were estimated and derived by size exclusion chromatography using multi-angle laser scattering spectrometer (SEC-MALS). In FIG. 1A, multimer (n>7-20) and oligomer (n>20) of KLH were observed. FIG. 1B showed the peak area of didecamer was 78.48% and multi-decamer was 20.31%. The average observed Molecular Weight (MW) of KLH was 7476 kDa. FIG. 2A showed trimer (n=3) was the major component (58.7%) of SSEA-4-MCCa-KLH glycoconjugate. Similarly, FIG. 2B (Globo H-MCCa-KLH glycoconjugate) and FIG. 2C (SSEA-3 MCCaKLH glycoconjugate) also showed trimer (n=3) was the major component in Globo H-MCCa-KLH glycoconjugate (58.9%) and SSEA-3-MCCa-KLH glycoconjugate (61.3%). The summary of Globo series antigens conjugated KLH vaccine was shown as in Table 4.

Example 4: Preparation of Exemplary Globo Series Antigens Glycoconjugates Vaccine for Immunization in Mice

TABLE 4

Batch analysis summary of representative exemplary Globo series antigens conjugated KLH vaccine

| | Name (Lot No.) | | |
|---|---|---|---|
| | SSEA-4-MCCa-KLH (RD-BK-170323) | Globo H-MCCa-KLH (RD-BK-170307) | SSEA-3-MCCa-KLH (RD-BK-170317) |
| Number of Lysine | 3000 | 3000 | 3000 |
| Protein Conc. | 2.54 mg/mL | 2.85 mg/mL | 2.00 mg/mL |
| Carbohydrate Conc. | 0.498 mg/mL | 0.657 mg/mL | 0.313 mg/mL |
| Epitope Ratio | 1459 | 1953 | 1552 |
| Oligomer Distribution | 1-2 mer: 22.0% | 1-2 mer: 17.5% | 1-2 mer: 16.4% |
| | 3 mer: 58.7% | 3 mer: 58.9% | 3 mer: 61.3% |
| | 4-8 mer: 17.0% | 4-8 mer: 19.7% | 4-8 mer: 19.7% |
| | ≥10 mer: 2.3% | ≥10 mer: 3.9% | ≥10 mer: 2.6% |

Six to eight weeks-old female C57BL/6 mice were obtained from BioLasco and conducted the studies at Level Biotech Inc. and Eurofins Panlabs for single valent, bi-valent or tri-valent vaccine potency assay, respectively. At least one day before dosing, animals will be selected into study groups by a randomization process based on body weight and each group contains five mice.

Afterwards, the Globo series antigens glycoconjugates (Globo H-KLH, SSEA-3-KLH, SSEA-4-KLH/DT) and adjuvants (OBI-821 or OBI-834) were subcutaneously (s.c) administrated into both left and right abdominal sites (0.5-5 μg; 100 μL/site) of mice at Day 0, 7, 14, 21 (using 20 μg OBI-821 adjuvant) or Day 0, 14, 28 (using 40 μg OBI-834 adjuvant). The whole-blood samples will be collected at the following time points during the study (using OBI-821 adjuvant): pre-immune (Day 0, before dosing), Day 10, 17, 24, and 31. The blood specimens will be taken via submandibular collection during the study and use cardiac puncture for the last time point Day 43 blood harvest. For the OBI-834 adjuvant, the whole-blood samples will be collected at pre-immune (Day 0, before dosing), Day 21, 28, 38 and 50. The blood will be collected without adding anticoagulant and proceed to serum by centrifuged at 1,500 g at 4° C. for 15 minute. The resultant serum specimens will be transferred to specimen collection tube and stored at below −60 to −80° C. for subsequent potency assay determined by glycan array assay.

Example 5: Glycan Array Assay

The exemplary testing platform in the present disclosure utilized Agnitio BioIC system (Analyzer BA-G2012, Cat #A12101 and pumping machine (Pumping Machine BA-G2012, Cat #A15101) which performed an automatically ELISA reaction within a microfluidic cartridge. Each cartridge contained an array of microfluidic pumps and valves, a channel network, reagent storage reservoirs, a glycan array reaction zone, and a waste storage reservoir. To perform the test, all reagent and test sample were pumped sequentially, from their respected reservoirs in to a reaction zone containing the glycan microarray in order to carry out a multiplexed ELISA reaction with chemical luminescence. The result data was captured simultaneously and data analysis was performed by the LabIT software provided by Agnitio Science and Technology Inc. The specification of equipment of Agnitio BioIC system suitably configured according to the present disclosure was reported in PCT patent application (WO2017041027A1).

Exemplary Experimental Materials:
1. Sample Diluent (BioCheck, Cat #MB10175).
2. OBI-868 Glycan Chip kit (Agnitio, Cat #MG03-IgG, MM03-IgM) with Glycan chips, Blocking Buffer (Protein-Free Blocking Buffers, Thermo Fisher Scientific Inc., Cat #37571), Conjugate Buffer, Wash Buffer [Phosphate-buffered saline (Thermo Fisher Scientific Inc., Cat #70011) plus 0.2% (vol/vol) Tween 20 (J.T. Baker, Cat #JTB-X251-07)], Substrate Buffer (A) and Substrate Buffer (B) [SuperSignal ELISA Femto Maximum Sensitivity Substrate, Thermo Fisher Scientific Inc., Cat #37074]. The glycan chips were coated with SSEA-4, SSEA-3 or Globo H, separately.
3. Secondary Antibody: Goat anti-mouse IgG-HRP (KPL, Cat #474-1806) or Goat anti-mouse IgM-HRP (KPL, Cat #074-1803).

Reagent Preparation:
1. For each serum/plasma sample, 100-fold dilution was prepared by adding 2.5 μL of the sample to 247.5 μL of Sample Diluent, mix well. (Sample dilution fold: 50×, 100×, 200×, 300×, 1,000× and 10,000×). If any of the anti-Globoseries IgG/IgM mean intensity exceeds the highest point of the internal standard curve, prepare 1,000 fold and/or 10,000 fold dilution of the sample.

2. Secondary Antibody Solution: serial dilutions of the secondary antibody were prepared using the Conjugate Buffer as described below table. Samples were mixed well between each addition/dilution.

TABLE 5

Secondary Antibody Solution preparation

| $2^{nd}$ Antibody | Dilution | Take from sample | Antibody (µL) | Conjugate Buffer (µL) | Final volume (µL) |
|---|---|---|---|---|---|
| Anti-mouse IgG-HRP | 1000x | Stock (1x) | 2 | 1998 | 2000 |
| Anti-mouse IgM-HRP | 50x | Stock (1x) | 2 | 98 | 100 |
|  | 3000x | 50x | 30 | 1770 | 1800 |

3. Substrate Preparation: For each chip, sample was prepared with aliquot 65 µL of both Substrate Buffer (A) and (B), mix well. The mixed Substrates should be freshly prepared before each testing.

Assay procedure: Six hundred and twenty microliter Wash Buffer was added in the "Wash" hole of array. Next, 120 µL Blocking Buffer was added in the "Blocking" hole of array. At this point, 120 µL Secondary Antibody Solution and 100 µL serum were added in the "Conjugate" and "Serum" hole of array, separately. At the last, 120 µL mixed Substrate Buffer was added in the "Substrate" hole of array in ten minutes. The glycan array was put on the Agnitio BioIC Pumping Machine for pressurizing 30 minutes. The bound serum was visualized monitored using Agnitio BioIC Analyzer.

Data Analysis was Performed by the Following Steps:

1. Generate the internal curve by plotting the average intensity obtained for each IgG/IgM concentration on the Y-axis and total IgG/IgM concentration (µg/mL) on the X-axis. The internal curve $R^2$ must be >0.95.

2. Calculate the mean intensity for each set of internal curve and anti-Globo series IgG/IgM of the chip (anti-SSEA-4, anti-SSEA-3 or anti-Globo H). The mean intensity of anti-Globo series IgG/IgM must not exceed the highest point of the internal curve.

3. Calculate antibody intensity in the unknown sample by plugging in the measured intensity (Y-axis) to the internal curve using Microsoft Excel® or equivalent application.

4. For diluted samples, compensate by multiplying the concentration with dilution factor to obtain actual IgG/IgM concentration in the sample.

5. Calculate and report the relative IgG/IgM concentration by following formula: Relative IgG/IgM concentration (µg/mL)=Calculated IgG/IgM concentration×0.1

Results

1. Single Valent Vaccine Potency Assay (SSEA-4-KLH or SSEA-4-DT Combined with OBI-821 or OBI-834 Adjuvant)

Figure 3B:
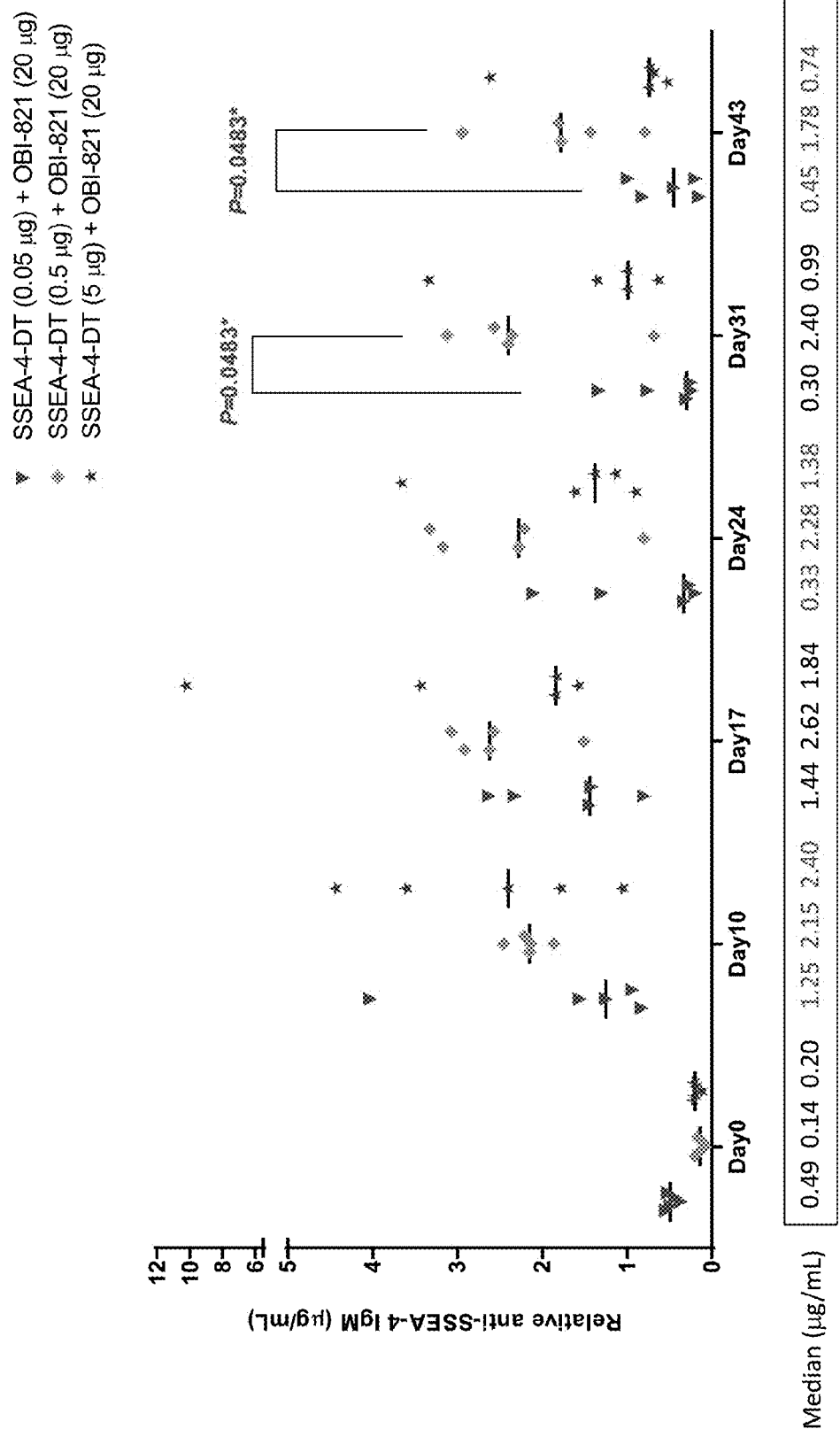
Figure 3D:
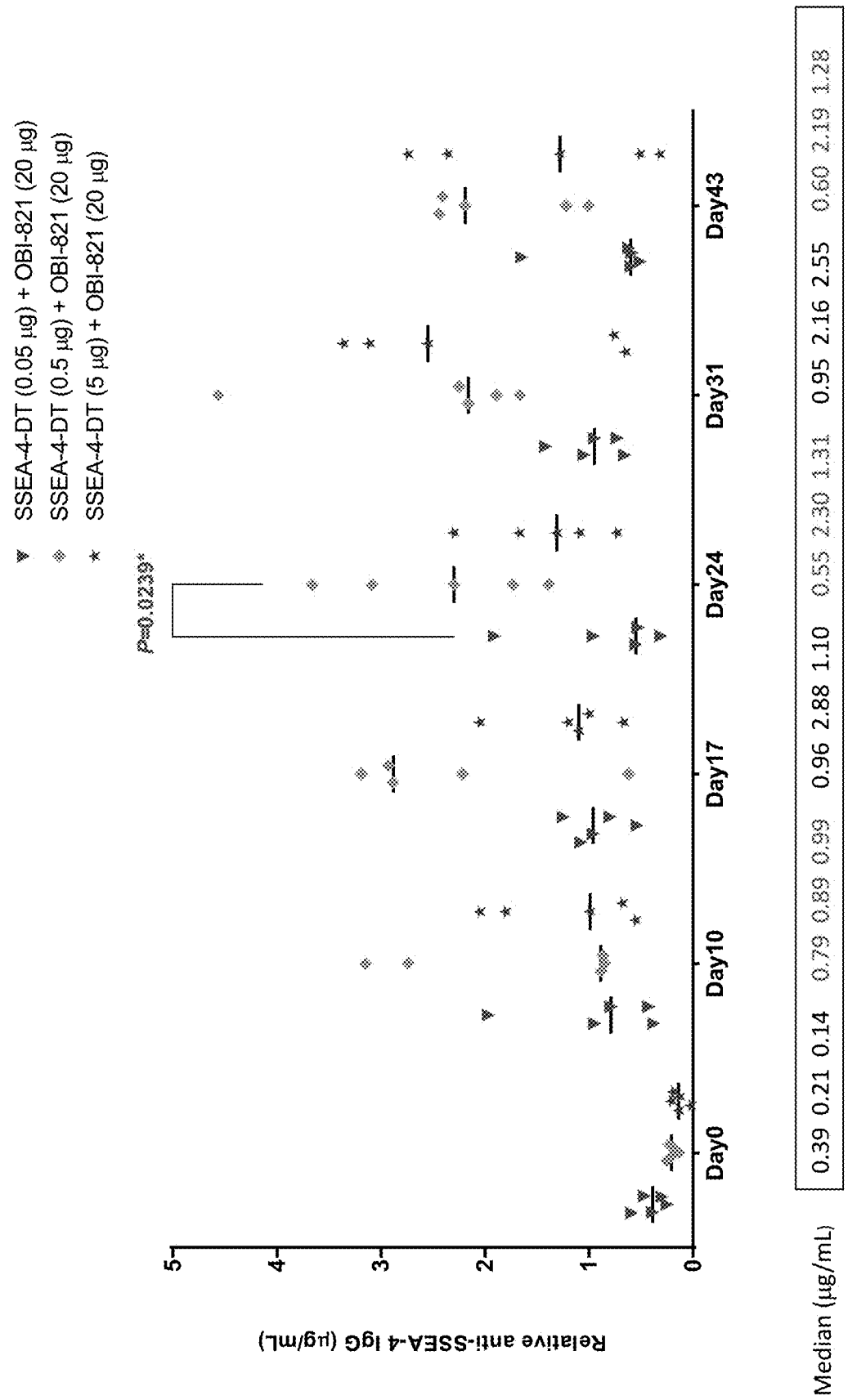
Figure 4A:
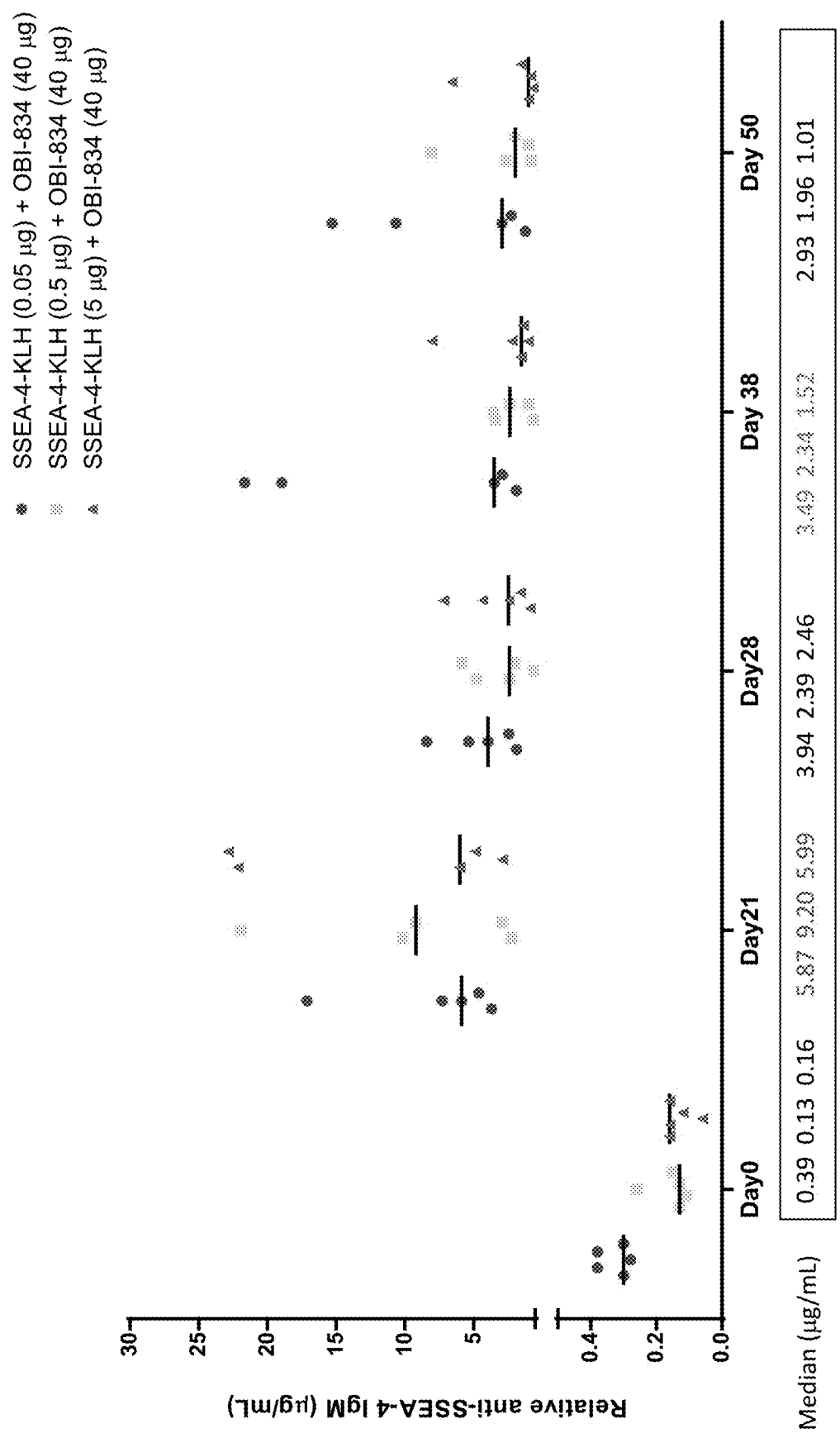
FIG. 4A and FIG. 4B show the result of Anti-SSEA-4 IgM level and median concentration from five individual mouse induced by different doses of SSEA-4-KLH and SSEA-4-DT single valent vaccine with OBI-834 adjuvant.
Figure 4B:
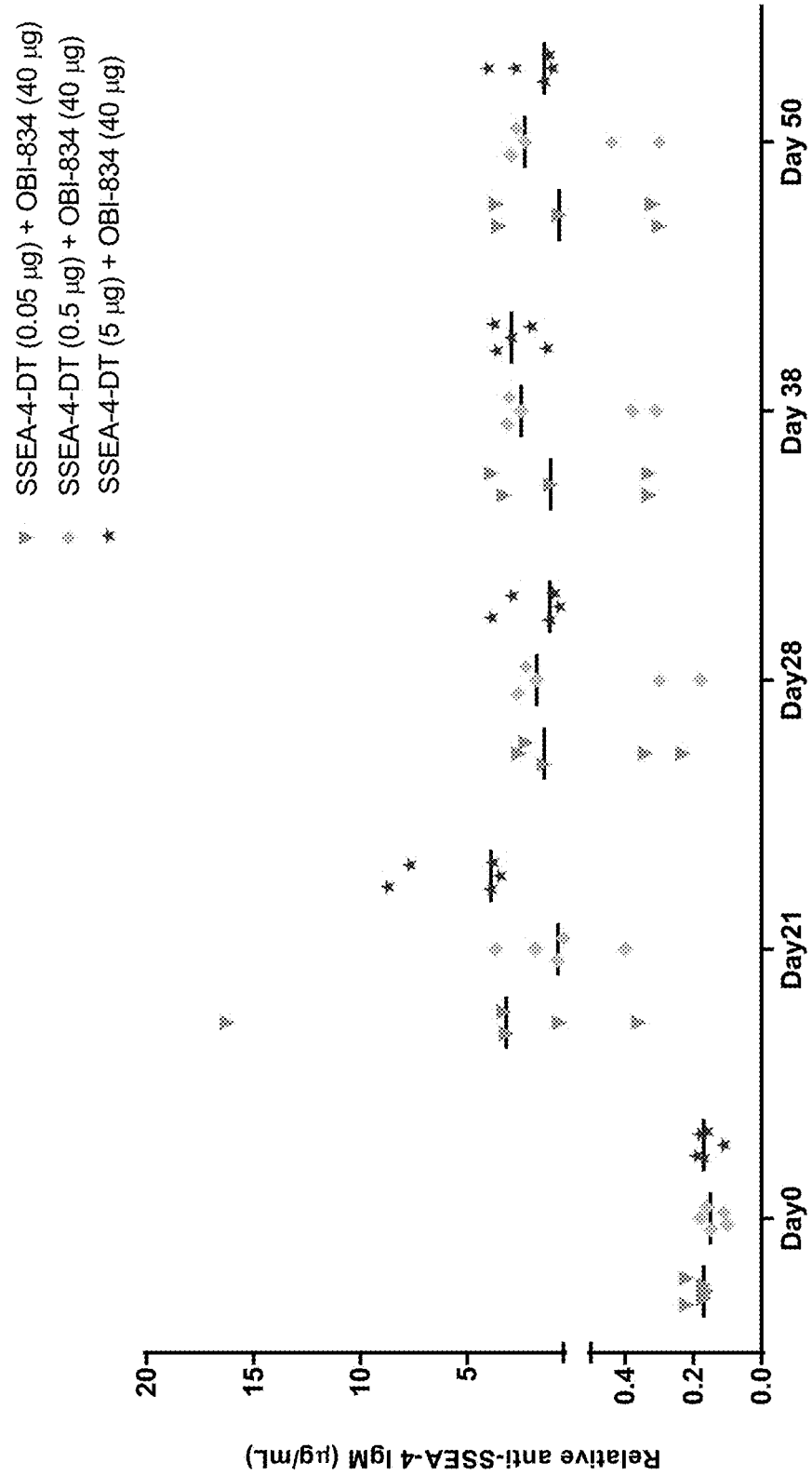
Figure 4C:
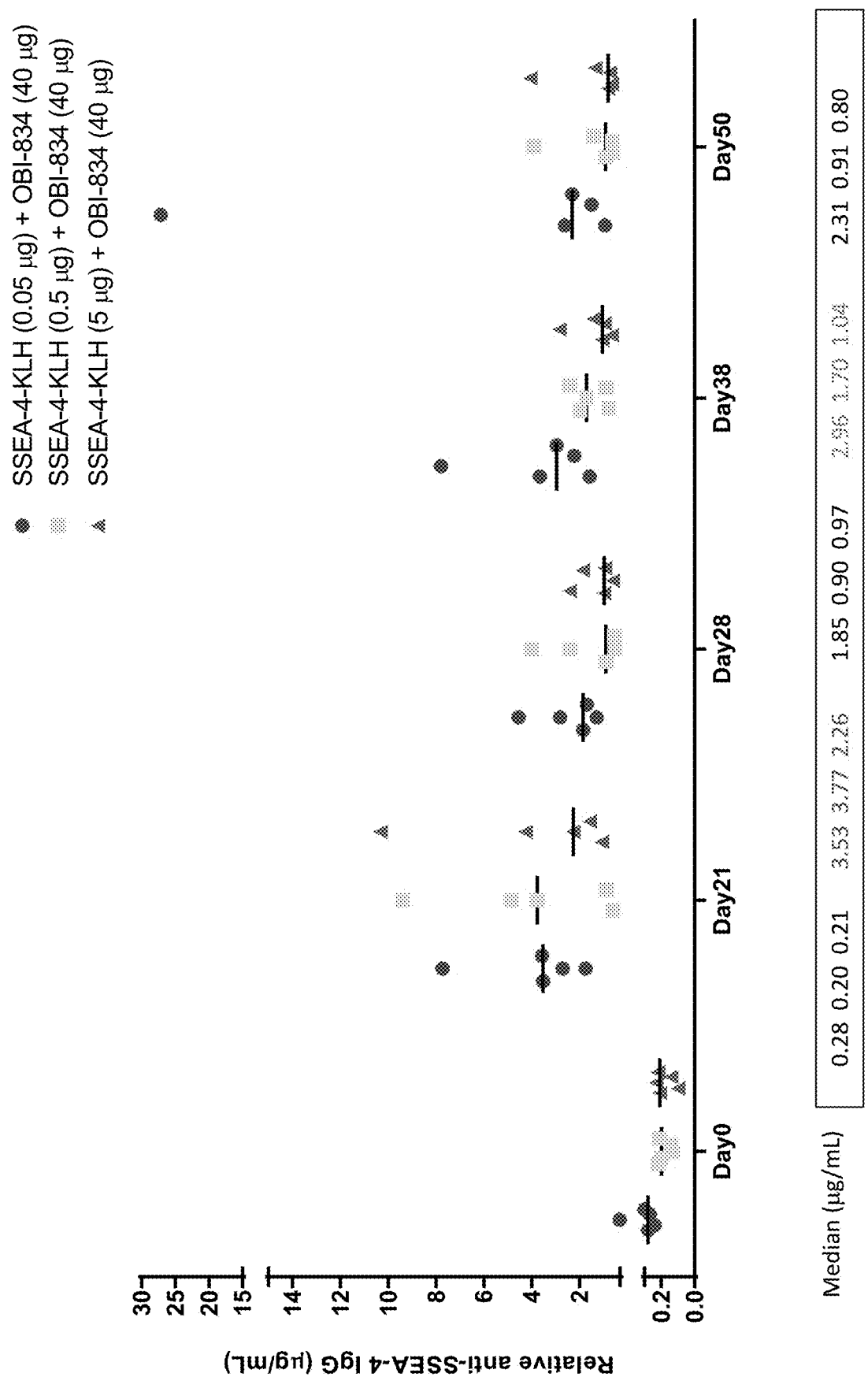
FIG. 4C and FIG. 4D show the result of Anti-SSEA-4 IgG levels induced by different doses of SSEA-4-KLH and SSEA-4-DT single valent vaccine with OBI-834 adjuvant.
Figure 4D:
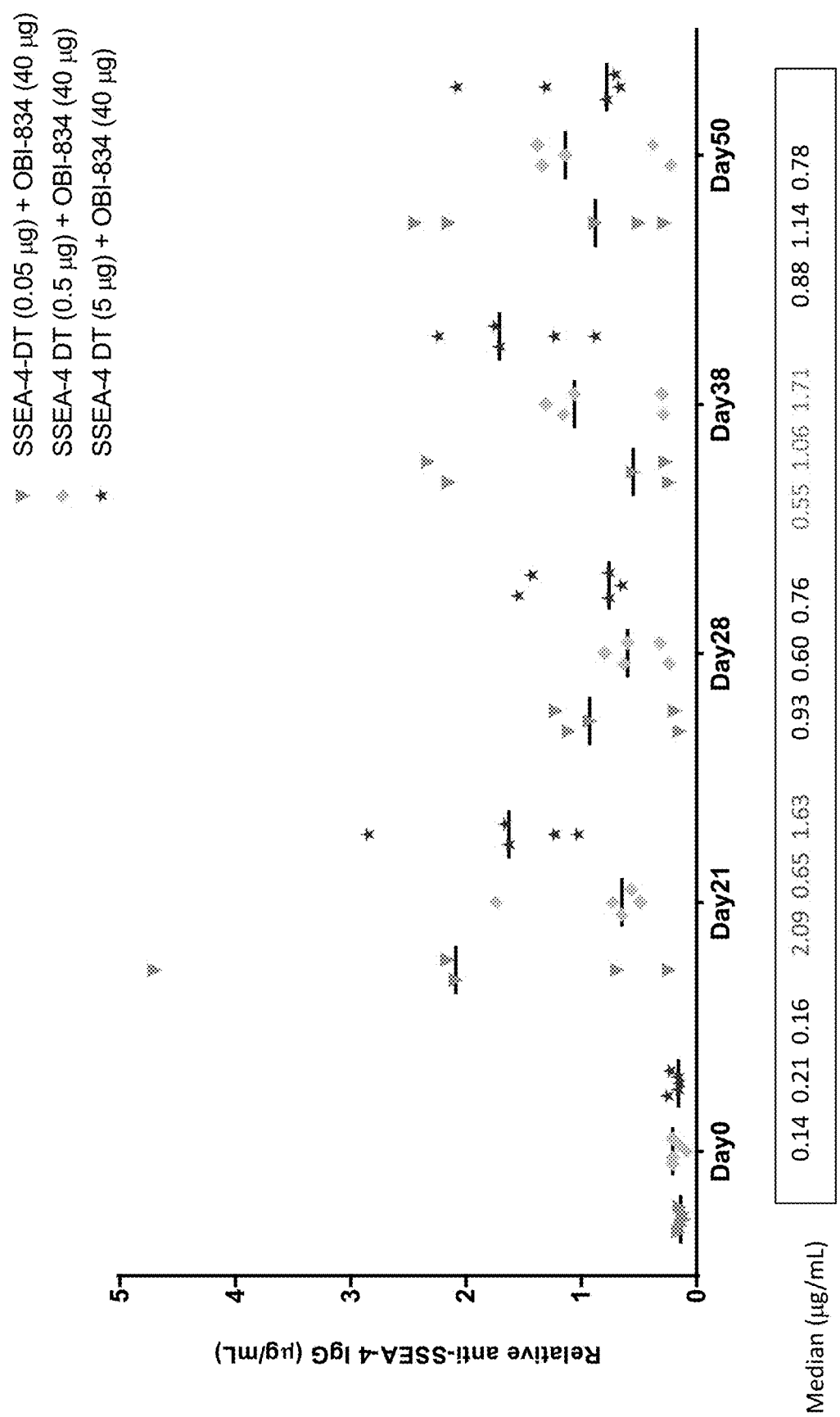
Figure 5A:
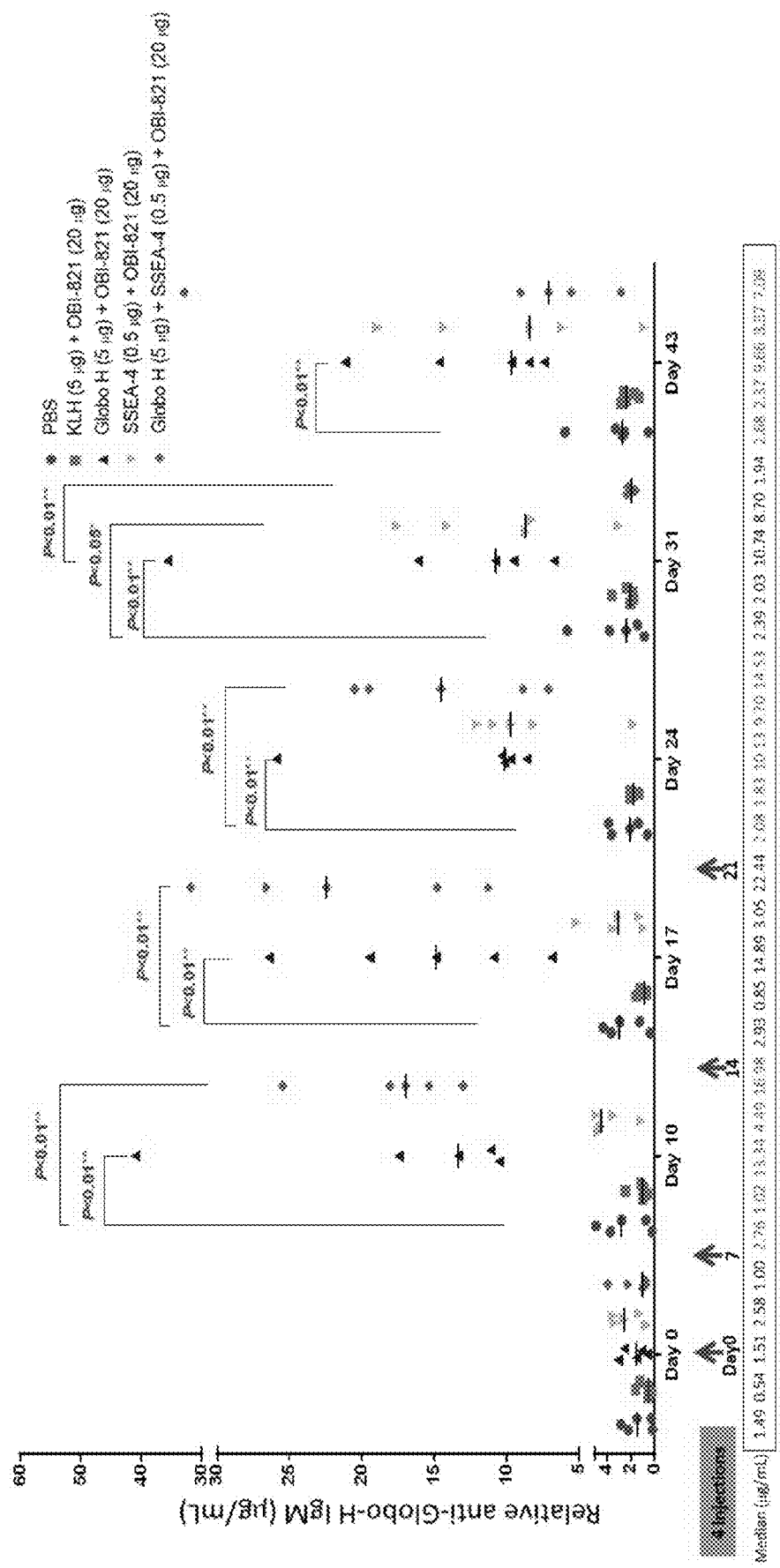
FIGS. 5A through 5F show the immunogenicity result induced by bi-valent vaccine (SSEA-4-KLH combined with Globo H-KLH glycoconjugate) with OBI-821 adjuvant.
Figure 5B:
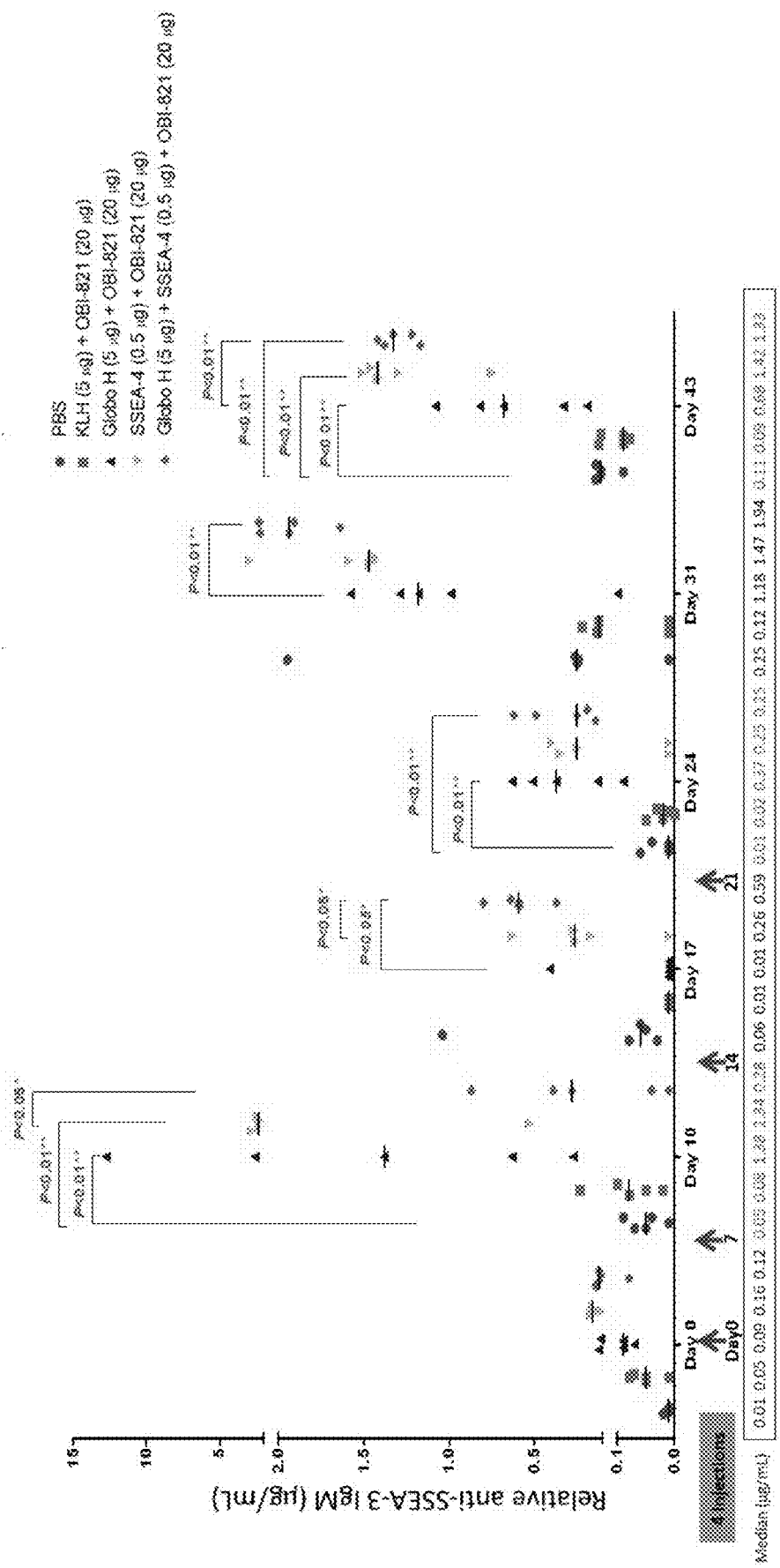
Figure 5C:
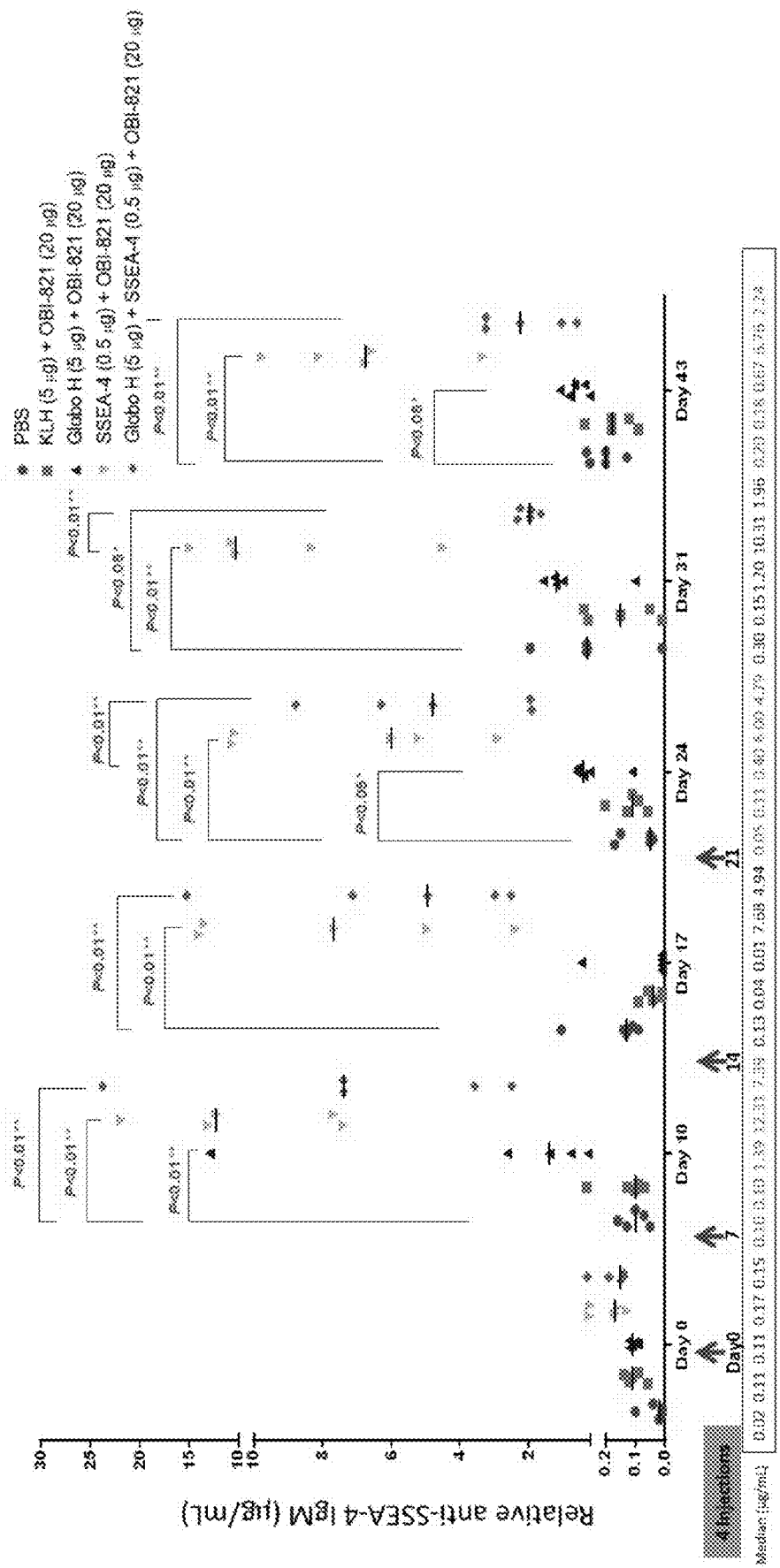
Figure 5D:
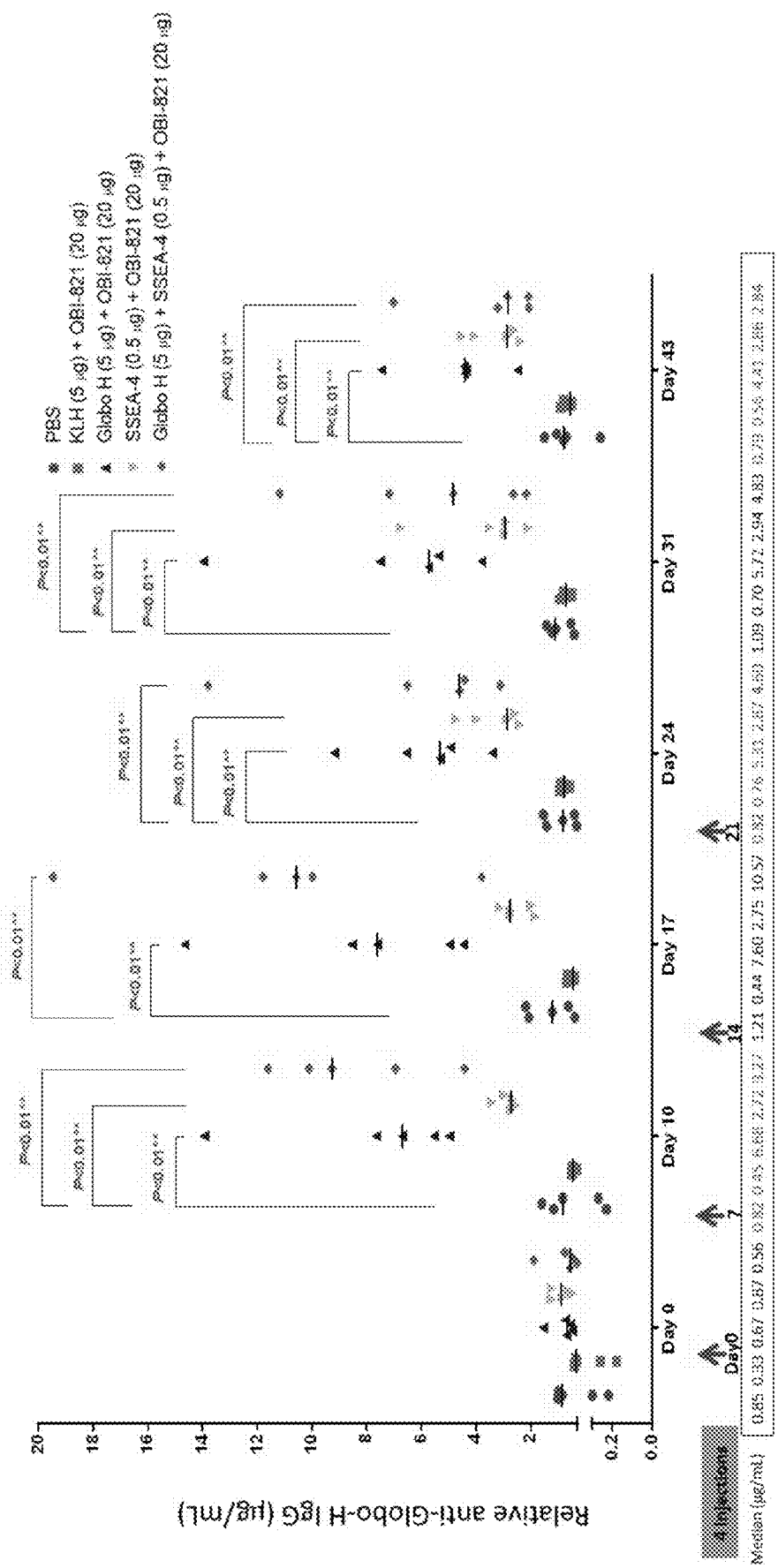
Figure 5E:
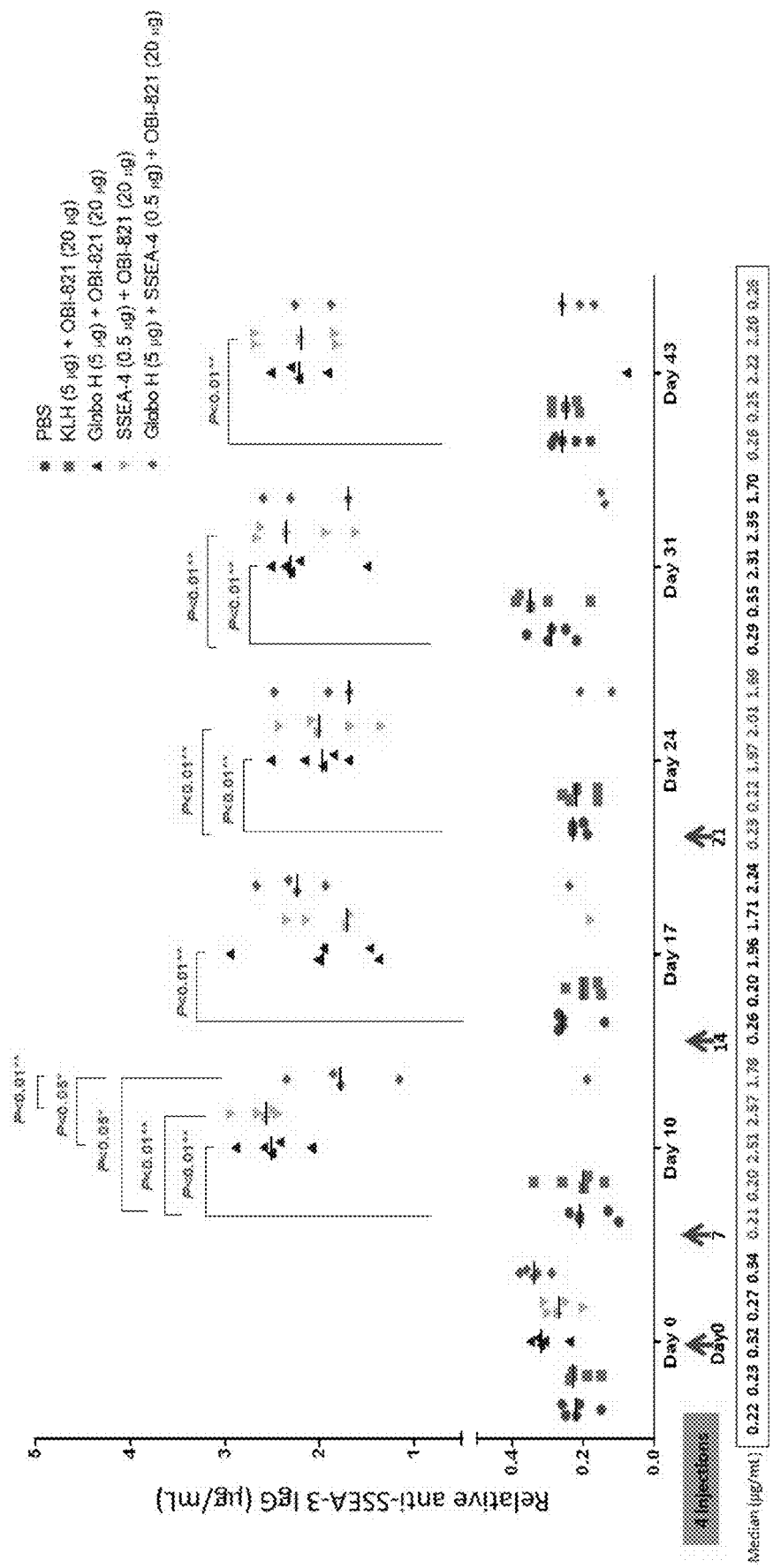
Figure 5F:
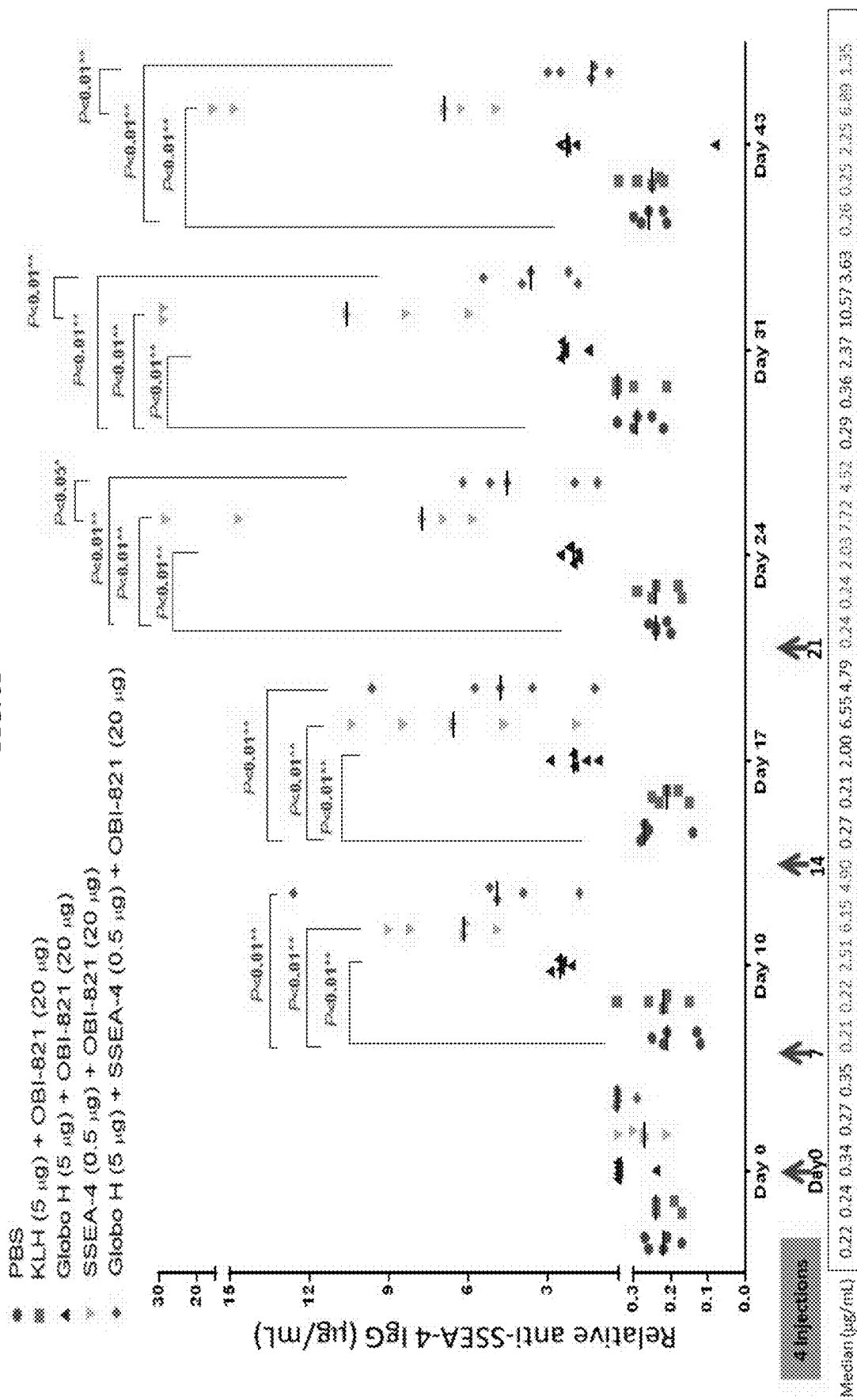

As shown in FIG. 3, mice treated with SSEA-4-KLH vaccine+OBI-821 adjuvant (FIG. 3A) and SSEA-4-DT vaccine+OBI-821 adjuvant (FIG. 3B) responded with anti-SSEA-4 IgM levels on Day 10 at three different exemplary representative vaccine doses (0.05, 0.5 and 5 µg), respectively. Anti-SSEA-4 IgM levels maintained those levels from Day 10 to Day 43. However, anti-SSEA-4 IgM levels of SSEA-4-DT vaccine were lower than SSEA-4-KLH vaccine. Similarly, anti-SSEA-4 IgG levels of SSEA-4-DT vaccine were lower than SSEA-4-KLH vaccine (shown in FIGS. 3C and 3D). It indicated that KLH was a better carrier protein than DT which could induce higher antibody response.

As shown in FIG. 4, mice treated with SSEA-4-KLH vaccine+OBI-834 adjuvant (FIG. 4A) and SSEA-4-DT vaccine+OBI-834 adjuvant (FIG. 4B) responded with anti-SSEA-4 IgM levels on Day 21 at three different exemplary representative vaccine doses (0.05, 0.5 and 5 µg), respectively. Anti-SSEA-4 IgM levels maintained those levels from Day 21 to Day 50. However, anti-SSEA-4 IgM levels of SSEA-4-DT vaccine were lower than SSEA-4-KLH vaccine. Similarly, anti-SSEA-4 IgG levels of SSEA-4-DT vaccine were lower than SSEA-4-KLH vaccine (shown in FIGS. 4C and 4D). It indicated that KLH was a better carrier protein than DT which could induce higher antibody response.

2. Representative Bi-Valent Vaccine Potency Assay (SSEA-4-KLH+Globo H-KLH Combined with OBI-821 Adjuvant) Demonstrating Efficacy According the previous result, we selected KLH and OBI-821 for the following experiments. As shown in FIG. 5, mice treated with SSEA-4-KLH vaccine+OBI-821 adjuvant responded with anti-Globo H (FIG. 5A), anti-SSEA-3 (FIG. 5B) and anti-SSEA-4 (FIG. 5C) IgM levels on Day 10 and maintained those levels from Day 10 to Day 43, respectively. Similarly, mice treated with SSEA-4-KLH vaccine+OBI-821 adjuvant responded with anti-Globo H (FIG. 5D), anti-SSEA-3 (FIG. 5E) and anti-SSEA-4 (FIG. 5F) IgG levels on Day 10 and maintained those levels from Day 10 to Day 43, respectively.

Figure 6A:
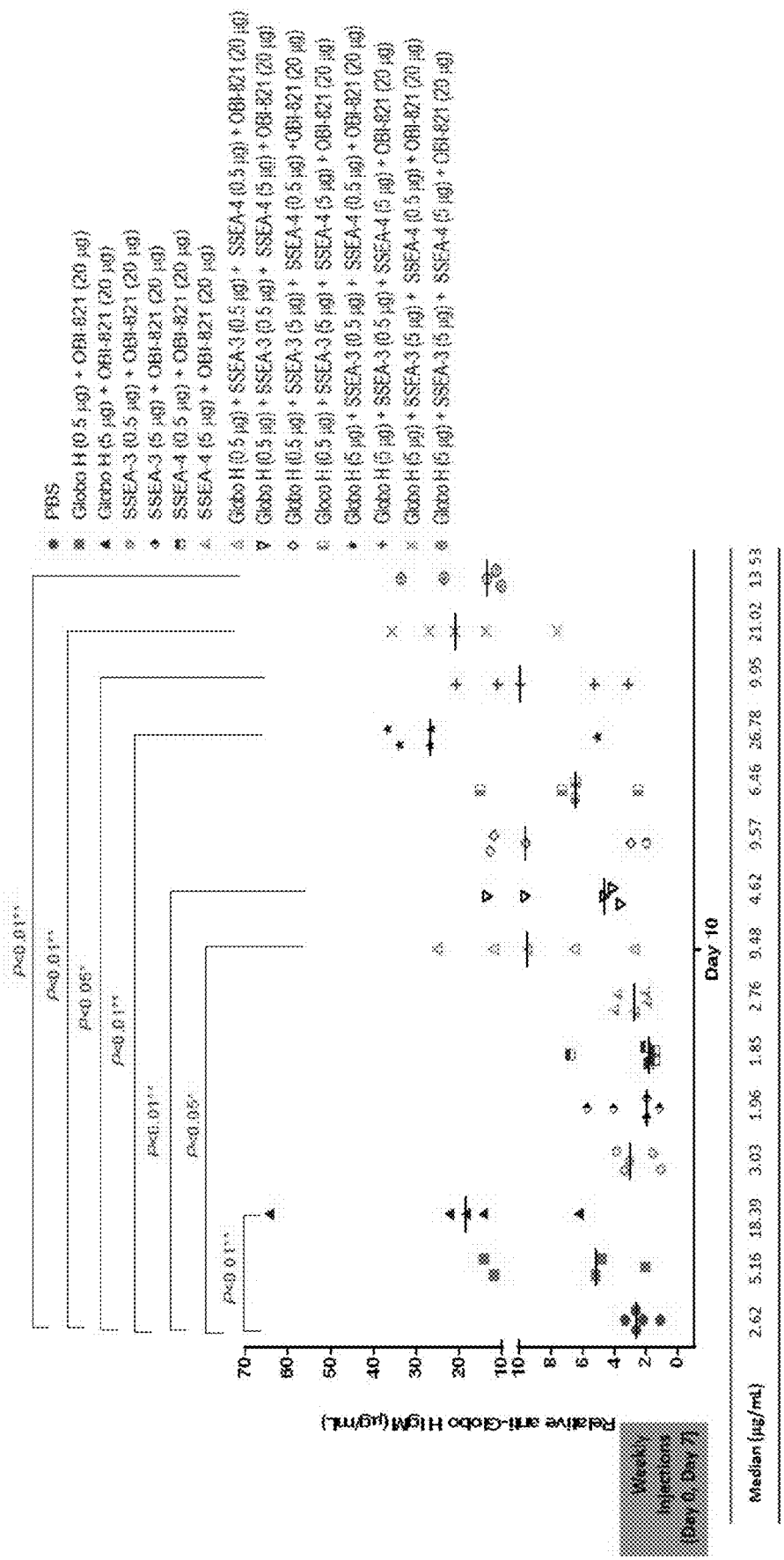
Figure 6B:
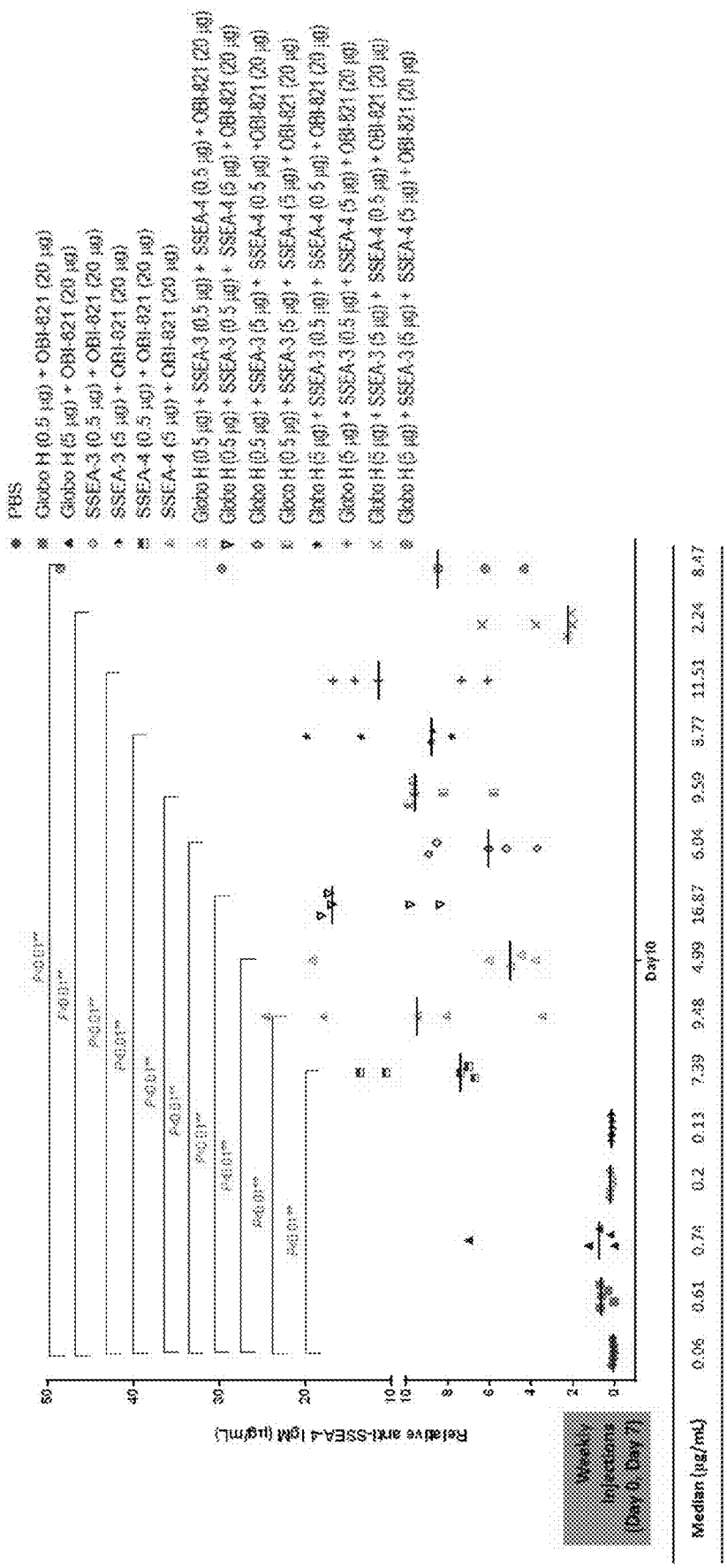
Figure 6C:
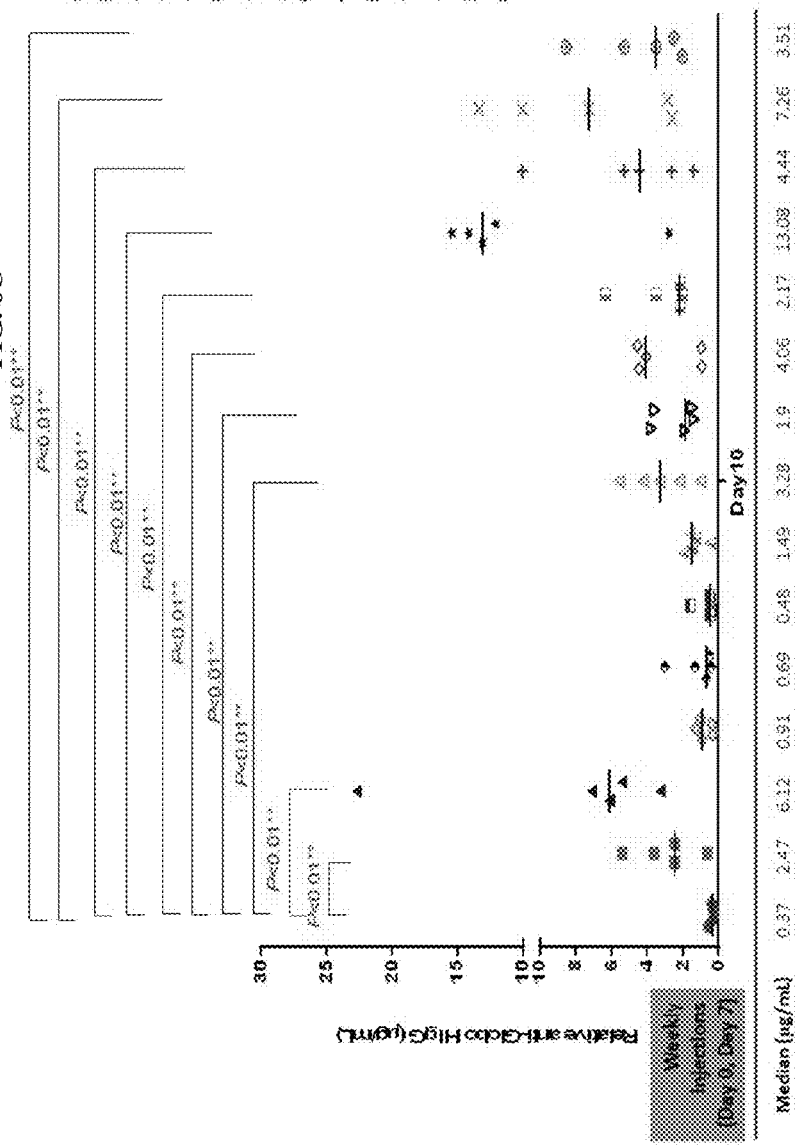

3. Representative Tri-Valent Vaccine Potency Assay (SSEA-4-KLH+Globo H-KLH+SSEA-3-KLH Combined with OBI-821 Adjuvant) Demonstrating Efficacy Finally, we established a tri-valent vaccine (SSEA-4-KLH+Globo H-KLH+SSEA-3-KLH) for the following assay. As shown in FIG. 6, mice treated with tri-valent vaccine+OBI-821 adjuvant responded with anti-Globo H (FIG. 6A) and anti-SSEA-4 (FIG. 6B) IgM levels on Day 10. Similarly, mice treated with tri-valent vaccine+OBI-821 adjuvant responded with anti-Globo H (FIG. 6C) and anti-SSEA-4 (FIG. 6D) IgG levels on Day 10. These positive results indicated the immunogenicity of single or multi-valent vaccines in Globo series antigens (Globo H, SSEA-3 and SSEA-4).

Unless defined otherwise, all technical and scientific terms and any acronyms used herein have the same meanings as commonly understood by one of ordinary skill in the art in the field of this invention. Although any compositions, methods, kits, and means for communicating information similar or equivalent to those described herein can be used to practice this invention, the preferred compositions, methods, kits, and means for communicating information are described herein.

All references cited herein are incorporated herein by reference to the full extent allowed by law. The discussion of those references is intended merely to summarize the assertions made by their authors. No admission is made that any reference (or a portion of any reference) is relevant prior art. Applicants reserve the right to challenge the accuracy and pertinence of any cited reference.

What is claimed is:

1. A pharmaceutical composition comprising:
(a) glycoconjugates comprising thiolated KLH moiety subunits covalently linked to a plurality of SSEA-4 antigens through a 4-(N-Maleimidomethyl)-cyclohexane-1-carboxylate (MCCa) linker under inert gas; and (b) an OBI-821 adjuvant, wherein the thiolated KLH moiety subunits of the glycoconjugate aggregate to form multimeric structures, the major multimeric structure of which is a trimer.

2. A vaccine comprising:
(a) SSEA-4 antigens; and
(b) a carrier protein which is KLH,
wherein the SSEA-4 antigens are covalently linked to thiolated KLH moiety subunits through a 4-(N-Maleimidomethyl)-cyclohexane-1-carboxylate (MCCa) linker under inert gas, and
wherein the KLH moiety subunits conjugated to the SSEA-4 antigens aggregate to form multimeric structures, the major multimeric structure of which is a trimer.

3. The vaccine of claim 2 further comprising a second composition comprising:
(a) Globo H antigens; and
(b) a carrier protein which is KLH,
wherein the Globo H antigens are covalently linked to thiolated KLH moiety subunits through a 4-(N-Maleimidomethyl)-cyclohexane-1-carboxylate (MCCa) linker under inert gas,
wherein the KLH moiety subunits conjugated to the Globo H antigens aggregate to form multimeric structures, the major multimeric structure of which is a trimer.

4. The vaccine of claim 3 further comprising a third composition comprising:

(a) SSEA-3 antigens; and
(b) a carrier protein which is KLH,
wherein the SSEA-3 antigens are covalently linked to thiolated KLH moiety subunits through a 4-(N-Maleimidomethyl)-cyclohexane-1-carboxylate (MCCa) linker under inert gas,
wherein the KLH moiety subunits conjugated to the SSEA-3 antigens aggregate to form multimeric structures, the major multimeric structure of which is a trimer.

5. A method of inducing or enhancing immune reaction in a subject in need thereof comprising:
administering an immunogenically effective amount of the vaccine of claim 2;
wherein the vaccine is administered two or more times.

6. The method of claim 5, wherein the administering further comprises the addition of immune response booster agents.

7. The method of claim 5, wherein the subject is human.

8. The method of claim 5, wherein the immunologically effective amount is from about 0.01 µg to about 250 mg.

9. A method of treating a Globo series antigen expressing cancer comprising administering to a patient in need thereof a therapeutically effective amount of a vaccine of claim 2, 3 or 4.

10. The method of claim 9, wherein the vaccine is administered two or more times.

11. The method of claim 9, wherein the cancer is sarcoma, skin cancer, leukemia, lymphoma, brain cancer, lung cancer, breast cancer, oral cancer, esophagus cancer, stomach cancer, liver cancer, bile duct cancer, pancreas cancer, colon cancer, kidney cancer, cervix cancer, ovary cancer or prostate cancer.

* * * * *